(12) United States Patent
Gomis et al.

(10) Patent No.: US 12,312,642 B2
(45) Date of Patent: May 27, 2025

(54) METHOD FOR THE DIAGNOSIS, PROGNOSIS AND TREATMENT OF BREAST CANCER METASTASIS

(71) Applicants: FUNDACIO INSTITUT DE RECERCA BIOMEDICA (IRB BARCELONA), Barcelona (ES); INSTITUCIO CATALANA DE RECERCA I ESTUDIS AVANCATS, Barcelona (ES)

(72) Inventors: Roger Gomis, Barcelona (ES); Maria Tarragona, Barcelona (ES); Anna Arnal, Barcelona (ES); Milica Pavlovic, Lajkovac (RS)

(73) Assignees: FUNDACIO INSTITUT DE RECERCA BIOMEDICA (IRB BARCELONA), Barcelona (ES); INSTITUCIO CATALANA DE RECERCA I ESTUDIS AVANCATS, Barcelona (ES)

( * ) Notice: Subject to any disclaimer, the term of this patent is extended or adjusted under 35 U.S.C. 154(b) by 84 days.

(21) Appl. No.: 17/385,568

(22) Filed: Jul. 26, 2021

(65) Prior Publication Data
US 2022/0049316 A1 Feb. 17, 2022

Related U.S. Application Data

(62) Division of application No. 16/028,530, filed on Jul. 6, 2018, now Pat. No. 11,072,831, which is a division of application No. 13/878,114, filed as application No. PCT/ES2011/070693 on Oct. 5, 2011, now Pat. No. 10,047,398.

(30) Foreign Application Priority Data

Oct. 6, 2010 (ES) ............................. ES201031478
Jun. 27, 2011 (ES) ............................. ES201131073

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,274,338 B1 | 8/2001 | Glimcher et al. | |
| 6,740,522 B2 | 5/2004 | Anderson | |
| 7,019,028 B2 | 3/2006 | Eder et al. | |
| 7,097,834 B1 | 8/2006 | Boyle | |
| 7,364,736 B2 | 4/2008 | Boyle et al. | |
| 7,411,050 B2 | 8/2008 | Anderson | |
| 8,642,270 B2 | 2/2014 | Leyland-Jones et al. | |
| 9,127,302 B2 | 9/2015 | Verrant et al. | |
| 9,134,237 B2 | 9/2015 | Connelly et al. | |
| 9,702,878 B2 | 7/2017 | Gomis et al. | |
| 10,006,091 B2 | 6/2018 | Gomis et al. | |
| 10,047,398 B2 | 8/2018 | Gomis et al. | |
| 10,114,022 B2 | 10/2018 | Gomis et al. | |
| 10,119,171 B2 | 11/2018 | Gomis et al. | |
| 10,793,642 B2 | 10/2020 | Gomis et al. | |
| 10,866,241 B2 | 12/2020 | Gomis et al. | |
| 11,041,213 B2 | 6/2021 | Gomis et al. | |
| 11,041,861 B2 | 6/2021 | Gomis et al. | |
| 11,072,831 B2 | 7/2021 | Gomis et al. | |
| 11,352,673 B2 | 6/2022 | Gomis et al. | |
| 11,591,599 B2 | 2/2023 | Gomis et al. | |
| 11,596,642 B2 | 3/2023 | Gregory et al. | |
| 11,654,153 B2 | 5/2023 | Gregory et al. | |
| 2004/0138313 A1 | 7/2004 | Eder et al. | |
| 2005/0018175 A1 | 1/2005 | Cheng | |
| 2005/0181375 A1 | 8/2005 | Aziz et al. | |
| 2008/0219996 A1 | 9/2008 | Kalebic et al. | |
| 2009/0029378 A1 | 1/2009 | Connelly et al. | |
| 2009/0048117 A1 | 2/2009 | Glimcher et al. | |
| 2009/0220955 A1 | 9/2009 | Verrant | |

(Continued)

FOREIGN PATENT DOCUMENTS

| | | |
|---|---|---|
| EP | 0120694 A2 | 10/1984 |
| EP | 0125023 A1 | 11/1984 |

(Continued)

OTHER PUBLICATIONS

Costa et al. The Breast. 2007. 16: S16-S20 (Year: 2007).*
Andrews, N.C., et al., "The ubiquitous subunit of erythroid transcription factor NF-E2 is a small basic-leucine zipper protein related to the v-maf oncogene," *Proc. Natl. Acad. Sci USA* 90(24):11488-11492, National Academy of Sciences, United States (1993).
Bos, P.D., et al., "Genes that mediate breast cancer metastasis to the brain," *Nature* 459(7249):1005-1009, Nature Publishing Group, United Kingdom (2009).
Brufsky, A.M., et al., "The evolving role of bone-conserving therapy in patients with breast cancer," *Semin. Oncol.* 37 Suppl. 1:S12-S19, W.B. Saunders, United States (2010).

(Continued)

*Primary Examiner* — Carla J Myers
(74) *Attorney, Agent, or Firm* — Sterne, Kessler, Goldstein & Fox P.L.L.C.

(57) ABSTRACT

The present invention relates to a method for the diagnosis or the prognosis of metastasis in breast cancer which comprises determining if the c-MAF gene is amplified in a primary tumor sample. Likewise, the invention also relates to a method for the diagnosis or the prognosis of metastasis in ER-breast cancer, as well as to a method for determining the tendency to develop bone metastasis with respect to metastasis in other organs, which comprise determining the c-MAF gene expression level. Finally, the invention relates to the use of a c-MAF inhibitor as therapeutic target for treating the ER-breast cancer metastasis.

20 Claims, 14 Drawing Sheets

Specification includes a Sequence Listing.

(56) References Cited

U.S. PATENT DOCUMENTS

| | | |
|---|---|---|
| 2010/0113297 A1 | 5/2010 | Lidereau et al. |
| 2010/0210738 A1 | 8/2010 | Leyland-Jones et al. |
| 2011/0130296 A1 | 6/2011 | Benz et al. |
| 2011/0150979 A1 | 6/2011 | Ray et al. |
| 2011/0152113 A1 | 6/2011 | Escudero et al. |
| 2011/0269637 A1 | 11/2011 | Broet et al. |
| 2014/0057796 A1 | 2/2014 | Gomis et al. |
| 2014/0105918 A1 | 4/2014 | Gomis et al. |
| 2014/0162887 A1 | 6/2014 | Martin et al. |
| 2014/0303133 A1 | 10/2014 | Pietenpol et al. |
| 2014/0314792 A1 | 10/2014 | Gomis et al. |
| 2015/0152506 A1 | 6/2015 | Gomis et al. |
| 2015/0293100 A1 | 10/2015 | Gomis et al. |
| 2015/0362495 A1 | 12/2015 | Gomis et al. |
| 2016/0032399 A1 | 2/2016 | Gomis et al. |
| 2016/0032400 A1 | 2/2016 | Gomis et al. |
| 2016/0040247 A1 | 2/2016 | Gomis et al. |
| 2017/0002357 A1 | 1/2017 | Gomis et al. |
| 2017/0088900 A1 | 3/2017 | Anjamshoaa et al. |
| 2017/0101683 A1 | 4/2017 | Gomis et al. |
| 2017/0121777 A1 | 5/2017 | Gomis et al. |
| 2017/0369589 A1 | 12/2017 | Gomis et al. |
| 2017/0370935 A1 | 12/2017 | Gomis et al. |
| 2019/0119757 A1 | 4/2019 | Gomis et al. |
| 2019/0169693 A1 | 6/2019 | Gomis et al. |
| 2019/0242898 A1 | 8/2019 | Gomis et al. |
| 2019/0256922 A1 | 8/2019 | Gomis et al. |
| 2019/0269707 A1 | 9/2019 | Gregory et al. |
| 2019/0309299 A1 | 10/2019 | Gomis et al. |
| 2021/0137952 A1 | 5/2021 | Gregory et al. |
| 2021/0190784 A1 | 6/2021 | Gomis et al. |
| 2021/0317534 A1 | 10/2021 | Gomis et al. |
| 2021/0388452 A1 | 12/2021 | Gomis et al. |
| 2022/0042997 A1 | 2/2022 | Gomis et al. |
| 2023/0323356 A1 | 10/2023 | Gomis et al. |
| 2023/0381209 A1 | 11/2023 | Gregory et al. |
| 2024/0000816 A1 | 1/2024 | Gregory et al. |

FOREIGN PATENT DOCUMENTS

| | | |
|---|---|---|
| EP | 1961825 A1 | 8/2008 |
| EP | 2626431 A2 | 8/2013 |
| EP | 2650682 A1 | 10/2013 |
| WO | WO-9116880 A1 | 11/1991 |
| WO | WO-0055126 A2 | 9/2000 |
| WO | WO-0149288 A1 | 7/2001 |
| WO | WO-03020278 A1 | 3/2003 |
| WO | WO-03020721 A1 | 3/2003 |
| WO | WO-03059249 A2 | 7/2003 |
| WO | WO-2004000843 A1 | 12/2003 |
| WO | WO-2004014888 A1 | 2/2004 |
| WO | WO-2005029067 A2 | 3/2005 |
| WO | WO-2005046731 A1 | 5/2005 |
| WO | WO-2005063252 A1 | 7/2005 |
| WO | WO-2005086891 A2 | 9/2005 |
| WO | WO-2006012221 A1 | 2/2006 |
| WO | WO-2006135436 A2 | 12/2006 |
| WO | WO-2008098351 A1 | 8/2008 |
| WO | WO-2008104543 A2 | 9/2008 |
| WO | WO-2008142164 A2 | 11/2008 |
| WO | WO-2008145125 A1 | 12/2008 |
| WO | WO-2009045115 A1 | 4/2009 |
| WO | WO-2009049410 A1 | 4/2009 |
| WO | WO-2009146546 A1 | 12/2009 |
| WO | WO-2010000907 A1 | 1/2010 |
| WO | WO-2010136569 A1 | 12/2010 |
| WO | WO-2012045905 A2 | 4/2012 |
| WO | WO-2012125828 A2 | 9/2012 |
| WO | WO-2013153458 A2 | 10/2013 |
| WO | WO-2013182912 A2 | 12/2013 |
| WO | WO-2014057357 A2 | 4/2014 |
| WO | WO-2014140896 A2 | 9/2014 |
| WO | WO-2014140933 A2 | 9/2014 |
| WO | WO-2014184679 A2 | 11/2014 |
| WO | WO-2015052583 A2 | 4/2015 |
| WO | WO-2016092524 A1 | 6/2016 |
| WO | WO-2017203468 A1 | 11/2017 |
| WO | WO-2019102380 A1 | 5/2019 |

OTHER PUBLICATIONS

Fugiwara, K.T., et al., "Two new members of the maf oncogene family, mafK and mafF, encode nuclear b-Zip proteins lacking putative trans-activator domain," *Oncogene* 8(9):2371-2380, Nature Publishing Group, United Kingdom (1993).

Gene Expression Omnibus Database, Accession No. GSE 2603, made public on Jul. 28, 2005, accessed on Jun. 20, 2013, accessed at http://www.ncbi.nlm.nih.gov/geo/query/acc/cgi?acc=GSE+2603, 2 pages.

Gene Expression Omnibus Database, Accession No. GSE 2034, made public on Feb. 23, 2005, accessed on Jun. 20, 2013, accessed at http://www.ncbi.nlm.nih.gov/geo/query/acc/cgi?acc=GSE+2034, 7 pages.

Gene Expression Omnibus Database, Accession No. GSE 12276, made public on Jun. 13, 2009, accessed on Jun. 20, 2013, accessed at http://www.ncbi.nlm.nih.gov/geo/query/acc.cgi?acc=GSE12276, 2 pages.

Gene Expression Omnibus Database, Accession No. GSE 14020, made public on May 1, 2009, accessed on Jun. 20, 2013, accessed at http://www.ncbi.nlm.nih.gov/geo/query/acc.cgi?acc=GSE14020, 2 pages.

GenBank Database, NCBI Reference Sequence NG_016440, accessed on Jun. 20, 2013, accessed at http://www.ncbi.nlm.nih.gov/nuccore/NG_016440, 5 pages.

GenBank Database, NCBI Reference Sequence NM_005360, accessed on Jun. 20, 2013, accessed at http://www.ncbi.nlm.nih.gov/nuccore/NM_005360.4, 5 pages.

GenBank Database, NCBI Reference Sequence NM_001031804, accessed on Jun. 20, 2013, accessed at http://www.ncbi.nlm.nih.gov/nuccore/NM_001031804.2, 6 pages.

GenPept Database, NCBI Reference Sequence NP_005351.2, accessed on Jun. 20, 2013, accessed at http://www.ncbi.nlm.nih.gov/protein/NP_005351.2, 4 pages.

GenPept Database, NCBI Reference Sequence NP_001026974.1, accessed on Jun. 20, 2013, accessed at http://www.ncbi.nlm.nih.gov/protein/NP_001026974, 4 pages.

GenBank Database, NCBI Reference Sequence NT_010498, accessed on Jun. 20, 2013, accessed at http://www.ncbi.nlm.nih.gov/nuccore/NT_010498.15, 5 pages.

GenBank Database, NCBI Reference Sequence NT_010542, accessed on Jun. 20, 2013, accessed at http://www.ncbi.nlm.nih.gov/nuccore/NT_010542.15, 2 pages.

Hu, G., et al., "MTDH activation by 8q22 genomic gain promotes chemoresistance and metastasis of poor-prognosis breast cancer," *Cancer Cell* 15(1):9-20, Cell Press, United States (2009).

Igarashi, K., et al., "Activity and expression of murine small Maf family protein MafK," *J. Biol. Chem.*, 270(13):7615-7624, American Society for Biochemistry and Molecular Biology, United States (1995).

Kataoka, K., et al., "Small Maf proteins heterodimerize with Fos and may act as competitive repressors of the NF-E2 transcription factor," *Mol. Cell Biol.* 15(4):2180-2190, American Society for Microbiology, United States (1995).

Kataoka, K., et al., "Transactivation activity of Maf nuclear oncoprotein is modulated by Jun, Fos and small Maf proteins," *Oncogene* 12(1):53-62, Nature Publishing Group, United Kingdom (1996).

Köhler, G. and Milstein, C., "Continuous cultures of fused cells secreting antibody of predefined specificity," *Nature* 256(5517):495-497, Nature Publishing Group, United Kingdom (1975).

Pageau, S.C., "Denosumab," *MAbs* 1(3):210-215, Landes Bioscience, United States (2009).

Pollack, J.R., "Microarray analysis reveals a major direct role of DNA copy number alteration in the transcriptional program of human breast tumors," *Proc. Natl. Acad. Sci. USA* 99(20):12963-12968, National Academy of Sciences, United States (2002).

(56) References Cited

OTHER PUBLICATIONS

Rocques, N., et al., "GSK-3-mediated phosphorylation enhances Maf-transforming activity," *Mol. Cell* 28(4):584-597, Cell Press, United States (2007).

International Search Report and the Written Opinion for International Application No. PCT/ES2011/070693, issued on Feb. 7, 2012, European Patent Office, Netherlands, 13 pages.

International Preliminary Report on Patentability for International Application No. PCT/ES2011/070693, issued on Apr. 9, 2013, The International Bureau of WIPO, Sweden, 8 pages.

GenPept Database, UniProtKB/Swiss-Prot: O75444.2, accessed on Jul. 8, 2013, accessed at http://www.ncbi.nlm.nih.gov/protein/o75444, 6 pages.

U.S. Appl. No. 61/801,769, filed Mar. 15, 2013, inventor Gomis.

U.S. Appl. No. 61/888,984, filed Oct. 9, 2013, inventors Gomis et al.

Abbott Molecular, "Vysis LSI IGH/MAF Dual Color Dual Fusion Probe," accessed at http://abbottmolecular.com/us/products/analyte-specific-reagent/fish/vysis-lsi-igh-maf-dual-color-dual-fusion-probe.html, accessed on Oct. 16, 2014, 2 pages.

Abnova, "MAF FISH Probe," accessed at http://abnova.com/products/products_detail.asp?Catalog_id=FA0375, accessed on Oct. 16, 2014, 2 pages.

Afinitor.com, "Afinitor (everolimus) Tablets," accessed at http://afinitor.com/sega-tuberosclerosis/patient/sega-information.jsp, accessed on Oct. 16, 2014, 5 pages.

Agilent Technologies, "Probes for Chromosome 16," accessed at http://genomics.agilent.com/productSearch.jsp?chr=16&start=79483700&end=79754340&_requestid=78075, accessed on Oct. 16, 2014, 3 pages.

Altschul, S.F., et al., "Basic Local Alignment Search Tool," *Journal of Molecular Biology* 215(3):403-410, Academic Press Limited, United Kingdom (1990).

ARUP Laboratories, "Multiple Myeloma (MM) by FISH: Detection of Prognostically Significant Genomic Aberrations in Multiple Myeloma (MM) by Fluorescence in situ Hybridization (FISH)," accessed at http://aruplab.com, accessed on Oct. 16, 2014, 2 pages.

Badve, S., et al. "Basal-like and Triple-negative Breast Cancers: a Critical Review with an Emphasis on the Implications for Pathologists and Oncologists," *Modern Pathology* 24(2):157-167, USCAP, United States (2011).

Barrett, T., et al., "NCBI GEO: Mining Tens of Millions of Expression Profiles—Database and Tools Update," *Nucleic Acids Research* 35(*Database Issue*):D760-D765, Oxford University Press, United Kingdom (2007).

Baselga, J., et al., "Everolimus in Postmenopausal Hormone-Receptor-Positive Advanced Breast Cancer," *The New England Journal of Medicine* 366(6):520-529, Massachusetts Medical Society, United States (2012).

Bertucci, F., et al., "How Basal are Triple-Negative Breast Cancers?," *International Journal of Cancer* 123(1):236-240, Wiley-Liss, United States (2008).

Bogado, C.E., et al., "Denosumab: an Update," *Drugs of Today* 47(8):605-613, Prous Science, S.A.U., United States (2011).

Bohn, O.L., et al., "Biomarker Profile in Breast Carcinomas Presenting with Bone Metastasis," *International Journal of Clinical and Experimental Pathology* 3(2):139-146, E-Century Publishing Corporation, United States (2010).

Cancer Genome Atlas Network, "Comprehensive Molecular Portraits of Human Breast Tumors," *Nature* 490(7418):61-70, Nature Publishing Group, United Kingdom (2012).

Carey, L.A., "Triple-Negative (basal-like) Breast Cancer: a New Entity," *Breast Cancer Research* 9(Suppl1):S13, BioMed Central Ltd., United Kingdom (2007).

CGI Italia, "IGH/MAF Two Color, Two Fusion Translocation Probe," accessed at http://cancergeneticsitalia.com/dna-fish-probe/ighmaf/, accessed on Oct. 16, 2014, 1 page.

Choi, M., et al., "Genetic Diagnosis by Whole Exome Capture and Massively Parallel DNA Sequencing," *Proceedings of the National Academy of Sciences of USA* 106(45):19096-19101, National Academy of Sciences, United States (2009).

Coleman, R.E., et al., "Breast-Cancer Adjuvant Therapy with Zoledronic Acid," *The New England Journal of Medicine* 365(15):1396-1405, Massachusetts Medical Society, United States (2011).

Creative Bioarray, "IGH/MAF Translocation, Dual Fusion Probe, " accessed at http://www.creative-bioarray.com/IGH-MAF-Translocation,-Dual-Fusion-Probe-FHPC-066-item-4707.htm, accessed on May 21, 2015, 2 pages.

Curtis, C., et al., "The Genomic and Transcriptomic Architecture of 2,000 Breast Tumours Reveals Novel Subgroups," *Nature* 486(7403):346-352, Macmillan Publishers Limited, United Kingdom (2012).

Cytocell, "Oncology and Constitutional FISH Probe Catalogue 2012/2013," accessed at http://zentech.be/uploads/docs/products_info/prenatalogy/cytocell%202012-2013%20catalogue%5B3%5D.pdf, accessed on Oct. 16, 2014, 134 pages.

Dako, "SureFISH Probes," accessed at http://dako.com/us/ar42/psg42806000/baseproducts_surefish.htm?setCountry=true&purl=ar42/psg42806000/baseproducts_surefish.htm?undefined&submit=Accept%20country, accessed on Oct. 16, 2014, 2 pages.

Dannhardt, G. and Kiefer, W., "Cyclooxygenase Inhibitors—Current Status and Future Prospects," *European Journal of Medicinal Chemistry* 36(2):109-126, Editions Scientifiques et Medicales Elsevier SAS, France (2001).

Dean-Colomb, W., et al., "Elevated Serum PINP Predicts Development of Bone Metastasis and Survival in Early-Stage Breast Cancer," *Breast Cancer Research and Treatment* 137(2):631-636, Springer Science, United States (2012).

Demarest, J.F., et al., "Update on Aplaviroc: an HIV Entry Inhibitor Targeting CCR5," *Retrovirology* 2(Suppl 1):S13, BioMed Central, United Kingdom (2005).

Ettenberg, S.A., et al., "BHQ880, a Novel Anti-DKK1 Neutralizing Antibody, Inhibits Tumor-Induced Osteolytic Bone Disease," *Proceedings of the American Association for Cancer Research* 49:947, American Association for Cancer Research, United States (2008).

Eychene, A., et al., "A New MAFia in Cancer," *Nature Reviews Cancer* 8(9):683-693, Nature Publishing Group, United Kingdom (2008).

Fili, S., et al., "Therapeutic Implications of Osteoprotegerin," *Cancer Cell International* 9:26:1-8, BioMed Central Ltd., United Kingdom (2009).

Gentleman, R.C., et al., "Bioconductor: Open Software Development for Computational Biology and Bioinformatics," *Genome Biology* 5(10):R80, 16 pages, BioMed Central Ltd, United Kingdom (2004).

Genycell Biotech, "FISH Mieloma Multiple," accessed at http://google.com/url?sa=t&rct=j&q=&esrc=s&source=web&cd=1&ved=CCQQFjAA&url=http%3A%2F%2Fwww.genycell.es%2Fimages%2Fproductos%2Fbrochures%2Flphmie6_86.ppt&ei=MhFYUOi3GKWH0QGlt4DoDw&usg=AFQjCNEqQMbT8vQGjJbi9riEf31VgoFTFQ&sig2=V5IS8juEMVHB18Mv2Xx Ww, accessed on Oct. 16, 2014, 1 page.

Giancotti, V., "Breast Cancer Markers," *Cancer Letters* 243(2):145-159, Elsevier Ireland Ltd., Ireland (2006).

Gnant, M., et al., "Adjuvant Bisphosphonates in Endocrine-responsive Breast Cancer: What is their Place in Therapy?" *Therapeutic Advances in Medical Oncology* 1(3):123-136, Sage, United Kingdom (2009).

Goss, P.E., and Chambers, A.F., "Does Tumour Dormancy Offer a Therapeutic Target?" *Nature Reviews. Cancer* 10(12):871-877, Macmillan Publishers Ltd., United Kingdom (2010).

Gur-Dedeoglu, B., et al., "A Resampling-Based Meta-Analysis for Detection of Differential Gene Expression in Breast Cancer," *BMC Cancer* 8:396, BioMed Central Ltd, United Kingdom (2008).

Hammond, M.E.H., et al., "American Society of Clinical Oncology/College of American Pathologists Guideline Recommendations for Immunohistochemical Testing of Estrogen and Progesterone Receptors in Breast Cancer," *Journal of Clinical Oncology* 28(16):2784-2795, American Society of Clinical Oncology, United States (2010).

Henry, D.H., et al., "Randomized, Double-Blind Study of Denosumab Versus Zoledronic Acid in the Treatment of Bone Metastases in Patients with Advanced Cancer (Excluding Breast and Prostate

(56) References Cited

OTHER PUBLICATIONS

Cancer) or Multiple Myeloma," *Journal of Clinical Onocology* 29(9):1125-1132, American Society of Clinical Oncology, United States (2011).
Huang, Q. and Ouyang, X., "Biochemical-Markers for the Diagnosis of Bone Metastasis: a Clinical Review," *Cancer Epidemiology* 36(1):94-98, Elsevier Ltd., United Kingdom (2011).
Hurt, E.M., et al., "Overexpression of c-maf is a Frequent Oncogenic Event in Multiple Myeloma that Promotes Proliferation and Pathological Interactions with Bone Marrow Stroma," *Cancer Cell* 5(2):191-199, Cell Press, United States (2004).
U.S. Appl. No. 62/090,599, inventors Gomis, R., et al., filed Dec. 11, 2014.
GenBank Database, "*Homo sapiens* v-maf Avian Musculoaponeurotic Fibrosarcoma Oncogene Homolog (MAF), Transcript Variant 2, mRNA," NCBI Reference Sequence Accession No. NM_001031804.2, accessed at https://www.ncbi.nlm.nih.gov/nuccore/NM_001031804.2, accessed on April 3F, 2015, 6 pages.
International Preliminary Report on Patentability for Application No. PCT/IB2013/001204, European Patent Office, Rijswijk, Netherlands, mailed on Aug. 11, 2014, 35 pages.
International Search Report and Written Opinion for Application No. PCT/IB2013/001204, European Patent Office, Rijswijk, Netherlands, mailed on Dec. 17, 2013, 11 pages.
International Preliminary Report on Patentability for International Application No. PCT/IB2014/002675, The International Bureau of WIPO, Geneva, Switzerland, issued Apr. 12, 2016, 12 pages.
International Search Report and Written Opinion for International Application No. PCT/IB2014/002675, mailed on Jun. 3, 2015, 17 pages.
Kang, Y., et al., "A Multigenic Program Mediating Breast Cancer Metastasis to Bone," *Cancer Cell* 3(6):537-549, Cell Press, United States (2003).
Kharaishvili, G., et al., "Collagen Triple Helix Repeat Containing 1 Protein, Periostin and Versican in Primary and Metastatic Breast Cancer: an Immunohistochemical Study," *Journal of Clinical Pathology* 64(11):977-982, BMJ Publishing Group, United Kingdom (2011).
Knight III, W.A., et al., "Estrogen Receptor as an Independent Prognostic Factor for Early Recurrence in Breast Cancer," *Cancer Research* 37(12):4669-4671, American Association for Cancer Research, United States (1977).
Kuritzkes, D.R., "HIV-1 Entry Inhibitors: an Overview," *Current Opinion in HIV and AIDS* 4(2):82-87, Lippincott Williams & Wilkins, United States (2009).
Leica Biosystems, "Kreatech™ FISH Probes," accessed at http://leicabiosystems.com/ihc-ish/kreatech-fish-probes/, accessed on Oct. 16, 2014, 2 pages.
Maisano, R., et al., "Novel Therapeutic Approaches to Cancer Patients with Bone Metastasis," *Critical Reviews in Oncology/Hematology* 40(3):239-250, Elsevier Science Ireland Ltd., Ireland (2001).
MetaSystems, "24XCyte," acessed at http://metasystems-international.com/index.php?option=com_joodb&view=article&joobase=5*id=12%3Ad-5029-100-og&Itemid=272, accessed on Oct. 16, 2014, 2 pages.
Mystakidou, K., et al., "Randomized, Open Label, Prospective Study on the Effect of Zoledronic Acid on the Prevention of Bone Metastases in Patients with Recurrent Solid Tumors That Did Not Present with Bone Metastases at Baseline," *Medical Oncology* 22(2):195-201, Humana Press Inc., United States (2005).
Neville-Webbe, H.L. and Coleman, R.E., "Bisphosphonates and RANK Ligand Inhibitors for the Treatment and Prevention of Metastatic Bone Disease," *European Journal of Cancer* 46(7):1211-1222, Elsevier Science Ltd., United Kingdom (2010).
Ng, P.C. and Kirkness, E.F., "Whole Genome Sequencing," *Methods in Molecular Biology* 628:215-226, Springer Science+Business Media, LLC, Netherlands (2010).

Nguyen, D.X. and Massague, J., "Genetic Determinants of Cancer Metastasis," *Nature Reviews. Genetics* 8(5):341-352, Macmillan Publishers Limited, United Kingdom (2007).
Nguyen, D.X., et al., "Metastasis: From Dissemination to Organ-Specific Colonization," *Nature Reviews. Cancer* 9(4):274-284, Nature Publishing Group, United Kingdom (2009).
ZOMETA®, "About ZOMETA® (zoledronic acid) 4 mg/5 mL Injection," accessed at http://www.us.zometa.com/index.jsp?usertrack.filter_applied=true&NovaId=29353769344676433633, accessed on Apr. 3, 2015, 2 pages.
Paik, S., et al., "A Multigene Assay to Predict Recurrence of Tamoxifen-Treated, Node-Negative Breast Cancer," *The New England Journal of Medicine* 351(27):2817-2826, Massachusetts Medical Society, United States (2004).
Polascik, T.J., "Bisphosphonates in Oncology: Evidence for the Prevention of Skeletal Events in Patients with Bone Metastases," *Drug Design, Development and Therapy* 3:27-40, Dove Medical Press Ltd., New Zealand (2009).
Rojo, F., et al., "Nuclear PARP-1 Protein Overexpression is Associated with Poor Overall Survival in Early Breast Cancer," *Annals of Oncology* 23(5):1156-1164, Oxford University Press, United Kingdom (2012).
Rotstein, D.M., et al., "Spiropiperidine CCR5 Antagonists," *Bioorganic and Medicinal Chemistry Letters* 19(18):5401-5406, Elsevier Ltd., United Kingdom (2009).
Santana-Codina, N., et al., "A Transcriptome-proteome Integrated Network Identifies Endoplasmic Reticulum Thiol Oxidoreductase (ERp57) as a Hub that Mediates Bone Metastasis," *Molecular and Cellular Proteomics* 12(8):2111-2125, American Society for Biochemistry and Molecular Biology, United States (Apr. 2013).
Sen, B. and Johnson, F.M., "Regulation of Src Family Kinases in Human Cancers," *Journal of Signal Transduction* 2011(865819):1-14, Hindawi Publishing Corporation, United States (2011).
Swennenhuis, J.F., et al., "Construction of Repeat-Free Fluorescence in situ Hybridization Probes," *Nucleic Acids Research* 40(3):e20:1-8, Oxford University Press, United Kingdom (2012).
Thèry, C., et al., "Isolation and Characterization of Exosomes from Cell Culture Supernatants and Biological Fluids," *Current Protocols in Cell Biology* Chapter 3:3.22.1-3.22.29, John Wiley & Sons, Inc., United Kingdom (2006).
Velasco-Velazquez, M., et al., "CCR5 Antagonist Blocks Metastasis of Basal Breast Cancer Cells," *Cancer Research* 72(15):3839-3850, American Association for Cancer Research, United States (2012).
Washam, C.L., et al., "Identification of PTHrP(12-48) as a Plasma Biomarker Associated with Breast Cancer Bone Metastasis," *Cancer Epidemiology, Biomarkers and Prevention* 22(5):972-983, American Association for Cancer Research, United States (May 2013).
Winer, E.P., et al., "Activity of Cabozantinib (XL184) in Metastatic Breast Cancer (MBC): Results From a Phase 2 Randomized Discontinuation Trial (RDT)," Annual Meeting of the American Society of Clinical Oncology, Chicago, United States, 1 page (Jun. 1-5, 2012).
Zeiss, "FISH Probes: XL Haematology," accessed at https://microshop.zeiss.com/?440675675dedc6&1=en&p=uk&f=r&i=5000&o=&h=25&n=1&sd=000000-528-231-uk, accessed on Oct. 16, 2014, 3 pages.
Zhang, X.H-F., et al., "Latent Bone Metastasis in Breast Cancer Tied to Src-Dependent Survival Signals," *Cancer Cell* 16(1):67-78, Elsevier Inc., United States (2009).
Zhou, H., et al., "Updates of mTOR Inhibitors," *Anticancer Agents in Medicinal Chemistry* 10(7):571-581, Bentham Science Publishers, Netherlands (2010).
Extended European Search Report for EP Application No. 12382139.9, European Patent Office, Munich, Germany, dated Sep. 20, 2012, 8 pages.
GenBank Database, "*Homo sapiens* v-maf Avian Musculoaponeurotic Fibrosarcoma Oncogene Homolog (MAF), Transcript Variant 1, mRNA," NCBI Reference Sequence Accession No. NM_005360.4, accessed as https://www.ncbi.nlm.nih.gov/nuccore/NM_005360.4, accessed on Apr. 3, 2015, 5 pages.
Hadji, P., et al., "Adjuvant bisphosphonates in early breast cancer: consensus guidance for clinical practice from a European Panel," *Annals of Oncology* 27(3):379-390, Oxford University Press, United Kingdom (2016).

(56) References Cited

OTHER PUBLICATIONS

Coleman, R., et al., "Adjuvant Zoledronic Acid in Patients with Early Breast Cancer: Final Efficacy Analysis of the AZURE (BIG 01/04) Randomised Open-label Phase 3 Trial," The Lancet Oncology 15(9):997-1006, Lancet Publishing Group, United Kingdom (2014).

Dhesy-Thind, S., et al., "Use of Adjuvant Bisphosphonates and Other Bone-Modifying Agents in Breast Cancer: a Cancer Care Ontario and American Society of Clinical Oncology Clinical Practice Guideline," J Clin Oncol 35, American Society of Clinical Oncology, United States, 22 pages (published online before print Mar. 6, 2017).

Extended European Search Report for EP Application No. 15180897. 9, European Patent Office, Munich, Germany, mailed Sep. 29, 2016, 9 pages.

Finn, R.S., et al., "Targeting the Cyclin-dependent Kinases (CDK) 4/6 in Estrogen Receptor-positive Breast Cancers," Breast Cancer Research 18(1): 17, BioMed Central Ltd., United Kingdom, 11 pages (2016).

Hiraga, T., "Role of Cyclooxygenase-2 in the Bone Metastasis of the Breast Cancer [Nyugan No Honeteni Ni Okeru Shikurookishigenaze-2 No Yakuwari]," Bone 20(5):563-566, Japan (2006).

Largo, C., et al., "Identification of overexpressed genes in frequently gained/amplified chromosome regions in multiple myeloma," Haematologica 91(2):184-191, Ferrata Storti Foundation, Italy (2006).

Takahashi, S., "Anti-RANKL Antibody for Treatment of Patients with Bone Metastasis from Breast Cancer," Gan To Kagaku Ryoho 39(1):89-94, Gan To Kagaku Ryohosha, Tokyo, Japan (Jan. 2012).

Early Breast Cancer Trialists' Collaborative Group (EBCTCG), "Adjuvant bisphosphonate treatment in early breast cancer: meta-analyses of individual patient data from randomised trials," Lancet 386(10001):1353-1361, Elsevier, United Kingdom (2015).

AZURE Trial Protocol for: Coleman, R.E., et al., "Breast-Cancer Adjuvant Therapy with Zoledronic Acid," The New England Journal of Medicine 365(15):1396-1405, Massachusetts Medical Society, United States (2011), 144 pages.

ClinicalTrials.gov, "Study of Denosumab as Adjuvant Treatment for Women With High Risk Early Breast Cancer Receiving Neoadjuvant or Adjuvant Therapy (D-CARE)," Identifier NCT01077154, accessed at https://clinicaltrials.gov/ct2/show/NCT01077154, last accessed on Aug. 25, 2017, 6 pages.

Coleman, R., "Abstract P1-09-01: Impact of MAF Gene Amplification on Disease Recurrence and Effects of Adjuvant Zoledronic Acid in Early Breast Cancer," Cancer Research 77(4), 2 pages (Feb. 2017) including supplemental data.

Coleman, R., et al., "Effect of MAF Amplification on Treatment Outcomes with Adjuvant Zoledronic Acid in Early Breast Cancer: a Secondary Analysis of the International, Open-Label, Randomised, Controlled, Phase 3 AZURE (BIG 01/04) Trial," The Lancet Oncology 18(11):1543-1552, Lancet Publication, United Kingdom (Nov. 2017).

Gnant, M., et al., "Adjuvant Endocrine Therapy Plus Zoledronic Acid in Premenopausal Women With Early-stage Breast Cancer: 62-month Follow-up From the ABCSG-12 Randomised Trial," The Lancet Oncology 12(7):631-641, Lancet Pub. Group, United Kingdom (Jul. 2011).

Hospira Healthcare Corporation, "Prescribing Information: Zoledronic Acid for Injection, 4 mg/5 mL (0.8 mg/mL), zoledronic acid (as zoledronic acid monohydrate)," Control No. 182128, prepared May 4, 2015, accessed at https://www.hospira.ca/en/images/2015.05.04%20Zoledronic%20Acid%204%20mg%20Eng%20PI_tcm87-97657.PDF, 32 pages.

International Search Report and Written Opinion for International Application No. PCT/IB2017/053094, European Patent Office, Rijswijk, mailed on Aug. 14, 2017, 19 pages.

Kim, H., et al., "Multi-cancer Computational Analysis Reveals Invasion-associated Variant of Desmoplastic Reaction Involving INHBA, THBS2 and COL11A1," BMC Medical Genomics 3:11 pages, BioMed Central, United Kingdom (Nov. 2010).

Ministry of Health, Social Services and Equality, Data Sheet of "Zoledronic acid Kern Pharma 4 mg/100 mL Solution for Infusion EFG," Text Revised Jul. 2016, Machine-translated Jul. 6, 2017, 38 pages (Ministerio de Sanidad, Servicios Sociales e Igualdad, Ficha Tecnica de "Acido Zoledronico Kern Pharma 4 mg/100 ml Solucion Para Perfusion EFG").

Morito, N., et al., "Overexpression of c-Maf Contributes to T-Cell Lymphoma in Both Mice and Human," Cancer Research 66(2):812-819, American Association for Cancer Research, Japan (Jan. 2006).

Paterson, A.H.G. and Shea-Budgell, M.A., "Bone Health in Patients with Breast Cancer: Recommendations from an Evidence-Based Canadian Guideline," Journal of Clinical Medicine 2(4):283-301, MDPI AG, Switzerland (2013).

Paterson, A.H.G., et al., "Oral Clodronate for Adjuvant Treatment of Operable Breast Cancer (National Surgical Adjuvant Breast and Bowel Project protocol B-34): a Multicentre, Placebo-controlled, Randomised Trial," The Lancet Oncology 13(7):734-742, Lancet Pub. Group, United Kingdom (2012).

Supplementary Appendix for: Coleman, R.E., et al., "Breast-Cancer Adjuvant Therapy with Zoledronic Acid," The New England Journal of Medicine 365(15):1396-1405, Massachusetts Medical Society, United States (2011), 18 pages.

Al-Mulla, F., et al., "Expressive Genomic Hybridisation: Gene Expression Profiling at the Cytogenetic Level," Journal of Clinical Pathology: Molecular Pathology 56(4):210-217, BMJ Publishing Group, United Kingdom (2003).

Klopocki, E. and Mundlos, S., "Copy-number Variations, Noncoding Sequences, and Human Phenotypes," Annual Review of Genomics and Human Genetics 12:53-72, Annual Reviews, United States (2011).

Lipton, A., et al., "The Science and Practice of Bone Health in Oncology: Managing Bone Loss and Metastasis in Patients with Solid Tumors," Journal of the National Comprehensive Cancer Network 7(Suppl 7):S1-S30, Jones and Bartlett Publishers, United States (2009).

Pavlovic, M., et al., "Enhanced MAF Oncogene Expression and Breast Cancer Bone Metastasis," Journal of the National Cancer Institute 107(12):djv256:1-12, Oxford University Press, United States (2015), with Supplementary Materials and Methods, Cell Culture, Supplementary Table 1-5, 40 pages.

Sutherland, R.L., et al., "Expression and Regulation of Cyclin Genes in Breast Cancer," Acta Oncologica 34(5):651-656, Scandinavian University Press, United Kingdom (1995).

Weber-Mangal, S., et al., "Breast Cancer in Young Women (≤35 years): Genomic Aberrations Detected by Comparative Genomic Hybridization," International Journal of Cancer 107(4):583-592, Wiley-Liss, Inc., United States (2003).

Office action mailed Aug. 9, 2017, in U.S. Appl. No. 13/878,114, inventor Gomis, Roger, § 371(c) date Sep. 27, 2013, 18 pages.

Office action mailed Jun. 8, 2016, in U.S. Appl. No. 13/878,114, inventor Gomis, Roger, § 371(c) date Sep. 27, 2013, 20 pages.

Office action mailed Oct. 23, 2015, in U.S. Appl. No. 13/878,114, inventor Gomis, Roger, § 371(c) date Sep. 27, 2013, 27 pages.

Bruland Ø.S., et al., "High-Linear Energy Transfer Irradiation Targeted to Skeletal Metastases by the Alpha-emitter$^{223}$Ra: Adjuvant or Alternative to Conventional Modalities?," Clinical Cancer Research 12 (20 Pt 2):6250s-6257s, American Association for Cancer Research, Denville, NJ (Oct. 2006).

GenBank Database, "*Homo sapiens* v-maf avian musculoaponeurotic fibrosarcoma oncogene homolog (MAF), RefSeqGene on chromosome 16," NCBI Reference Sequence Accession No. NG_016440, accessed at http://www.ncbi.nlm.nih.gov/nuccore/NG_016440, accessed on Apr. 3, 2015, 5 pages.

GenPept Database, "RecName: Full=Transcription Factor Maf; AltName: Full=Proto-oncogene c-Maf; AltName: Full=V-maf Musculoaponeurotic Fibrosarcoma Oncogene Homolog [*Homo sapiens*]," UniProtKB/Swiss-Prot:Accession No. O75444.2, accessed at https://www.ncbi.nlm.nih.gov/protein/o75444, accessed on Apr. 3, 2015, 6 pages.

GenPept Database, "transcription factor Maf isoform a [*Homo sapiens*]" NCBI Reference Sequence Accession No. NP_005351.2, accessed at http://www.ncbi.nlm.nih.gov/protein/NP_005351.2, accessed on Apr. 3, 2015, 4 pages.

(56) References Cited

OTHER PUBLICATIONS

GenPept Database, "transcription factor Maf isoform b [*Homo sapiens*]" NCBI Reference Sequence Accession No. NP_001026974. 1, accessed at http://www.ncbi.nlm.nih.gov/protein/NP_001026974, accessed on Apr. 3, 2015, 4 pages.
Gralow, J., et al., "Phase III Trial of Bisphosphonates as Adjuvant Therapy in Primary Breast Cancer: SWOG/Alliance/ECOG-ACRIN/NCIC Clinical Trials Group/NRG Oncology Study S0307," ASCO meeting library (Jun. 1, 2015), accessed at https://meetinglibrary.asco.org/record/111882/abstract, accessed on Jul. 26, 2018, 2 pages.
Horlings, H.M., et al., "Integration of DNA Copy Number Alterations and Prognostic Gene Expression Signatures in Breast Cancer Patients," Clinical Cancer Research, 16(2):651-663, United States (Jan. 2010).
Liao, S., et al., "Identification of New Breast Cancer Candidate Genes Associated with Stromal Invasion," Cancer Research, Abstract #4036, 69(2 Suppl), (Jan. 2009), Retrieved from the Internet http://cancerres.aacrjournals.org/content/69/2_Supplement/4036, 4 pages.
Stopeck, A.T., et al., "Denosumab Compared with Zoledronic Acid for the Treatment of Bone Metastases in Patients with Advanced Breast Cancer: a Randomized, Double-Blind Study," Journal of Clinical Oncology 28(35): 5132-5139, Alexandria, American Society of Clinical Oncology, United States (Dec. 2010).
Van de Wetering de Rooi,J J., et al., "Safety, Pharmacokinetics and Efficacy of Anti-Rankl Nanobody® Alx-0141 in Healthy Postmenopausal Women," Annals of the Rheumatic Diseases 70(Suppl.3):p. 136, 2011 (Abstract).
Yakes F.M., et al., "Cabozantinib (XL184), a Novel MET and VEGFR2 Inhibitor Simultaneously Suppresses Metastasis, Angiogenesis, and Tumor Growth," Molecular Cancer Therapeutics 10(12):2298-2308, American Association for Cancer Research, Inc., Philadelphia, PA (Dec. 2011).
Co-pending U.S. Appl. No. 15/944,510, inventors Gomis R., et al., filed Apr. 3, 2018 (Not Published; now Abandoned).
Co-pending U.S. Appl. No. 15/955,790, Inventors Gomis, R., et al., filed Apr. 18, 2018 (Not Published; now Abandoned).
International Preliminary Report on Patentability for Application No. PCT/IB2017/053094, mailed on Sep. 3, 2018, 23 pages.
Annunziata, C.M., et al., "A Mechanistic Rationale for MEK Inhibitor Therapy in Myeloma Based on Blockade of MAF Oncogene Expression", Blood, 117(8):2396-2404, American Society of Hematology, United States (Feb. 2011).
Bowles, D.W., et al., "Multi-targeted Tyrosine Kinase Inhibitors in Clinical Development: Focus on XL-184 (Cabozantinib)," Drugs of today (Barcelona, Spain) 47(11):857-868, Clarivate Analytics, Spain (Nov. 2011).
Coleman, R.E., et al., "Benefits and risks of adjuvant treatment with zoledronic acid in stage II/III breast cancer. 10 years follow-up of the AZURE randomized clinical trial (BIG 01/04)," Journal of Bone Oncology, 13(1):123-135, Elsevier (Nov. 2018).
Costa, L and Ferreira, A.R., "Adjuvant zoledronic acid to treat breast cancer: not for all," The Lancet Oncology, 18(11):1437-1439, The Lancet Publishing Group, United Kingdom (Nov. 2017).
Extended European Search Report for Application No. 19159414, mailed on Jun. 13, 2019, 10 pages.
Extended European Search Report for EP Application No. 19165007, The Hague, Netherlands, mailed on May 22, 2019, 15 pages.
Fornier, M.N., et al., "Phase I Dose-finding Study of Weekly Docetaxel Followed by Flavopiridol for Patients with Advanced Solid Tumors," Clinical Cancer Research 13(19):5841-5846, The Association, United States (Oct. 2007).
GenBank Database, "*Homo sapiens* v-maf avian musculoaponeurotic fibrosarcoma oncogene homolog (MAF), transcript variant 2, mRNA," NCBI Reference Sequence Accession No. NM_001031804, accessed at http://www.ncbi.nlm.nih.gov/nuccore/NM_001031804.2, accessed on Apr. 3, 2015, 6 pages.
GenBank Database, "*Homo sapiens* v-maf avian musculoaponeurotic fibrosarcoma oncogene homolog (MAF), transcript variant 1, mRNA,"
NCBI Reference Sequence Accession No. NM_005360, accessed at http://www.ncbi.nlm.nih.gov/nuccore/NM_005360.4, accessed on Apr. 3, 2015, 5 pages.
Gnant, M., et al., "Adjuvant Denosumab in Breast Cancer (ABCSG-18): a Multicentre, Randomised, Double-Blind, Placebo-Controlled Trial," Lancet, 386(9992):433-443, Elsevier, United Kingdom (Aug. 2015).
Haas, M.J., "RANKLing Non-skeletal Tumors," SciBX, Nature Publishing Group, (2010), 2 pages.
Huober, J. and Thurlimann, B., "Bone Targeted Therapy in Breast Cancer: Present and Future," Critical Reviews in Oncology/Hematology 74 Suppl 1:S7-S10, Elsevier Scientific Publishers, Netherlands (Apr. 2010).
International Search Report and Written Opinion for Application No. PCT/IB2018/059189, mailed on May 7, 2019, 32 pages.
Johnson, K., "Denosumab Boosts Survival, Not Just Bones, in Breast Cancer," Medscape, Retrieved on [Apr. 23, 2019], Dec. 10, 2015, Retrieved From the Internet: (URL: https://www.medscape.com/viewarticle/855803), 1 page.
Liepe, K, "Alpharadin, a 223Ra-based Alpha-particle-emitting Pharmaceutical for the Treatment of Bone Metastases in Patients With Cancer," Current Opinion in Investigational Drugs 10(12):1346-1358, Thomson Reuters (Scientific) Ltd, United Kingdom (Dec. 2009).
Nakashima, T., et al., "New Molecular and Biological Mechanism of Antitumor Activities of KW-2478, a Novel Nonansamycin Heat Shock Protein 90 Inhibitor, in Multiple Myeloma Cells," Clinical Cancer Research 16(10):2792-2802, The Association, United States (May 2010).
Stein, C.A. and Cohen, J.S., "Oligodeoxynucleotides as Inhibitors of Gene Expression: a Review," Cancer Research 48(10):2659-2668, American Association for Cancer Research, United States (1988).
Yersal, O. and Barutca, S., "Biological Subtypes of Breast Cancer: Prognostic and Therapeutic Implications," World Journal of Clinical Oncology, 5(3):412-424, Baishideng Publishing Group, United States (Aug. 2014).
Dako Denmark A/S, "HER2 IQFISH pharmDxTM, Code K5731," Assay Information, $3^{rd}$ edition, 184 pages (Jun. 2015).
Supplementary Materials and Methods, Table 1-5, 40 pages (2011), in Coleman, R.E., et al., "Breast-Cancer Adjuvant Therapy with Zoledronic Acid," The New England Journal of Medicine 365(15):1396-1405, Massachusetts Medical Society, United States (2011).
Office Action mailed Mar. 24, 2020, in U.S. Appl. No. 16/028,530, Gomis, R., et al., filed Jul. 6, 2018, 24 pages.
Office Action mailed Nov. 20, 2020, in U.S. Appl. No. 16/028,530, Gomis, R., et al., filed Jul. 6, 2018, 16 pages.
Co-Pending U.S. Appl. No. 17/339,024, filed Jun. 4, 2021 (Not yet Published).
Co-Pending U.S. Appl. No. 17/353,013, filed Jun. 21, 2021 (Not yet Published).
Amit, A.G., et al., "Three-Dimensional Structure of an Antigen-Antibody Complex at 2.8 A Resolution," Science 233(4765):747-753, American Association for the Advancement of Science, United States (1986).
Caton, A.J., et al., "Identical D Region Sequences Expressed by Murine Monoclonal Antibodies Specific for a Human Tumor-associated Antigen," Journal of Immunology 144(5):1965-1968, American Association of Immunologists, United States (Mar. 1990).
Chothia, C. and Lesk, A. M., "Canonical Structures for the Hypervariable Regions of Immunoglobulins," Journal of Molecular Biology 196(4):901-917, Elsevier, United Kingdom (Aug. 1987).
Chothia, C., et al., "Conformations of Immunoglobulin Hypervariable Regions," Nature 342(6252):877-883, Nature Publishing Group, United Kingdom (Dec. 1989).
Creative Bioarray, "Products," accessed at http://creative-bioarray.com/Products.htm, accessed on Jun. 15, 2023, 6 pages.
Deeks, E.D., and Perry, C.M., "Zoledronic Acid: a Review of Its Use in the Treatment of Osteoporosis," Drugs Aging 25(11):963-986, SpringerLink, Germany (2008).
Drake, M.T., et al., "Bisphosphonates: mechanism of action and role in clinical practice," Mayo Clin. Proc. 83(9):1032-1045, Elsevier, Netherlands (Sep. 2008).

(56) References Cited

OTHER PUBLICATIONS

Gralow, J. R., et al., "Phase III Randomized Trial of Bisphosphonates as Adjuvant Therapy in Breast Cancer: S0307," J. Natl. Cancer Inst. 112(7):698-707, Oxford University Press, United Kingdom (Jul. 2020).

Haas, D, "On the Expanding, Then Contracting Scope of Scientific Publications," FEMS Microbiology Reviews 34(1):1-2, Oxford University Press, United Kingdom (Dec. 2009).

Holliger, P, and Hudson, P.J., "Engineered Antibody Fragments and the Rise of Single Domains," Nature Biotechnology 23(9):1126-1136, Nature America Publishing, United States (2005).

Kristensen, B., et al., "Oral Clodronate in Breast Cancer Patients With Bone Metastases: a Randomized Study," Journal of Internal Medicine, 246(1):67-74, Blackwell Scientific Publications, United Kingdom (1999).

Martin, M., et al., "Benefit of denosumab therapy in patients with bone metastases from breast cancer: a number-needed-to-treat (NNT) analysis," Breast (Edinburgh, Scotland) (Breast) 20(1):S85, Abstract P347, accessed at https://www.thebreastonline.com/article/S0960-9776(11)70283-1/pdf on Jun. 15, 2023, 1 page, Elsevier, Netherlands (Mar. 2011).

Paterson, A.H.G., et al., "Validation of MAF Biomarker for Response Prediction to Adjuvant Bisphosphonates in 2 Clinical Trials: AZURE and NSABP-B34," Journal of Clinical Oncology 38(15_suppl):513, 4 pages, American Society of Clinical Oncology, United States (May 2020).

Paterson, A.H.G., et al., "MAF Amplification and Adjuvant Clodronate Outcomes in Early-Stage Breast Cancer in NSABP B-34 and Potential Impact on Clinical Practice," JNCI Cancer Spectr. 5(4):pkab054, 8 pages, Oxford University Press, United Kingdom (May 2021).

Reis-Filho, J. S., "Triple Negative and Basal-like Breast Cancer: One or Many Diseases? Implications for Surgical Pathologists," accessed at https://web.archive.org/web/20130319192034/http://www.uscap.org/site~/98th/pdf/companion03h03.pdf, on Jun. 15, 2023, 19 pages, United States & Canadian Academy of Pathology, United States (2009).

Rosen, L,S., et al., "Zoledronic Acid Is Superior to Pamidronate for the Treatment of Bone Metastases in Breast Carcinoma Patients With at Least One Osteolytic Lesion," Cancer 100(1):36-43, Wiley, United States (2004).

Segal, D.M., et al., "The Three-dimensional Structure of a Phosphorylcholine-binding Mouse Immunoglobulin Fab and the Nature of the Antigen Binding Site," Proceedings of the National Academy of Sciences of the United States of America 71(11):4298-4302, National Academy of Sciences, United States (Nov. 1974).

Sharon, J., "Structural Correlates of High Antibody Affinity: Three Engineered Amino Acid Substitutions Can Increase the Affinity of an Anti-p-azophenylarsonate Antibody 200-fold," Proceedings of the National Academy of Sciences of the United States of America 87(12):4814-4817, National Academy of Sciences, United States (Jun. 1990).

Sharon, J., "Structural Characterization of Idiotopes by Using Antibody Variants Generated by Site-directed Mutagenesis," Journal of Immunology 144(12):4863-4869, American Association of Immunologists, United States (Jun. 1990).

Viprey, V.F., et al., "Neuroblastoma mRNAs Predict Outcome in Children With Stage 4 Neuroblastoma: a European HR-NBL1/SIOPEN Study," Journal of Clinical Oncology 32(10):1074-1083, American Society of Clinical Oncology, United States (Apr. 2014).

Zefei, J., et al., "Expert Consensus on Clinical Diagnosis and Treatment of Breast Cancer Bone Metastasis and Bone-related Diseases (2014 Edition)," Chinese Medical Journal 95(4):241-247, Chinese Medical Association, China (Jan. 2015).

Zhao, X. and Hu, X., "Dosing of Zoledronic Acid with its Anti-Tumor Effects in Breast Cancer," Journal of Bone Oncology 4(3):98-101, Elsevier, Netherlands (Oct. 2015).

Co-pending U.S. Appl. No. 18/169,537, inventors Gregory. W.M., et al., filed Feb. 15, 2023 (Not yet Published).

Co-pending U.S. Appl. No. 18/154,295, inventors Gomis. R., et al., filed Jan. 13, 2023 (Not yet Published).

Co-pending U.S. Appl. No. 18/298,807, inventors Gregory. W.M., et al., filed Apr. 11, 2023 (Not yet Published).

Baker, S.G., "The Central Role of Receiver Operating Characteristic (ROC) Curves in Evaluating Tests for the Early Detection of Cancer," Journal of the National Cancer Institute 95(7):511-515, Oxford University Press, England (Apr. 2003).

Ezra, A., et al., "Administration Routes and Delivery Systems of Bisphosphonates for the Treatment of Bone Resorption", Advanced Drug Delivery Reviews 42(3): 175-195 (2000).

Furukawa, H., et al., "Analysis of the Risk and Work Efficiency in Admixture Processes of Injectable Drugs using the Ampule Method and the Pre-filled Syringe Method", Japanese Journal of Pharmaceutical Health Care and Sciences 29(3): 270-278 (2003).

Lipton, A., et al., "The science and practice of bone health in oncology: managing bone loss and metastasis in patients with solid tumors," J Natl Compr Canc Netw 7(Suppl 7):S1-30, Jones and Bartlett Publishers, United States (Oct. 2009).

Anonymous, "Highlights of Prescribing Information—Zometa (zoledronic acid)", XP055980793, pp. 1-23 (2014).

Anonymous, "Product information BONEFOS® (sodium clodronate)", XP055980801, pp. 1-12 (2012).

Co-pending U.S. Appl. No. 18/883,685, inventors Gomis, R., et al., filed Sep. 12, 2024 (Not yet Published).

Coleman, R.E., "Bisphosphonates in breast cancer", Annals of Oncology 16(5):687-695, (May 2005), European Society for Medical Oncology.

Hadji, P. et al., "Effect of adjuvant bisphosphonates on disease-free survival in early breast cancer: Retrospective analysis results in an unselected single-center cohort", Journal of Bone Oncology 2(1):2-10 (Feb. 2013).

\* cited by examiner

| Ratio between the MAF / IGH gene copy number | MCF7 parents (n=199) | BoM2 (n=70) |
|---|---|---|
| ≤ 1.5 | 67.3% | 11.4% |
| > 1.5 | 32.7% | 88.6% |
| ≥ 2 | 21.1% | 75.7% |

METHOD FOR THE DIAGNOSIS, PROGNOSIS AND TREATMENT OF BREAST CANCER METASTASIS

CROSS-REFERENCE TO RELATED APPLICATIONS

This application is a divisional of U.S. application Ser. No. 16/028,530, filed Jul. 6, 2018, which is a divisional of U.S. application Ser. No. 13/878,114, which is a national stage of International Application No. PCT/ES2011/070693, filed Oct. 5, 2011, which claims foreign priority to Spain Patent Application Nos. P201131073, filed Jun. 27, 2011, and P201031478, filed Oct. 6, 2010, and are each incorporated herein by reference in their entirety.

REFERENCE TO SEQUENCE LISTING SUBMITTED ELECTRONICALLY VIA EFS-WEB

The content of the electronically submitted sequence listing (Name: "3190_0100004_Seqlisting ST25.txt"; Size: 30,443 bytes; Date of Creation: Jul. 9, 2021) filed with the application is incorporated herein by reference in its entirety.

Field of the Invention

The present invention relates to the diagnosis or the prognosis of metastasis in breast cancer based on determining if the c-MAF gene is amplified in a primary tumor sample. Likewise, the invention also relates to a method for the diagnosis or the prognosis of metastasis in breast cancer, as well as to a method for designing a customized therapy in a subject with breast cancer, which comprise determining the c-MAF gene expression level. Finally, the invention relates to the use of a c-MAF inhibitor as therapeutic target for the treatment of breast cancer metastasis.

Background of the Invention

Breast cancer is the second most common type of cancer worldwide (10.4%; after lung cancer) and the fifth most common cause of death by cancer (after lung cancer, stomach cancer, liver cancer, and colon cancer). Among women, breast cancer is the most common cause of death by cancer. In 2005, breast cancer caused 502,000 deaths worldwide (7% of the deaths by cancer; almost 1% of all deaths). The number of cases worldwide has increased significantly from the 1970s, a phenomenon which is partly due to the modern lifestyle in the western world.

Breast cancer is classified into stages according to the TNM system. The prognosis is closely related the results of the stage classification, and the stage classification is also used to assign patients to treatments both in clinical trials and in the medical practice. The information for classifying into stages is as follow:

TX: The primary tumor cannot be assessed. T0: there is no evidence of tumor. T is: in situ carcinoma, no invasion. T1: The tumor is 2 cm or less. T2: The tumor is more than 2 cm but less than 5 cm. T3: The tumor is more than 5 cm. T4: Tumor of any size growing in the wall of the breast or skin, or inflammatory breast cancer.

NX: The nearby lymph nodes cannot be assessed. N0: The cancer has not spread to the regional lymph nodes. N1: The cancer has not spread to 1 to 3 axillary lymph nodes or to one internal mammary lymph node. N2: The cancer has spread to 4 to 9 axillary lymph nodes or to multiple internal mammary lymph nodes. N3: One of the followings applies:

The cancer has spread to 10 or more axillary lymph nodes, or the cancer has spread to the infraclavicular lymph nodes, or the cancer has spread to the supraclavicular lymph nodes or the cancer affects the axillary lymph nodes and has spread to the internal mammary lymph nodes, or the cancer affects 4 or more axillary lymph nodes and minimum amounts of cancer are in the internal mammary nodes or in sentinel lymph node biopsy.

MX: The presence of distant spread (metastasis) cannot be assessed. M0: There is no distant spread. M1: spreading to distant organs which do not include the supraclavicular lymph node has been produced.

The fact that most of the patients with solid tumor cancer die after metastasis means that it is crucial to understand the molecular and cellular mechanisms allowing a tumor to metastasize. Recent publications have demonstrated how the metastasis is caused by means of complex yet little known mechanisms and also how the different metastatic cell types have a tropism towards specific organs. These tissue specific metastatic cells have a series of acquired functions allowing them to colonize specific organs.

All cells have receptors on their surface, in their cytoplasm and the cell nucleus. Certain chemical messengers such as hormones bind to said receptors and this causes changes in the cell. There are three significant receptors which may affect the breast cancer cells: estrogen receptor (ER), progesterone receptor (PR) and HER2/neu. For the purpose of naming the cells having any of these receptors, a positive sign is placed thereto when the receptor is present and a negative sign if it is absence: ER positive (ER+), ER negative (ER−), PR+ (positive), PR negative (PR−), HER2+ (positive) and HER2 negative (HER2−). The receptor state has become a critical assessment for all breast cancers since it determines the suitability of using specific treatments, for example, tamoxifen or trastuzumab. The alpha isoform of the estrogen receptor (ER) is over-expressed in about 65% of the diagnosed cases of breast cancer. This type of breast cancer is referred to as "ER-positive" (ER+). In this case the binding of the estrogen to the ER stimulates the tumor mammary cell proliferation. The ER+ tumor cells are highly dependent on this stimulus to proliferate, therefore ER is currently used as a therapeutic target.

The keystone for treating breast cancer is surgery when the tumor is localized with possible adjuvant hormone therapy (with tamoxifen or an aromatase inhibitor), chemotherapy, and/or radiotherapy. Currently, the suggestions for treatment after the surgery (adjuvant therapy) follow a pattern. This pattern is subject to change because every two years, a world conference takes place in St. Gallen, Switzerland to discuss the actual results of the worldwide multicenter studies. Likewise, said pattern is also reviewed according to the consensus criterion of the National Institute of Health (NIH). Based on in these criteria, more than 85-90% of the patients not having metastasis in lymph nodes would be candidates to receive adjuvant systemic therapy.

Currently, PCR assays such as Oncotype DX or microarray assays such as MammaPrint can predict the risk of breast cancer relapse based on the expression of specific genes. In February 2007, the MammaPrint assay became the first breast cancer indicator in achieving official authorization from the Food and Drug Administration.

Patent application EP1961825-A1 describes a method for predicting the occurrence of breast cancer metastasis to bone, lung, liver or brain, which comprises determining in a tumor tissue sample the expression level of one or more markers with respect to their corresponding expression level in a control sample, among which include c-MAF. However, this document requires determining several genes simultaneously to enable determining the survival of breast cancer patients and the correlation between the capacity of the gene signature for predicting the survivability free from bone metastasis was not statistically significant.

Bos, P. D., et al. [Nature, 2009, 459:1005-1009] describes genes involved in the breast cancer metastasis to the brain.

Patent application US2005/0181375 describes methods for the detecting metastatic breast cancer based on detecting the expression levels of a series of genes which are randomly regulated or downregulated in metastatic tumors and particularly in tumors metastasizing to the brain.

International patent application WO2010/000907 describes a gene signature useful as genomic predictor for distal metastasis in breast cancer patients.

However, there are no genetic markers, in the state of the art, which allow the diagnosis and/or the prognosis of whether a patient who suffers a specific breast cancer, such as ER– or ER+ breast cancer, will or will not suffer metastasis, thus a suitable therapy being able to be applied to the subject suffering said cancer. Therefore, there is the need of identifying new markers which allow diagnosing the presence of metastasis in subjects suffering ER+ or ER– breast cancer and/or predicting the probability of a subject suffering ER+ or ER– breast cancer to develop metastasis. The identification of new prognosis factors will serve as a guide in selecting the most suitable treatments.

SUMMARY OF THE INVENTION

The authors of the present invention have identified and validated c-MAF as marker associated to a greater tendency of the ER+ breast cancer to cause metastasis and, particularly, bone metastasis. This over-expression is partly due to an amplification of the locus 16q22-q24 in which the c-MAF gene is located. Although it is not intended to be bound by any theory in particular, it is believed that the signaling pathway of the estrogen receptor (ER) contributes to breast cancer metastasis leading to the molecular events necessary for causing said metastasis.

The role of the c-MAF gene in ER+ breast cancer metastasis has been characterized by the inventors by means of inoculating the MCF7 cell line (human ER+ breast cancer cell line) into immunodeficient mice, to then obtain the expression profile associated to cell lines obtained from bone metastasis of said MCF7 cells. From said expression profile and by applying various criteria, the c-MAF gene was selected, variations in the expression levels predicting the recurrence of primary breast cancer tumors to bone being demonstrated. Subsequently, the c-MAF expression levels were studied in two different databases containing the expression profiles and the clinical notes of primary tumors from patients with breast cancer and of metastasis from breast cancer patients, the c-MAF gene expression correlates positively with different clinical parameters, included the recurrence and metastasis being observed. Additionally, the c-MAF expression levels in bone metastasis from breast cancer were determined, high c-MAF levels being observed in metastasis originating from ER+ and ER– tumors. Finally, the c-MAF gene was validated individually by means of in vivo metastasis colonization assay followed by gain-of-function experiments by means of lentiviral vectors and loss-of-function experiments by means of using interference RNA (siRNA). These studies have demonstrated the role of c-MAF as marker for prognosis and as a target gene in breast cancer metastasis, particularly, bone metastasis from the breast cancer. Likewise, the inventors have associated the amplification of the locus 16q22-q24, including the c-MAF gene, with the presence of metastasis in subjects with breast cancer and the amplification of the c-MAF gene in breast cancer cell lines with tendency to form bone metastasis.

Thus, in a first aspect, the invention relates to an in vitro method for the diagnosis of metastasis in a subject with ER+ breast cancer and/or the prognosis of the tendency to develop metastasis in a subject with ER+ breast cancer which comprises
  (i) quantifying the c-MAF gene expression level in a tumor tissue sample of said subject and
  (ii) comparing the expression level previously obtained with the expression level of said gene in a control sample, wherein if the expression levels of said gene are increased with respect to the expression levels of said gene in the control sample, then said subject has a positive diagnosis for metastasis or a greater tendency to develop metastasis.

In a second aspect, the invention relates to an in vitro method for designing a customized therapy for a subject with ER+ breast cancer which comprises
  (i) quantifying the c-MAF gene expression level in a tumor tissue sample of said subject and
  (ii) comparing the expression level previously obtained with the expression level of said gene in a control sample,
  wherein if the expression levels are increased with respect to the expression levels of said gene in the control sample, then said subject is susceptible to receive a therapy aiming to prevent an/or treat the metastasis.

In a third aspect, the invention relates to an in vitro method for designing a customized therapy for a subject with breast cancer with bone metastasis which comprises
  (i) quantifying the c-MAF gene expression level in a bone metastatic tumor tissue sample of said subject and
  (ii) comparing the expression level obtained in step (i) with the expression level of said gene in a control sample,
  wherein if the c-MAF gene expression levels are increased with respect to the expression levels of said gene in the control sample, then said subject is susceptible to receive a therapy aiming to prevent the bone degradation.

In a fourth aspect, the invention relates to an in vitro method for the diagnosis of metastasis in a subject with breast cancer and/or for the prognosis of the tendency to develop metastasis in a subject with breast cancer which comprises determining if the c-MAF gene is amplified in a tumor tissue sample of said subject; wherein if said gene is amplified with respect to a control sample, then said subject has a positive diagnosis for metastasis or a greater tendency to develop metastasis.

In a fifth aspect, the invention relates to the use of a c-MAF inhibitory agent in the preparation of a medicinal product for treating and/or preventing breast cancer metastasis.

In a final aspect, the invention relates to the use of an agent capable of avoiding or preventing bone degradation in the preparation of a medicinal product for the treatment of bone metastasis in a subject suffering breast cancer and having elevated c-MAF levels in a metastatic tumor tissue sample with respect to a control sample.

DETAILED DESCRIPTION OF THE INVENTION

Figure 1A:
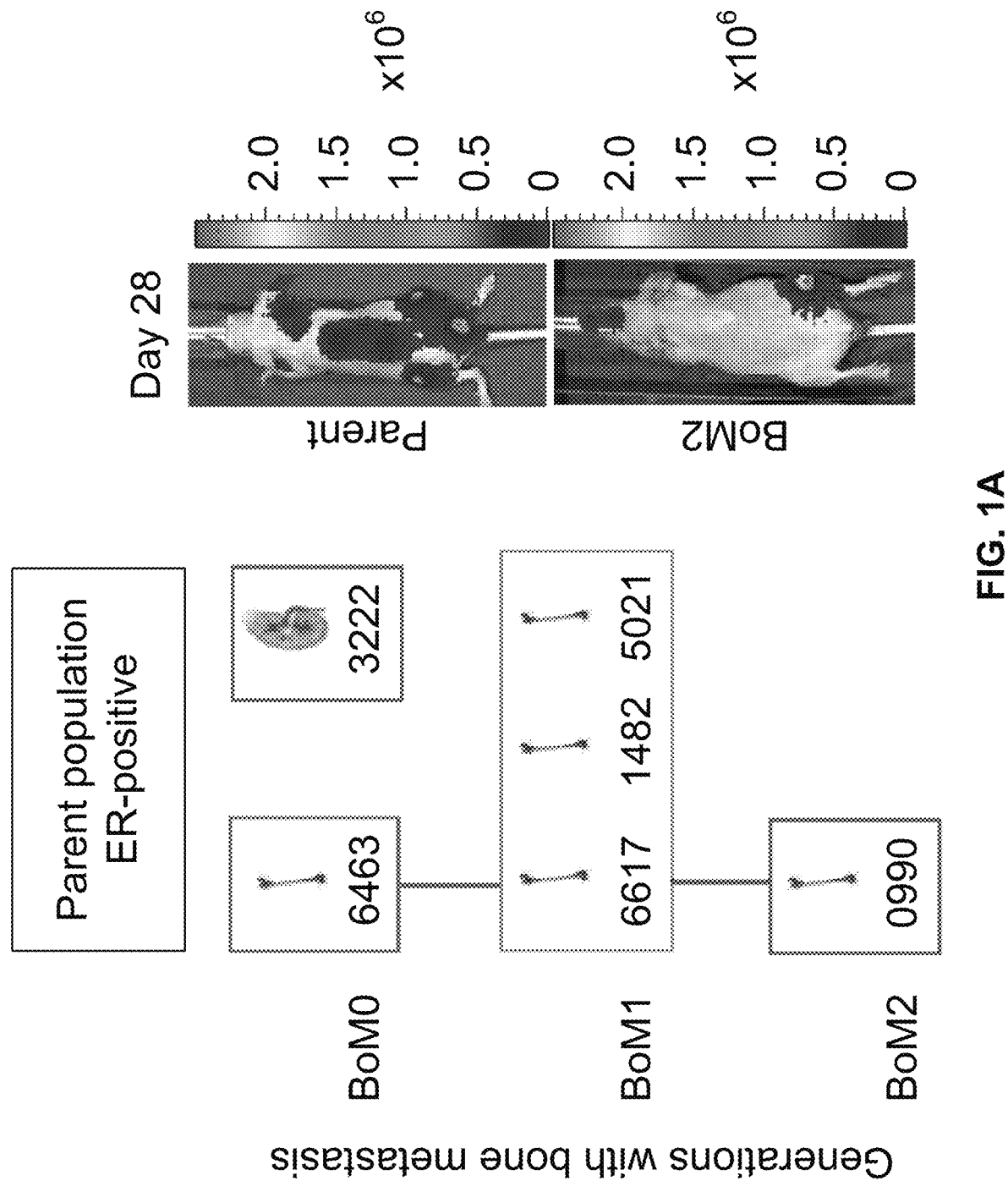
FIG. 1(A) shows the graphic depiction of the in vivo selection process of the tissue-specific metastatic subpopulations. Each of the subsequent bone metastatic generations is designated as BoM0, BoM1 and BoM2. The metastatic capacity of these cell types was analyzed by means of intra-cardiac injection in a graft model in immunosuppressed mouse.

Methods for the Diagnosis and Prognosis of Breast Cancer Metastasis Based on C-MAF Expression Levels The inventors have shown that the c-MAF gene is overexpressed in breast cancer metastasis particularly in ER+ tumors, and that the c-MAF expression levels in primary tumors are correlated to different clinical parameters of breast cancer, particularly with recurrence and metastasis probability. Thus, as seen in the examples of the present invention (see Example 2), c-MAF overexpression is correlated with the onset of ER+ breast tumor metastasis in bone (see FIG. 1). Therefore, c-MAF can be used as a marker for the diagnosis and/or prognosis of metastasis in a subject with ER+ breast cancer.

Thus in one aspect, the invention relates to an in vitro method for the diagnosis of metastasis in a subject with ER+ breast cancer and/or for the prognosis of the tendency to develop metastasis in a subject with ER+ breast cancer (hereinafter first method of the invention) which comprises
 (i) quantifying the c-MAF gene expression level in a tumor tissue sample from said subject and
 (ii) comparing the expression level previously obtained with the expression level of said gene in a control sample,
 wherein if the expression levels of said gene are increased with respect to the expression levels of said gene in the control sample, then said subject has a positive diagnosis for metastasis or a greater tendency to develop metastasis.

The c-MAF gene (v-maf musculoaponeurotic fibrosarcoma oncogene homologue (avian) also known as MAF or MGC71685) is a transcription factor containing a leucine zipper which acts like a homodimer or a heterodimer. Depending on the DNA binding site, the encoded protein can be a transcriptional activator or repressor. The DNA sequence encoding c-MAF is described in the NCBI database under accession number NG_016440 (SEQ ID NO: 1). Two messenger RNA are transcribed from said DNA sequence, each of the which will give rise to one of the two c-MAF protein isoforms, the α isoform and the β isoform. The complementary DNA sequences for each of said isoforms are described, respectively, in the NCBI database under accession numbers NM_005360.4 (SEQ ID NO: 2) and NM_001031804.2 (SEQ ID NO: 3).

In the context of the present invention, "metastasis" is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a breast cancer, for example, spreads (metastasizes) to the lung, the secondary tumor is formed of malignant breast cancer cells. The disease in the lung is metastatic breast cancer and not lung cancer. In a particular embodiment of the method of the invention, the metastasis is ER+ breast cancer which has spread (metastasized) to the bone.

In the present invention, "ER+ breast cancer" is understood as breast cancer the tumor cells of which express the estrogen receptor (ER). This makes said tumors sensitive to estrogens, meaning that the estrogen makes the cancerous breast tumor grow. In contrast, "ER− breast cancer" is understood as breast cancer the tumor cells of which do not express the estrogen receptor (ER).

In the present invention, "diagnosis of metastasis in a subject with breast cancer" is understood as identifying a disease (metastasis) by means of studying its signs, i.e., in the context of the present invention by means of increased c-MAF gene expression levels (i.e., overexpression) in the breast cancer tumor tissue with respect to a control sample. In the present invention "prognosis of the tendency to develop metastasis in a subject with ER+ breast cancer" is understood as knowing based on the signs if the ER+ breast cancer that said subject has will metastasize in the future. In the context of the present invention, the sign is c-MAF gene overexpression in tumor tissue.

The method of the invention comprises in a first step quantifying the c-MAF gene expression level in a tumor tissue sample from a subject.

In a preferred embodiment, the first method of the invention comprises quantifying only the c-MAF gene expression level as a single marker, i.e., the method does not involve determining the expression level of any additional marker.

As used herein, the term "subject" or "patient" refers to all animals classified as mammals and includes but is not limited to domestic and farm animals, primates and humans, for example, human beings, non-human primates, cows, horses, pigs, sheep, goats, dogs, cats, or rodents. Preferably, the subject is a human man or woman of any age or race.

In the present invention "tumor tissue sample" is understood as the tissue sample originating from the primary ER+ breast cancer tumor. Said sample can be obtained by conventional methods, for example biopsy, using methods well known by the persons skilled in related medical techniques. The methods for obtaining a biopsy sample include splitting a tumor into large pieces, or microdissection, or other cell separating methods known in the art. The tumor cells can additionally be obtained by means of cytology through aspiration with a small gauge needle. To simplify sample preservation and handling, samples can be fixed in formalin and soaked in paraffin or first frozen and then soaked in a tissue freezing medium such as OCT compound by means of immersion in a highly cryogenic medium which allows rapid freezing.

As understood by the person skilled in the art, the gene expression levels can be quantified by measuring the messenger RNA levels of said gene or of the protein encoded by said gene.

For this purpose, the biological sample can be treated to physically or mechanically break up the tissue or cell structure, releasing the intracellular components into an aqueous or organic solution for preparing nucleic acids. The nucleic acids are extracted by means of commercially available methods known by the person skilled in the art (Sambroock, J., et al., "Molecular cloning: a Laboratory Manual", 3rd ed., Cold Spring Harbor Laboratory Press, N.Y., Vol. 1-3.)

Thus, the c-MAF gene expression level can be quantified from the RNA resulting from the transcription of said gene (messenger RNA or mRNA) or, alternatively, from the complementary DNA (cDNA) of said gene. Therefore, in a particular embodiment of the invention, the quantification of the c-MAF gene expression levels comprises the quantification of the messenger RNA of the c-MAF gene or a fragment of said mRNA, complementary DNA of the c-MAF gene or a fragment of said cDNA or the mixtures thereof.

Virtually any conventional method can be used within the scope of the invention for detecting and quantifying the mRNA levels encoded by the c-MAF gene or of the corresponding cDNA thereof. By way of non-limiting illustration, the mRNA levels encoded by said gene can be quantified using conventional methods, for example, methods comprising mRNA amplification and the quantification of said mRNA amplification product, such as electrophoresis and staining, or alternatively, by Southern blot and using suitable probes, Northern blot and using specific probes of the mRNA of the gene of interest (c-MAF) or of the corresponding cDNA thereof, mapping with S1 nuclease, RT-PCR, hybridization, microarrays, etc., preferably by means of real time quantitative PCR using a suitable marker. Likewise, the cDNA levels corresponding to said mRNA encoded by the c-MAF gene can also be quantified by means of using conventional techniques; in this case, the method of the invention includes a step for synthesizing the corresponding cDNA by means of reverse transcription (RT) of the corresponding mRNA followed by the amplification and quantification of said cDNA amplification product. Conventional methods for quantifying expression levels can be found, for example, in Sambrook et al., 2001. (cited ad supra).

In a particular embodiment, the c-MAF gene expression levels are quantified by means of quantitative polymerase chain reaction (PCR) or a DNA or RNA array.

In addition, the c-MAF gene expression level can also be quantified by means of quantifying the expression levels of the protein encoded by said gene, i.e., the c-MAF protein (c-MAF) [NCBI, accession number 075444], or any functionally equivalent variant of the c-MAF protein. There are two c-MAF protein isoforms, the α isoform (NCBI, NP 005351.2) made up of 403 amino acids (SEQ ID NO: 4) and the β isoform (NP_001026974.1) made up of 373 amino acids (SEQ ID NO: 5). The c-MAF gene expression level can be quantified by means of quantifying the expression levels of any of the c-MAF protein isoforms. Thus, in a particular embodiment, the quantification of the levels of the protein encoded by the c-MAF gene comprises the quantification of the c-MAF protein.

In the context of the present invention, "functionally equivalent variant of the c-MAF protein" is understood as (i) variants of the c-MAF protein (SEQ ID NO: 4 or SEQ ID NO: 5) in which one or more of the amino acid residues are substituted by a conserved or non-conserved amino acid residue (preferably a conserved amino acid residue), wherein such substituted amino acid residue may or may not be one encoded by the genetic code, or (ii) variants comprising an insertion or a deletion of one or more amino acids and having the same function as the c-MAF protein, i.e., to act as a DNA binding transcription factor. Variants of the c-MAF protein can be identified using methods based on the capacity of c-MAF for promoting in vitro cell proliferation as shown in international patent application WO2005/046731, based on the capacity of the so-called inhibitor for blocking the transcription capacity of a reporter gene under the control of cyclin D2 promoter or of a promoter containing the c-MAF responsive region (MARE or c-MAF responsive element) in cells expressing c-MAF as described in WO2008098351, or based on the capacity of the so-called inhibitor for blocking reporter gene expression under the control of the IL-4 promoter in response to the stimulation with PMA/ionomycin in cells expressing NFATc2 and c-MAF as described in US2009048117A.

The variants according to the invention preferably have sequences similarity with the amino acid sequence of any of the c-MAF protein isoforms (SEQ ID NO: 4 or SEQ ID NO: 5) of at least 50%, at least 60%, at least 70%, at least 80%, at least 90%, at least 91%, at least 92%, at least 93%, at least 94%, at least 95%, at least 96%, at least 97%, at least 98% or at least 99%. The degree of similarity between the variants and the specific c-MAF protein sequences defined previously is determined using algorithms and computer processes which are widely known by the persons skilled in the art. The similarity between two amino acid sequences is preferably determined using the BLASTP algorithm [BLAST Manual, Altschul, S., et al., NCBI NLM NIH Bethesda, Md. 20894, Altschul, S., et al., J. Mol. Biol. 215: 403-410 (1990)].

The c-MAF protein expression level can be quantified by any conventional method which allows detecting and quantifying said protein in a sample from a subject. By way of non-limiting illustration, said protein levels can be quantified, for example, by using antibodies with c-MAF binding capacity (or a fragment thereof containing an antigenic determinant) and the subsequent quantification of the complexes formed. The antibodies used in these assays may or may not be labeled. Illustrative examples of markers that can be used include radioactive isotopes, enzymes, fluorophores, chemiluminescence reagents, enzyme substrates or cofactors, enzyme inhibitors, particles, dyes, etc. There is a wide range of known assays that can be used in the present invention which use unlabeled antibodies (primary antibody) and labeled antibodies (secondary antibody); these techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks. Other ways for detecting and quantifying said c-MAF protein include affinity chromatography techniques, ligand binding assays, etc. When an immunological method is used, any antibody or reagent that is known to bind to the c-MAF protein with a high affinity can be used for detecting the amount thereof. Nevertheless, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies and antibodies. There are commercial anti-c-MAF protein antibodies on the market which can be used in the context of the present invention, such as for example antibodies ab427, ab55502, ab55502, ab72584, ab76817, ab77071 (Abcam plc, 330 Science Park, Cambridge CB4 OFL, United Kingdom), the O75444 monoclonal antibody (Mouse Anti-Human MAF Azide free Monoclonal antibody, Unconjugated, Clone 6b8) of AbD Serotec, etc. There are many commercial companies offering anti-c-MAF antibodies, such as Abnova Corporation, Bethyl Laboratories, Bioworld Technology, GeneTex, etc.

In a particular embodiment, the c-MAF protein levels are quantified means of western blot, ELISA or a protein array.

The first method of the invention comprises in a second step comparing the c-MAF gene expression level obtained in the tumor sample from the subject with the expression level of said gene in a control sample.

Once the c-MAF gene expression levels in a tumor tissue sample from a subject with ER+ breast cancer have been measured and compared with the control sample, if the expression levels of said gene are increased with respect to its expression levels in the control sample, then it can be concluded that said subject has a positive diagnosis for metastasis or a greater tendency to develop metastasis.

The determination of the c-MAF gene expression levels must be correlated with values of a control sample or reference sample. Depending on the type of tumor to be analyzed, the exact nature of the control sample may vary. Thus, in the event that a diagnosis is to be evaluated, then the reference sample is a tumor tissue sample from a subject with ER+ breast cancer that has not metastasized or that corresponds to the median value of the c-MAF gene expression levels measured in a tumor tissue collection in biopsy samples from subjects with ER+ breast cancer which have not metastasized.

Said reference sample is typically obtained by combining equal amounts of samples from a subject population. Generally, the typical reference samples will be obtained from subjects who are clinically well documented and in whom the absence of metastasis is well characterized. In such samples, the normal concentrations (reference concentration) of the biomarker (c-MAF gene) can be determined, for example by providing the mean concentration over the reference population. Various considerations are taken into account when determining the reference concentration of the marker. Among such considerations are the age, weight, sex, general physical condition of the patient and the like. For example, equal amounts of a group of at least 2, at least 10, at least 100 to preferably more than 1000 subjects, preferably classified according to the foregoing considerations, for example according to various age categories, are taken as the reference group. The sample collection from which the reference level is derived will preferably be formed by subjects suffering from the same type of cancer as the patient object of the study.

Once this median value has been established, the level of this marker expressed in tumor tissues from patients with this median value can be compared and thus be assigned to the "increased" expression level. Due to the variability among subjects (for example, aspects referring to age, race, etc.) it is very difficult (if not virtually impossible) to established absolute reference values of c-MAF expression. Thus, in particular embodiment the reference values for "increased" or "reduced" expression of the c-MAF expression are determined by calculating the percentiles by conventional means which involves performing assays in one or several samples isolated from subjects whose disease is well documented by any of the methods mentioned above the c-MAF expression levels. The "reduced" levels of c-MAF can then preferably be assigned to samples wherein the c-MAF expression levels are equal to or lower than 50th percentile in the normal population including, for example, expression levels equal to or lower than the 60th percentile in the normal population, equal to or lower than the 70th percentile in the normal population, equal to or lower than the 80th percentile in the normal population, equal to or lower than the 90th percentile in the normal population, and equal to or lower than the 95th percentile in the normal population. The "increased" c-MAF gene expression levels can then preferably be assigned to samples wherein the c-MAF gene expression levels are equal to or greater than the 50th percentile in the normal population including, for example, expression levels equal to or greater than the 60th percentile in the normal population, equal to or greater than the 70th percentile in the normal population, equal to or greater than the 80th percentile in the normal population, equal to or greater than the 90th percentile in the normal population, and equal to or greater than the 95th percentile in the normal population.

In the present invention "increased expression levels" is understood as the expression level when it refers to the levels of the c-MAF gene greater than those in a reference sample or control sample. Particularly, a sample can be considered to have high c-MAF expression levels when the expression levels in the reference sample are at least 1.1 times, 1.5 times, 5 times, 10 times, 20 times, 30 times, 40 times, 50 times, 60 times, 70 times, 80 times, 90 times, 100 times or even more with respect to the sample isolated from the patient.

In the context of the present invention, it is understood that "a subject has a positive diagnosis for metastasis" when the ER+ breast cancer suffered by said subject has metastasized to other organs of the body, in a particular embodiment, to the bone.

In a yet more preferred embodiment, the metastasis to bone is an osteolytic bone metastasis. As used herein, the expression "osteolytic bone metastasis" refers to a type of metastasis in which bone resorption (progressive loss of the bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

On the other hand, it is understood in the present invention that "a subject has a greater tendency to develop metastasis" when the probabilities that the ER+ breast cancer suffered by the subject will metastasize in the future are high.

The person skilled in the art will understand that the prediction of the tendency for a primary breast tumor to metastasize is not intended to be correct for all the subjects to be identified (i.e., for 100% of the subjects). Nevertheless, the term requires enabling the identification of a statistically significant part of the subjects (for example, a cohort in a cohort study). Whether a part is statistically significant can be determined in a simple manner by the person skilled in the art using various well known statistical evaluation tools, for example, the determination of confidence intervals, determination of p values, Student's T test, Mann-Whitney test, etc. Details are provided in Dowdy and Wearden, Statistics for Research, John Wiley and Sons, New York 1983. The preferred confidence intervals are at least 90%, at least 95%, at least 97%, at least 98% or at least 99%. The p values are preferably 0.1, 0.05, 0.01, 0.005 or 0.0001. More preferably, at least 60%, at least 70%, at least 80% or at least 90% of the subjects of a population can be suitably identified by the method of the present invention.

Method for Designing Customized Therapy of the Invention in Patients with ER+ Breast Tumors As is known in the state of the art, the treatment to be administered to a subject suffering from cancer depends on whether the latter is a malignant tumor, i.e., whether it has high probabilities of undergoing metastasis, or whether the latter is a benign tumor. In the first assumption, the treatment of choice is a systemic treatment such as chemotherapy and in the second assumption, the treatment of choice is a localized treatment such as radiotherapy.

Therefore, as described in the present invention, given that the c-MAF gene overexpression in breast cancer cells is related to the presence of metastasis, the c-MAF gene expression levels allow making decisions in terms of the most suitable therapy for the subject suffering said cancer.

Thus, in another aspect the invention relates to an in vitro method for designing a customized therapy for a subject with ER+ breast cancer, hereinafter second method of the invention, which comprises
 (i) quantifying the c-MAF gene expression level in a tumor tissue sample of said subject and
 (ii) comparing the expression level previously obtained with the expression level of said gene in a control sample,
 wherein if the expression levels are increased with respect to the expression levels of said gene in the control sample, then said subject is susceptible to receive a therapy aiming to prevent and/or treat the metastasis.

In a particular embodiment, the metastasis is a bone metastasis. In a more preferred embodiment, the bone metastasis is osteolytic metastasis.

The terms and expressions "subject", "ER+ breast cancer", "tumor tissue sample", "metastasis", "determination of expression levels", "c-MAF gene", "increased expression levels" and "control sample" have been described in detail in relation to the first method of the invention and are equally applicable to the second and third method of the invention.

The second method of the invention comprises in a first step quantifying the c-MAF gene expression level in a tumor tissue sample in a subject suffering from ER+ breast cancer.

In a preferred embodiment, the second method of the invention comprises quantifying only the c-MAF gene expression level as a single marker, i.e., the method does not involve determining the expression level of any additional marker.

In the case of the second method of the invention the sample is a primary tumor tissue sample of the subject. In a second step, the c-MAF gene expression level obtained in the tumor sample of the subject is compared with the expression level of said gene in a control sample. The determination of the c-MAF gene expression levels must be related to values of a control sample or reference sample. Depending on the type of tumor to be analyzed, the exact nature of the control sample may vary. Thus preferably the reference sample is a tumor tissue sample of subject with ER+ breast cancer that has not metastasized or that correspond to the median value of the c-MAF gene expression levels measured in a tumor tissue collection in biopsy samples of subjects with ER+ breast cancer which has not metastasized.

Once the c-MAF gene expression levels in the sample have been measured and compared with the control sample, if the expression levels of said gene are increased with respect to their expression levels in the control sample, then it can be concluded that said subject is susceptible to receiving therapy aiming to prevent (if the subject has yet to undergo metastasis) and/or treat metastasis (if the subject has already experienced metastasis).

When the cancer has metastasized, systemic treatments including but not limited to chemotherapy, hormone treatment, immunotherapy, or a combination thereof are used. Additionally, radiotherapy and/or surgery can be used. The choice of treatment generally depends on the type of primary cancer, the size, the location of the metastasis, the age, the general health of the patient and the types of treatments used previously.

The systemic treatments are those that reach the entire body:
  Chemotherapy is the use of medicaments to destroy cancer cells. The medicaments are generally administered through oral or intravenous route. Sometimes, chemotherapy is used together with radiation treatment.
  Hormone therapy is based on the fact that some hormones promote of some cancer growth. For example, estrogen in women produced by the ovaries sometimes promotes the breast cancer growth. There are several ways for stopping the production of these hormones. A way is to remove the organs producing them: the ovaries in the case of women, the testicles in the case of the men. More frequently, medicaments to prevent these organs from producing the hormones or to prevent the hormones from acting on the cancer cells can be used.
  Immunotherapy is a treatment that aids the immune system itself of the patient to combat cancer. There are several types of immunotherapy which are used to treat metastasis patients. These include but are not limited to cytokines, monoclonal antibodies and antitumor vaccines.

Method for Designing Customized Therapy of the Invention in Breast Cancer Patients with Bone Metastasis The authors of the present invention have clearly shown that the conditioned medium of cell lines derived from primary breast tumors which have high bone metastasis causing capacity and which over-express c-MAF are capable of inducing the osteoclast formation in a greater extent than the cells that do not over-express c-MAF. Thus, those patients suffering ER– breast cancer which has already metastasized to the bone and in which there are elevated c-MAF levels may particularly benefit from therapies aimed at preventing the bone degradation caused by the increased osteoclastic activity.

Thus, in another aspect, the invention relates to an in vitro method for designing a customized therapy for a subject with ER– breast cancer with bone metastasis (hereinafter third method of the invention) which comprises
  (i) quantifying the c-MAF gene expression level in a metastatic tumor tissue sample from bone of said subject and
  (ii) comparing the expression level previously obtained with the expression level of said gene in a control sample,
wherein if the expression levels are increased with respect to the expression levels of said gene in the control sample, then said subject is susceptible to receive a therapy aiming to prevent the bone degradation.

The terms and expressions "subject", "ER+ breast cancer", "tumor tissue sample", "metastasis", "determination of expression levels", "c-MAF gene", "increased expression levels" and "control sample" have been described in detail in relation to the first method of the invention and are equally applicable to the second and third method of the invention.

In a preferred embodiment, the bone metastasis is osteolytic metastasis.

The third method of the invention comprises in a first step, quantifying the c-MAF gene expression level in a tumor tissue sample in a subject suffering breast cancer. In the case of the third method of the invention, the sample is a tissue sample from bone metastasis.

In a preferred embodiment, the third method of the invention comprises quantifying only the c-MAF gene expression level as a single marker, i.e., the method does not involve determining the expression level of any additional marker.

In a second step the c-MAF gene expression level obtained in the tumor sample of the subject is compared with the expression level of said gene in a control sample. The determination of the c-MAF gene expression levels must be correlated to values of a control sample or reference sample. Depending on the type of tumor to be analyzed, the exact nature of the control sample may vary. Thus, in the case involving the third method of the invention, then the reference sample is a tumor tissue sample of subject with breast cancer who has not suffered metastasis or that correspond to the median value of the c-MAF gene expression levels measured in a tumor tissue collection in biopsy samples of subjects with breast cancer who has not suffered metastasis.

Once the c-MAF gene expression levels in the sample is measured and compared with the control sample, if the expression levels of said gene are increased with respect to its expression levels in the control sample, then it can be concluded that said subject is susceptible to receive a therapy aiming to avoid or prevent bone degradation.

As used herein, an "agent for avoiding or preventing bone degradation" refers to any molecule capable of treating or stopping bone degradation either by stimulating the osteoblast proliferation or inhibiting the osteoclast proliferation. Illustrative examples of agents used for avoiding and/or preventing bone degradation include, although not limited to:
  Parathyroid hormone (PTH) or recombinant forms thereof (teriparatide corresponding to the amino acids 1-34 of PTH). This hormone acts by stimulating the osteoblasts and increasing their activity.
  Strontium ranelate: is an alternative oral treatment, and forms part of the group of drugs called "dual action bone agents" (DABAs) because they stimulate the osteoblast proliferation and inhibit the osteoclast proliferation.
  "Estrogen receptor modulators" (SERM) refers to compounds which interfere or inhibit the binding of estrogens to the receptor, regardless of the mechanism. Examples of estrogen receptor modulators include, among others, estrogens progestagen, estradiol, droloxifene, raloxifene, lasofoxifene, TSE-424, tamoxifen, idoxifene, L Y353381, LY117081, toremifene, fluvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate 4,4'dihydroxybenzophenone-2,4-dinitrophenyl-hydrazone and SH646.

Calcitonin: directly inhibits the osteoclast activity through the calcitonin receptor. The calcitonin receptors have been identified on the surface of the osteoclasts.

Bisphosphonates: are a group of medicinal products used for the prevention and the treatment of diseases with bone resorption and reabsorption such as osteoporosis and cancer with bone metastasis, the latter being with or without hypercalcaemia, associated to breast cancer and prostate cancer. Examples of bisphosphonates which cane be used in the therapy designed by means of the third method of the invention include, although not limited to, nitrogenous bisphosphonates (such as pamidronate, neridronate, olpadronate, alendronate, ibandronate, risedronate, incadronate, zoledronate or zoledronic acid, etc.) and non-nitrogenous bisphosphonates (such as etidronate, clodronate, tiludronate, etc.).

"Cathepsin K inhibitors" refers to compounds which interfere in the cathepsin K cysteine protease activity. Non-limiting examples of cathepsin K inhibitors include 4-amino-pyrimidine-2-carbonitrile derivatives (described in the International patent application WO 03/020278 under the name of Novartis Pharma GMBH), pyrrolo-pyrimidines described in the publication WO 03/020721 (Novartis Pharma GMBH) and the publication WO 04/000843 (ASTRAZENECA AB) as well as the inhibitors described in the publications PCT WO 00/55126 of Axys Pharmaceuticals, WO 0/49288 of Merck Frosst Canada & Co. and Axys Pharmaceuticals.

"RANKL inhibitors" as used herein refers to any compound which is capable of reducing the RANK activity. RANKL is found on the surface of the osteoblast membrane of the stroma and T-lymphocyte cells, and these T-lymphocyte cells are the only ones which have demonstrated the capacity for secreting it. Its main function is the activation of the osteoclasts, cells involved in the bone resorption. The RANKL inhibitors can act by blocking the binding of RANKL to its receptor (RANK), blocking the RANK-mediated signaling or reducing the expression of RANKL by blocking the transcription or the translation of RANKL. RANKL antagonists or inhibitors suitable for use in the present invention include, without limitation:
  a suitable RANK protein which is capable of binding RANKL and which comprises the entire or a fragment of the extracellular domain of a RANK protein. The soluble RANK may comprise the signal peptide and the extracellular domain of the murine or human RANK polypeptides, or alternatively, the mature form of the protein with the signal peptide removed can be used.
  Osteoprotegerin or a variant thereof with RANKL-binding capacity.
  RANKL-specific antisense molecules
  Ribozymes capable of processing the transcribed products of RANKL
  Specific anti-RANKL antibodies. "Anti-RANKL antibody or antibody directed against RANKL" is understood herein as all that antibody which is capable of binding specifically to the ligand of the activating receptor for the nuclear factor κB (RANKL) inhibiting one or more RANKL functions. The antibodies can be prepared using any of the methods which are known by the person skilled in the art. Thus, the polyclonal antibodies are prepared by means of immunizing an animal with the protein to be inhibited. The monoclonal antibodies are prepared using the method described by Kohler, Milstein et al. (Nature, 1975, 256: 495).

Antibodies suitable in the context of the present invention include intact antibodies which comprises a variable antigen binding region and a constant region, fragments "Fab", "F(ab')2" and "Fab'", Fv, scFv, diabodies and bispecific antibodies.

In a preferred embodiment, the anti-RANKL antibody is a monoclonal antibody. In a yet more preferred embodiment, the anti-RANKL antibody is Denosumab (Pageau, Steven C. (2009). mAbs 1 (3): 210-215, CAS number 615258-40-7). In the context of the present invention, Denosumab is a monoclonal antibody which binds to RANKL and prevents its activation (it does not bind to the RANK receptor).

In a preferred embodiment, the agent preventing the bone degradation is a bisphosphonate. In a yet more preferred embodiment, the bisphosphonate is the zoledronic acid.

Alternatively a combined treatment can be carried out in which more than one agent from those mentioned above are combined to treat and/or prevent the metastasis or said agents can be combined with other supplements, such as calcium or vitamin D or with a hormone treatment.

Method of Diagnosis or Prognosis of Metastasis in Breast Cancer Based on Detecting the Amplification of the C-MAF Gene The authors of the invention have identified which cell lines derived from ER+ breast tumors having a high metastatic capacity show an amplification of the locus 16q22-q24, which includes the locus corresponding to the c-MAF gene and an amplification of the c-MAF gene.

Thus, in one aspect, the invention relates to an in vitro method for the diagnosis of metastasis in a subject with breast cancer (hereinafter, fourth diagnosis method of the invention) and/or for the prognosis of the tendency to develop metastasis in a subject with breast cancer which comprises determining if the c-MAF gene is amplified in a tumor tissue sample of said subject; wherein if said gene is amplified with respect to a control sample, then said subject has a positive diagnosis for metastasis or a greater tendency to develop metastasis.

In a particular embodiment, the breast cancer diagnosed in the fourth method of the invention is ER+ or ER− breast cancer.

The terms "c-MAF gene", "metastasis", "tumor tissue sample", "ER+ breast cancer", "diagnosis of metastasis in a subject with ER+ breast cancer", "prognosis of the tendency to develop metastasis in a subject with ER+ breast cancer", "subject", "patient", "subject having a positive diagnosis of metastasis", "subject having a greater tendency to develop metastasis" have been described in detail in the context of the first method of the invention and are equally applicable to the fourth method of the invention.

In a particular embodiment, the degree of amplification of the c-MAF gene can be determined by means of determining the amplification of a chromosome region containing said gene. Preferably, the chromosome region the amplification of which is indicative of the existence of amplification of the c-MAF gene is the locus 16q22-q24 which includes the c-MAF gene. The locus 16q22-q24 is located in chromosome 16, in the long arm of said chromosome and in a range between band 22 and band 24. This region corresponds in the NCBI database with the contigs NT_010498.15 and NT_010542.15. In another preferred embodiment, the degree of amplification of the c-MAF gene can be determined by means of using a probe specific for said gene.

The fourth diagnosis/prognosis method of the invention comprises, in a first step, determining if the c-MAF gene is amplified in a tumor tissue sample of a subject. To that end, the amplification of the c-MAF gene in the tumor sample is compared with respect to a control sample.

The term "amplification of a gene" as understood herein refers to a process through which various copies of a gene or of a gene fragment are formed in an individual cell or a cell line. The copies of the gene are not necessarily located in the same chromosome. The duplicated region is often called an "amplicon". Normally, the amount of mRNA produced, i.e., the gene expression level also increases in proportion to the copy number of a particular gene.

In a particular embodiment, the fourth method of the invention for the diagnoses of metastasis in a subject with breast cancer and/or for the prognosis of the tendency to develop metastasis in a subject with breast cancer, comprises determining the c-MAF gene copy number in a tumor tissue sample of said subject and comparing said copy number with the copy number of a control or reference sample, wherein if the c-MAF copy number is greater with respect to the c-MAF copy number of a control sample, then the subject has a positive diagnosis of metastasis or a greater tendency to develop metastasis.

The control sample refers to a tumor tissue sample of a subject with ER+ or ER– breast cancer (according to the type of cancer that the subject suffers from) who has not suffered metastasis or that correspond to the median value of the c-MAF gene copy number measured in a tumor tissue collection in biopsy samples of subjects with ER+ or ER– breast cancer who have not suffered metastasis. Said reference sample is typically obtained by combining equal amounts of samples from a subject population. If the c-MAF gene copy number is increased with respect to the copy number of said gene in the control sample, then subject has a positive diagnosis for metastasis or a greater tendency to develop metastasis.

As used herein, the term "gene copy number" refers to the copy number of a nucleic acid molecule in a cell. The gene copy number includes the gene copy number in the genomic (chromosomal) DNA of a cell. In a normal cell (non-tumoral cell), the gene copy number is normally two copies (one copy in each member of the chromosome pair). The gene copy number sometimes includes half of the gene copy number taken from samples of a cell population.

In the present invention, "increased gene copy number" is understood as when the c-MAF gene copy number is more than the copy number that a reference sample or control sample has. In particular, it can be considered that a sample has an increased c-MAF copy number when the copy number is more than 2 copies, for example, 3, 4, 5, 6, 7, 8, 9 or 10 copies, and even more than 10 copies of the c-MAF gene.

In a particular embodiment, the amplification or the copy number is determined by means of in situ hybridization or PCR.

Methods for determining whether the c-MAF gene or the chromosome region 16q22-q24 is amplified are widely known in the state of the art. Said methods include, without limitation, in situ hybridization (ISH) (such as fluorescence in situ hybridization (FISH), chromogenic in situ hybridization (CISH) or silver in situ hybridization (SISH)), genomic comparative hybridization or polymerase chain reaction (such as real time quantitative PCR). For any ISH method, the amplification or the copy number can be determined by counting the number of fluorescent points, colored points or points with silver in the chromosomes or in the nucleus.

The fluorescence in situ hybridization (FISH) is a cytogenetic technique which is used for detecting and locating the presence or absence of specific DNA sequences in chromosomes. FISH uses fluorescence probes which only bind to some parts of the chromosome with which they show a high degree of sequence similarity. In a typical FISH method, the DNA probe is labeled with a fluorescent molecule or a hapten, typically in the form of fluor-dUTP, digoxigenin-dUTP, biotin-dUTP or hapten-dUTP which is incorporated in the DNA using enzymatic reactions, such as nick translation or PCR. The sample containing the genetic material (the chromosomes) is placed on glass slides and is denatured by a formamide treatment. The labeled probe is then hybridized with the sample containing the genetic material under suitable conditions which will be determined by the person skilled in the art. After the hybridization, the sample is viewed either directly (in the case of a probe labeled with fluorine) or indirectly (using fluorescently labeled antibodies to detect the hapten).

In the case of CISH, the probe is labeled with digoxigenin, biotin or fluorescein and is hybridized with the sample containing the genetic material in suitable conditions.

Any marking or labeling molecule which can bind to a DNA can be used to label the probes used in the fourth method of the invention, thus allowing the detection of nucleic acid molecules. Examples of labels for the labeling include, although not limited to, radioactive isotopes, enzyme substrates, cofactors, ligands, chemiluminescence agents, fluorophores, haptens, enzymes and combinations thereof. Methods for labeling and guideline for selecting suitable labels for different purposes can be found, for example, in Sambrook et al. (Molecular Cloning: A Laboratory Manual, Cold Spring Harbor, New York, 1989) and Ausubel et al. (In Current Protocols in Molecular Biology, John Wiley and Sons, New York, 1998).

Once the existence of amplification is determined, either by directly determining the amplification of the c-MAF gene or by determining the amplification of the locus 16q22-q24, and after being compared with the amplification of said gene in the control sample, if amplification in the c-MAF gene is detected, it is indicative of the fact that the subject has a positive diagnosis for metastasis or a greater tendency to develop metastasis.

The determination of the amplification of the c-MAF gene needs to be correlated with values of a control sample or reference sample that correspond to the level of amplification of the c-MAF gene measured in a tumor tissue sample of a subject with breast cancer who has not suffered metastasis or that correspond to the median value of the amplification of the c-MAF gene measured in a tumor tissue collection in biopsy samples of subjects with breast cancer who have not suffered metastasis. Said reference sample is typically obtained by combining equal amounts of samples from a subject population. In general, the typical reference samples will be obtained from subjects who are clinically well documented and in whom the absence of metastasis is well characterized. The sample collection from which the reference level is derived will preferably be made up of subjects suffering the same type of cancer as the patient object of the study. Once this median value has been established, the level of amplification of c-MAF in tumor tissues of patients can be compared with this median value, and thus, if there is amplification, the subject has a positive diagnosis of metastasis or a greater tendency to develop metastasis.

In a preferred embodiment, the metastasis is bone metastasis. In a yet more preferred embodiment, the bone metastasis is osteolytic bone metastasis. As used herein, the expression "osteolytic bone metastasis" refers to a type of metastasis in which bone resorption (progressive loss of bone density) is produced in the proximity of the metastasis resulting from the stimulation of the osteoclast activity by the tumor cells and is characterized by severe pain, pathological fractures, hypercalcaemia, spinal cord compression and other syndromes resulting from nerve compression.

Therapeutic Methods of the Invention

Treating Bone Metastasis using C-MAF Inhibitory Agents

The authors of the present invention have clearly shown that the inhibition of the c-MAF expression in breast cancer cells causes a statistically significant reduction in the formation of bone metastasis from said cells, using to that end an experimental xenotransplantation model. Contrarily, the c-MAF over-expression in tumor cells in that same system increases the metastatic capacity of said cells. Thus, a c-MAF gene expression inhibitory agent or an inhibitory agent of the protein encoded by said gene can be used in the treatment and/or the prevention of breast cancer metastasis.

Therefore, in another aspect, the invention relates to the use of a c-MAF gene expression inhibitory agent or an inhibitory agent of the protein encoded by said gene (hereinafter, inhibitory agent of the invention) in the preparation of a medicinal product for treating and/or preventing breast cancer metastasis. Alternatively, the invention relates to a c-MAF gene expression inhibitory agent or an inhibitory agent of the protein encoded by said gene for use in the treatment and/or the prevention of breast cancer metastasis. Alternatively, the invention relates to a method for treating the breast cancer metastasis in a subject which comprises administering a c-MAF inhibitor to said subject.

As used herein, a "c-MAF inhibitory agent" refers to any molecule capable of completely or partially inhibiting the c-MAF gene expression, both by preventing the expression product of said gene from being produced (interrupting the c-MAF gene transcription and/or blocking the translation of the mRNA coming from the c-MAF gene expression) and by directly inhibiting the c-MAF protein activity. C-MAF gene expression inhibitors can be identified using methods based on the capacity of the so-called inhibitor to block the capacity of c-MAF to promote the in vitro cell proliferation, such as shown in the international patent application WO2005/046731, based on the capacity of the so-called inhibitor to block the transcription capacity of a reporter gene under the control of the cyclin D2 promoter or of a promoter containing the c-MAF response region (MARE or c-MAF responsive element) in cells which express c-MAF such as described in WO2008098351 or based on the capacity of the so-called inhibitor to block the expression of a reporter gene under the control of the IL-4 promoter in response to the stimulation with PMA/ionomycin in cells which express NFATc2 and c-MAF such as described in US2009048117A.

By way of non-limiting illustration, c-MAF inhibitory agents suitable for use in the present invention include antisense oligonucleotides, interference RNAs (siRNAs), catalytic RNAs or specific ribozymes and inhibitory antibodies.

Antisense Oligonucleotides

An additional aspect of the invention relates to the use of isolated "antisense" nucleic acids to inhibit expression, for example, for inhibiting transcription and/or translation of a nucleic acid which encodes c-MAF the activity of which is to be inhibited. The antisense nucleic acids can be bound to the target potential of the drug by means of conventional base complementarity or, for example, in the case of biding to Double stranded DNA through specific interaction in the large groove of the double helix. Generally, these methods refer to a range of techniques generally used in the art and they include any method which is based on the specific binding to oligonucleotide sequences.

An antisense construct of the present invention can be distributed, for example, as an expression plasmid which, when is transcribed in cell, produces RNA complementary to at least one unique part of the cellular mRNA encoding c-MAF. Alternatively, the antisense construct is a oligonucleotide probe generated ex vivo which, when introduced into the cell, produces inhibition of gene expression hybridizing with the mRNA and/or gene sequences of a target nucleic acid. Such oligonucleotide probes are preferably modified oligonucleotides which are resistant to endogenous nucleases, for example, exonucleases and/or endonucleases and are therefore stable in vivo. Examples of nucleic acids molecules for use thereof as an antisense oligonucleotides are DNA analogs of phosphoramidate, phosphothionate and methylphosphonate (see also U.S. Pat. Nos. 5,176,996; 5,264,564; and 5,256,775). Additionally, the general approximations for constructing oligomers useful in the antisense therapy have been reviewed, for example, in Van der Krol et al., BioTechniques 6: 958-976, 1988; and Stein et al., Cancer Res 48: 2659-2668, 1988.

With respect to the antisense oligonucleotide, the oligodeoxyribonucleotide regions derived from the starting site of the translation, for example, between −10 and +10 of the target gene are preferred. The antisense approximations involve the oligonucleotide design (either DNA or RNA) that are complementary to the mRNA encoding the target polypeptide. The antisense oligonucleotide will be bound to the transcribed mRNA and translation will be prevented.

The oligonucleotides which are complementary to the 5' end of the mRNA, for example the non translated 5' sequence up to and including the start codon AUG must function in the most efficient manner to inhibit translation. Nevertheless, it has been shown recently that the sequences complementary to the non translated 3' sequences of the mRNA are also efficient for inhibiting mRNA translation (Wagner, Nature 372: 333, 1994). Therefore, complementary oligonucleotides could be used at the non translated 5' or 3' regions, non coding regions of a gene in an antisense approximation to inhibit the translation of that mRNA. The oligonucleotides complementary to the non translated 5' region of the mRNA must include the complement of the start codon AUG. The oligonucleotides complementary to the coding region of the mRNA are less efficient translation inhibitors but they could also be used according to the invention. If they are designed to hybridize with the 5' region, 3' region or the coding region of the mRNA, the antisense nucleic acids must have at least six nucleotides long and preferably have less than approximately 100 and more preferably less than approximately 50, 25, 17 or 10 nucleotides long.

Preferably, in vitro studies are performed first to quantify the capacity of the antisense oligonucleotides for inhibiting gene expression. Preferably these studies use controls which distinguish between antisense gene inhibition and non specific biological effects of the oligonucleotides. Also preferably these studies compared the levels of target RNA or protein with that of an internal control of RNA or protein. The results obtained using the antisense oligonucleotides can be compared with those obtained using a control oligonucleotide. Preferably the control oligonucleotide is approximately of the same length as the oligonucleotide to be assayed and that the oligonucleotide sequence does not differ from the antisense sequence more than it is deemed necessary to prevent the specific hybridization to the target sequence.

The antisense oligonucleotide can be a single or double stranded DNA or RNA or chimeric mixtures or derivatives or modified versions thereof. The oligonucleotide can be modified in the base group, the sugar group or the phosphate backbone, for example, to improve the stability of the molecule, its hybridization capacity etc. The oligonucleotide may include other bound groups, such as peptides (for example, for directing them to the receptors of the host cells) or agents for facilitating transport through the cell membrane (see, for example, Letsinger et al., Proc. Natl. Acad. Sci. U.S.A. 86: 6553-6556, 1989; Lemaitre et al., Proc. Natl. Acad. Sci. 84: 648-652, 1987; PCT Publication No. WO 88/09810) or the blood-brain barrier (see, for example, PCT Publication No. WO 89/10134), intercalating agents (see, for example, Zon, Pharm. Res. 5: 539-549, 1988). For this purpose, the oligonucleotide can be conjugated to another molecule, for example, a peptide, a transporting agent, hybridization triggered cleaving agent, etc.

The antisense oligonucleotides may comprise at least one group of modified base. The antisense oligonucleotide may also comprise at least a modified sugar group selected from the group including but not limited to arabinose, 2-fluoro-arabinose, xylulose, and hexose. The antisense oligonucleotide may also contain a backbone similar to a neutral peptide. Such molecules are known as peptide nucleic acid (PNA) oligomers and are described, for example, in Perry-O'Keefe et al., Proc. Natl. Acad. Sci. U.S.A. 93: 14670, 1996, and in Eglom et al., Nature 365: 566, 1993.

In yet another embodiment, the antisense oligonucleotide comprises at least one modified phosphate backbone. In yet another embodiment, the antisense oligonucleotide is an alpha-anomeric oligonucleotide.

While antisense oligonucleotides complementary to the coding region of the target mRNA sequence can be used, those complementary to the transcribed non translated region can also be used.

In some cases, it may be difficult to reach the sufficient intracellular concentrations of the antisense to suppress the endogenous mRNA translation. Therefore, a preferred approximation uses a recombinant DNA construct in which the antisense oligonucleotide is placed under the control of a strong pol III or pol II promoter.

Alternatively, the target gene expression can be reduced by directing deoxyribonucleotide sequences complementary to the gene regulating region (i.e., the promoter and/or enhancers) to form triple helix structures preventing gene transcription in the target cells in the body (see in general, Helene, Anticancer Drug Des. 6(6): 569-84, 1991). In certain embodiments, the antisense oligonucleotides are antisense morpholines.

SiRNA

Small interference RNA or siRNA are agents which are capable of inhibiting the expression of a target gene by means of RNA interference. A siRNA can be chemically synthesized, can be obtained by means of in vitro transcription or can be synthesized in vivo in the target cell. Typically, the siRNA consist of a double stranded RNA between 15 and 40 nucleotide long and may contain a 3' and/or 5' protruding region of 1 to 6 nucleotides. The length of the protruding region is independent of the total length of the siRNA molecule. The siRNA act by means of degrading or silencing the target messenger after transcription.

The siRNA of the invention are substantially homologous to the mRNA of the c-MAF encoding gene or to the gene sequence which encodes said protein. "Substantially homologous" is understood as having a sequence which is sufficiently complementary or similar to the target mRNA such that the siRNA is capable of degrading the latter through RNA interference. The siRNA suitable for causing said interference include siRNA formed by RNA, as well as siRNA containing different chemical modifications such as:

siRNA in which the bonds between the nucleotides are different than those appear in nature, such as phosphorothionate bonds.

Conjugates of the RNA strand with a functional reagent, such as a fluorophore.

Modifications of the ends of the RNA strands, particularly of the 3' end by means of the modification with different hydroxyl functional groups in 2' position.

Nucleotides with modified sugars such as 0-alkylated residues on 2' position like 2'-O-methylribose or 2'-O-fluororibose.

Nucleotides with modified bases such as halogenated bases (for example 5-bromouracil and 5-iodouracil), alkylated bases (for example 7-methylguanosine). The siRNA can be used as is, i.e., in the form of a double stranded RNA with the aforementioned characteristics. Alternatively, the use of vectors containing the sense and antisense strand sequence of the siRNA is possible under the control of suitable promoters for the expression thereof in the cell of interest.

Vectors suitable for expressing siRNA are those in which the two DNA regions encoding the two strands of siRNA are arranged in tandem in one and the same DNA strand separated by a spacer region which, upon transcription, forms a loop and wherein a single promoter directs the transcription of the DNA molecule giving rise to shRNA.

Alternatively, the use of vectors in which each of the strands forming the siRNA is formed from the transcription of a different transcriptional unit is possible. These vectors are in turn divided into divergent and convergent transcription vectors. In divergent transcription vectors, the transcriptional units encoding each of the DNA strands forming the siRNA are located in tandem in a vector such that the transcription of each DNA strand depends on its own promoter which may be the same or different (Wang, J. et al., 2003, Proc. Natl. Acad. Sci. USA., 100:5103-5106 and Lee, N. S., et al., 2002, Nat. Biotechnol., 20:500-505). In convergent transcription vectors, the DNA regions giving rise to the siRNA form the sense and antisense strands of a DNA region which are flanked by two reverse promoters. After the transcription of the sense and antisense RNA strands, the latter will form the hybrid for forming a functional siRNA. Vectors with reverse promoter systems in which 2 U6 promoters (Tran, N. et al., 2003, BMC Biotechnol., 3:21), a mouse U6 promoter and a human H1 promoter (Zheng, L., et al., 2004, Proc. Natl. Acad. Sci. USA., 135-140 and WO 2005026322) and a human U6 promoter and a mouse H1 promoter (Kaykas, A. and Moon, R., 2004, BMC Cell Biol., 5:16) are used have been described.

Promoters suitable for use thereof in the expression of siRNA from convergent or divergent expression vectors include any promoter or pair of promoters compatible with the cells in which the siRNA is to be expressed. Thus, promoters suitable for the present invention include but are not necessarily limited to constitutive promoters such as those derived from the genomes of eukaryotic viruses such as the polyoma virus, adenovirus, SV40, CMV, avian sarcoma virus, hepatitis B virus, the metallothionein gene promoter, the thymidine kinase gene promoter of the herpes simplex virus, retrovirus LTR regions, the immunoglobulin gene promoter, the actin gene promoter, the EF-1alpha gene promoter as well as inducible promoters in which the protein expression depends on the addition of a molecule or an exogenous signal such as the tetracycline system, the NFkappaB/UV light system, the Cre/Lox system and the heat shock gene promoter, the regulatable RNA polymerase II promoters described in WO/2006/135436 as well as specific tissue promoters (for example, the PSA promoter described in WO2006012221). In a preferred embodiment, the promoters are RNA polymerase III promoters which act constitutively. The RNA polymerase III promoters are found in a limited number of genes such as 5S RNA, tRNA, 7SL RNA and U6 snRNA. Unlike other RNA polymerase III promoters, type III promoters do not require any intragenic sequence but rather need sequences in 5' direction comprising a TATA box in positions −34 and −24, a proximal sequence element or PSE between −66 and −47 and, in some cases, a distal sequence element or DSE between positions −265 and −149. In a preferred embodiment, the type III RNA polymerase III promoters are the human or murine H1 and U6 gene promoters. In a yet more preferred embodiment, the promoters are 2 human or murine U6 promoters, a mouse U6 promoter and a human H1 promoter or a human U6 promoter and a mouse H1 promoter. In the context of the present invention, the ER alpha gene promoters or cyclin D1 gene promoters are especially suitable and therefore they are especially preferred to specifically express the genes of interest in breast tumors, preferably in ER+ breast tumors.

The siRNA can be generated intracellularly from the so called shRNA (short hairpin RNA) characterized in that the antiparallel strands forming the siRNA are connected by a loop or hairpin region. The shRNAs can be encoded by plasmids or viruses, particularly retroviruses, and are under the control of a promoter. Promoters suitable for expressing shRNA are those indicated in the paragraph above for expressing siRNA.

Vectors suitable for expressing siRNA and shRNA include prokaryotic expression vectors such as pUC18, pUC19, Bluescript and the derivatives thereof, mp18, mp19, pBR322, pMB9, ColE1, pCR1, RP4, phages and shuttle vectors such as pSA3 and pAT28, yeast expression vectors such as 2-micron plasmid type vectors, integration plasmids, YEP vectors, centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenovirus, viruses associated with adenoviruses as well as retroviruses and particularly lentiviruses) higher eukaryotic cell expression vectors or non-viral vectors such as pcDNA3, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1. In a preferred embodiment, the vectors are lentiviral vectors.

The siRNA and shRNA of the invention can be obtained using a series of techniques known by the person skilled in the art. The region of the nucleotide sequence taken as a basis for designing the siRNA is not limiting and it may contain a region of the coding sequence (between the start codon and the end codon) or it may alternatively contain sequences of the non-translated 5' or 3' region preferably between 25 and 50 nucleotides long and in any position in 3' direction position with respect to the start codon. One way of designing an siRNA involves the identification of the AA(N19)TT motifs wherein N can be any nucleotide in the c-MAF gene sequence, and the selection of those having a high G/C content. If said motif is not found, it is possible to identify the NA(N21) motif wherein N can be any nucleotide.

c-MAF specific siRNAs include the siRNA described in WO2005046731, one of the strands of which is ACGG-CUCGAGCAGCGACAA (SEQ ID NO: 6). Other c-MAF specific siRNA sequences include but are not limited to CUUACCAGUGUGUUCACAA (SEQ ID NO: 7), UGGAAGACUACUACUGGAUG (SEQ ID NO: 8), AUUUGCAGUCAUGGAGAACC (SEQ ID NO: 9), CAAGGAGAAAUACGAGAAGU (SEQ ID NO: 10), ACAAGGAGAAAUACGAGAAG (SEQ ID NO: 11) and ACCUGGAAGACUACUACUGG (SEQ ID NO: 12).

DNA Enzymes

On the other hand, the invention also contemplates the use of DNA enzymes to inhibit the expression of the c-MAF gene of the invention. DNA enzymes incorporate some of the mechanistic features of both antisense and ribozyme technologies. DNA enzymes are designed such that they recognize a particular target nucleic acid sequence similar to the antisense oligonucleotide, nevertheless like the ribozyme they are catalytic and specifically cleave the target nucleic acid.

Ribozymes

Ribozyme molecules designed for catalytically cleaving transcription products of a target mRNA to prevent the translation of the mRNA which encodes c-MAF the activity of which is to be inhibited, can also be used. Ribozymes are enzymatic RNA molecules capable of catalyzing specific RNA cleaving. (For a review, see, Rossi, Current Biology 4: 469-471, 1994). The mechanism of ribozyme action involves a specific hybridization of a ribozyme molecule sequence to a complementary target RNA followed by an endonucleolytic cleavage event. The composition of the ribozyme molecules preferably includes one or more sequences complementary to the target mRNA and the well known sequence responsible for cleaving the mRNA or a functionally equivalent sequence (see, for example, U.S. Pat. No. 5,093,246).

The ribozymes used in the present invention include hammer-head ribozymes, endoribonuclease RNA (hereinafter "Cech type ribozymes") (Zaug et al., Science 224:574-578, 1984).

The ribozymes can be formed by modified oligonucleotides (for example to improve the stability, targeting, etc.) and they should be distributed to cells expressing the target gene in vivo. A preferred distribution method involves using a DNA construct which "encodes" the ribozyme under the control of a strong constitutive pol III or pol II promoter such that the transfected cells will produce sufficient amounts of the ribozyme to destroy the endogenous target messengers and to inhibit translation. Since the ribozymes are catalytic, unlike other antisense molecules, a low intracellular concentration is required for its efficiency.

Inhibitory Antibodies

In the context of the present invention, "inhibitory antibody" is understood as any antibody capable of binding specifically to the c-MAF protein and inhibiting one or more of the functions of said protein, preferably those related to transcription. The antibodies can be prepared using any of the methods which are known by the person skilled in the art, some of which have been mentioned above. Thus, the polyclonal antibodies are prepared by means of immunizing an animal with the protein to be inhibited. The monoclonal antibodies are prepared using the method described by Kohler, Milstein et al. (Nature, 1975, 256: 495). In the context of the present invention, suitable antibodies include intact antibodies comprising a variable antigen binding region and a constant region, "Fab", "F(ab')2" and "Fab'", Fv, scFv fragments, diabodies and bispecific antibodies. Once antibodies with c-MAF protein binding capacity are identified, those capable of inhibiting the activity of this protein will be selected using an inhibitory agent identification assay.

Inhibitory Peptides

As used herein, the term "inhibitory peptide" refers to those peptides capable of binding to the c-MAF protein and inhibiting its activity as has been explained above, i.e., preventing the c-MAF from being able to activate gene transcription.

Negative C-MAF Dominants

Since the proteins from the maf family are capable of homodimerizing and heterodimerizing with other members of the AP-1 family such as Fos and Jun, one way of inhibiting c-MAF activity is by means of using negative dominants capable of dimerizing with c-MAF but lacking the capacity for activating transcription. Thus, the negative c-MAF dominants can be any of the small maf proteins existing in the cell and lacking two-thirds of the amino terminal end containing the transactivation domain (for example, mafK, mafF, mafg and pi 8) (Fujiwara et al (1993) Oncogene 8, 2371-2380; Igarashi et al. (1995) J. Biol. Chem. 270, 7615-7624; Andrews et al. (1993) Proc. Natl. Acad. Sci. USA 90, 11488-11492; Kataoka et al. (1995) Mol. Cell. Biol. 15, 2180-2190) (Kataoka et al. (1996) Oncogene 12, 53-62).

Alternatively, the negative c-MAF dominants include c-MAF variants which maintain the capacity for dimerizing with other proteins but lack the capacity for activating transcription. These variants are, for example, those lacking the c-MAF transactivation domain located at the N-terminal end of the protein. Thus, negative c-MAF dominant variants include in an illustrative manner the variants in which at least amino acids 1 to 122, at least amino acids 1-187 or at least amino acids 1 to 257 (by considering the numbering of human c-MAF as described in U.S. Pat. No. 6,274,338) have been removed.

The invention contemplates the use of both the negative c-MAF dominant variants and of polynucleotides encoding c-MAF under the operative control of a promoter suitable for expression in target cell. The promoters that can be used for regulating the polynucleotide transcription of the invention can be constitutive promoters, i.e., promoters directing the transcription at a basal level, or inducible promoters in which the transcriptional activity requires an external signal. Constitutive promoters suitable for regulating transcription are, among others, the CMV promoter, the SV40 promoter, the DHFR promoter, the mouse mammary tumor virus (MMTV) promoter, the 1a elongation factor (EF1a) promoter, the albumin promoter, the ApoA1 promoter, the keratin promoter, the CD3 promoter, the immunoglobulin heavy or light chain promoter, the neurofilament promoter, the neuron specific enolase promoter, the L7 promoter, the CD2 promoter, the myosin light chain kinase promoter, the HOX gene promoter, the thymidine kinase promoter, the RNA polymerase II promoter, the MyoD gene promoter, the phosphoglyceratekinase (PGK) gene promoter, the low density lipoprotein (LDL) promoter, the actin gene promoter. In a preferred embodiment, the promoter regulating the expression of the transactivator is the PGK gene promoter. In a preferred embodiment, the promoter regulating the polynucleotide transcription of the invention is the RNA polymerase promoter of the T7 phage.

Preferably, the inducible promoters that can be used in the context of the present invention are those responding to an inducer agent showing zero or negligible basal expression in the absence of an inducer agent and are capable of promoting the activation of gene located in the 3' position. Depending on the type of inducer agent, the inducible promoters are classified as Tet on/off promoters (Gossen, M. and H. Bujard (1992) Proc. Natl. Acad. Sci. USA, 89:5547-5551; Gossen, M. et al., 1995, Science 268:1766-1769; Rossi, F. M. V. and H. M. Blau, 1998, Curr. Opin. Biotechnol. 9:451-456); Pip on/off promoters (U.S. Pat. No. 6,287,813); antiprogestin-dependent promoters (US 2004132086), ecdysone-dependent promoters (Christopherson et al., 1992, Proc. Natl. Acad. Sci. USA, 89:6314-6318; No et al., 1996, Proc. Natl. Acad. Sci. USA, 93:3346-3351, Suhr et al., 1998, Proc. Natl. Acad. Sci. USA, 95:7999-8004 and WO9738117), a metallothionein-dependent promoter (WO8604920) and rapamycin-dependent promoters (Rivera et al., 1996, Nat. Med. 2:1028-32).

Vectors suitable for expressing the polynucleotide encoding the negative c-MAF dominant variant include vectors derived from prokaryotic expression vectors such as pUC18, pUC19, Bluescript and derivatives thereof, mp18, mp19, pBR322, pMB9, ColE1, pCR1, RP4, phages and shuttle vectors such as pSA3 and pAT28, yeast expression vectors such as 2-micron type plasmid vectors, integration plasmids, YEP vectors, centromeric plasmids and the like, insect cell expression vectors such as pAC series vectors and pVL series vectors, plant expression vectors such as pIBI, pEarleyGate, pAVA, pCAMBIA, pGSA, pGWB, pMDC, pMY, pORE series vectors and the like and viral vector-based (adenoviruses, viruses associated with adenoviruses as well as retroviruses and particularly lentiviruses) higher eukaryotic cell expression vectors OR non-viral vectors such as pSilencer 4.1-CMV (Ambion), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1.

Other Inhibitory Compounds of the C-MAF Protein Activity

Other C-MAF Inhibitory Compounds Suitable for use in the Present Invention Include:

TABLE 1 small molecules with c-MAF inhibiting capacity

I Endiandric acid H derivatives such as those described in WO2004014888 corresponding to the general formula

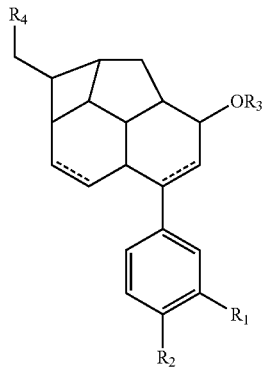

TABLE 1-continued small molecules with c-MAF inhibiting capacity wherein
R$_1$ and R$_2$ are, independently of one another,
1.0 H or
2.0 a —O—C$_1$-C$_6$-alkyl, —O—C$_2$-C$_6$-alkenyl, —O—C$_2$-C$_6$-alkynyl or —O—C$_6$-C$_{10}$-aryl group, in which alkyl, alkenyl and alkynyl are straight-chain or branched, and in which the alkyl, alkenyl and alkynyl groups are mono- or disubstituted with:
2.1 —OH,
2.2 =O,
2.3 —O—C$_1$-C6-alkyl, in which alkyl is straight-chain or branched,
2.4 -O—C$_2$-C$_6$-alkenyl, in which alkenyl is straight-chain or branched,
2.5 C$_6$-C$_{10}$-aryl,
2.6 —NH—C$_1$-C$_6$-alkyl, in which alkyl is straight-chain or branched,
2.7 —NH—C$_2$-C$_6$-alkenyl, in which alkenyl is straight-chain or branched,
2.8 —NH$_2$ or
2.9 halogen,
and in which the aryl group, is optionally mono- or disubstituted with the substituent 2.1 or 2.3 to 2.9,
in which the substituents 2.3, 2.4, 2.6 and 2.7 may be further substituted with —CN, -amide or -oxime functions, and 2.5 may be further substituted with —CN or amide functions, or R$_1$ and R$_2$ together form a ring, wherein R$_1$ and R$_2$ mean a —O—[(C$_1$-C$_6$)-alkylene]-O— group,
R$_3$ is
1.0 H or
2.0 a —O—C$_1$-C$_6$-alkyl, —O—C$_2$-C$_6$-alkenyl, —O—C$_2$-C$_6$-alkynyl or —O—C$_6$-C$_{10}$-aryl group, in which alkyl, alkenyl and alkynyl are straight-chain or branched, and in which the alkyl, alkenyl and alkynyl groups are mono- or disubstituted with:
2.1 —OH,
2.2 =O,
2.3 —O—C$_1$-C$_6$-alkyl, in which alkyl is straight-chain or branched,
2.4 —O—C$_2$-C$_6$-alkenyl, in which alkenyl is straight-chain or branched,
2.5 —C$_6$-C$_{10}$-aryl,
2.6 —NH—C$_1$-C$_6$-alkyl, in which alkyl is straight-chain or branched,
2.7 —NH—C$_2$-C$_6$-alkenyl, in which alkenyl is straight-chain or branched,
2.8 —NH$_2$ or
2.9 halogen,
and in which the aryl group, is optionally mono- or disubstituted with the substituent 2.1 or 2.3 to 2.9,
in which the substituents 2.3, 2.4, 2.6 and 2.7 may be further substituted with —CN, -amide or -oxime functions, and 2.5 may be further substituted with —CN or amide functions
R$_4$ is CO$_2$R$_3$, CO$_2$NHR$_3$, CHO, CH$_2$OR$_3$, CH$_2$OSi(R$_3$)$_3$, CH$_2$Br, CH$_2$CN, in which R$_3$ is as defined above,
and, in particular, the compounds

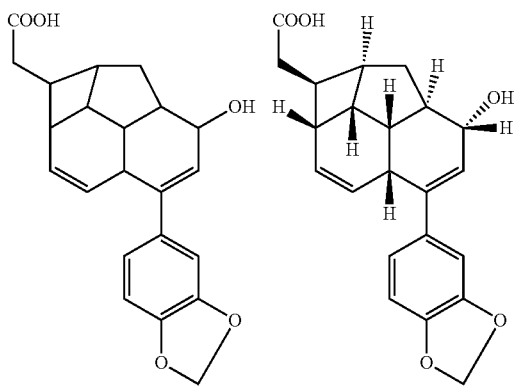

II 8-hydroxyquinoline derivatives such as those described in WO2009146546 of general formula

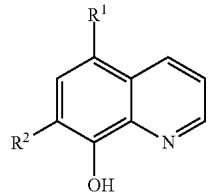

wherein
R$_1$ is selected from the group consisting of NO$_2$, NH$_2$, NH(C$_1$-C$_6$-alkyl) and N(C$_1$-C$_6$-alkyl)(C$_1$-C$_6$-alkyl);
R$_2$ is selected from H, halogen, C$_1$-C$_6$ alkyl, and fluoro-substituted C$_1$-C$_6$ alkyl,
or
R$_1$ is Cl and R$_2$ is Br or H,
and, preferably, the compounds

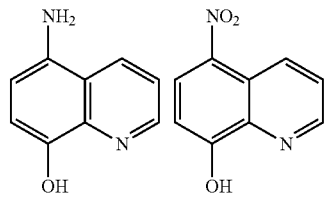

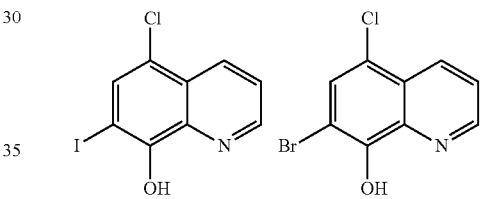

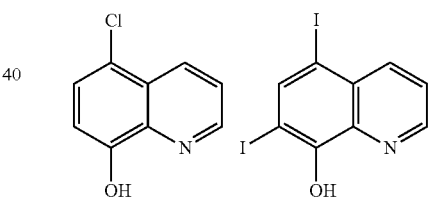

III Clioquinol (5-chloro-7-iodoquinolin-8-ol) as described in WO09049410
IV Compounds such as those described in WO08098351 of general formula

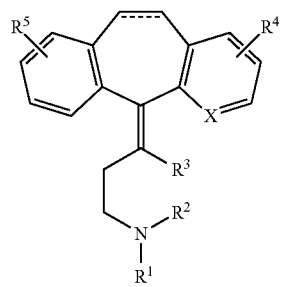

wherein
═══:—:—: is a single or double bond,
R$^1$ is selected from the group consisting of H, C$_1$-C$_4$ alkyl, C(O)O C$_1$-C$_4$ alkyl, C(O) C$_1$-C$_4$ alkyl and C(O)NH C$_1$-C$_4$ alkyl;
R$^2$ is selected from H and C$_1$-C$_4$ alkyl;
R$^3$ is selected from H and C$_1$-C$_4$ alkyl;

TABLE 1-continued small molecules with c-MAF inhibiting capacity or $R^2$ and $R^3$ are bound together along with the carbon and nitrogen atoms to which they are bound to form a piperidine ring,
$R^4$ and $R^5$ are independently selected from H, halogen, hydroxy, $C_1$-$C_4$ alkyl, fluoro-substituted $C_1$-$C_4$ alkyl and $C_1$-$C_4$ alkoxy; and
X is selected from C and N,
and preferred compounds such as
Cyproheptadine (4-(5H-dibenzo-[a,d]cyclohepten-5-ylidene)-1-methylpiperidine hydrochloride),
Amitriptyline (3-(10,11-dihydro-5H-dibenzo[[a,d]]cycloheptene-5-ylidene)-N,N-dimethyl-1-propanamine),
Loratadine (Ethyl 4-(8-chloro-5,6-dihydro-11H-benzo[5,6]cyclohepta[1,2-b]pyridin-11-ylidene)-1-piperidinecarboxylate,
Cyclobenzrapine (3-(5H-dibenzo[a,d]cyclohepten-5-ylidene)- N,N-dimethyl-1-propanamine).

V Nivalenol (12,13-epoxy-3,4,7,15-tetrahydroxytrichothec-9-en-8-one) as described in WO0359249

Other c-MAF inhibitors are described in the patent application WO2005063252, such as shown in the following table (Table 2).

TABLE 2 c-MAF inhibitors

| Antagonist | Reference for cdk2 inhibitory activity |
|---|---|
| Purine Analogs | |
| Purvalanols such as 2-(1R-Isopropyl-2-hydroxyethylamino)-6-(3-chloroanilino)-9-isopropylpurine having a molecular formula $C_{19}H_{25}ClN_6O$ available from Sigma-Aldrich under the trade name Purvalanol A (#P4484, Sigma-Aldrich, St. Louis, MO), Purvalanol B, aminopurvalanol, compound 52 (where isopropyl of purvalanol A is replaced with H) | Gray, N.S. et al., Science, 281, 533-538 (1998); Chang, Y.T. et al., Chem. Biol., 6, 361-375 (1999). |
| 2-(Hydroxyethylamino)-6-benzylamino-9-methylpurine having a molecular formula $C_{15}H_{18}N_6O$ available from Sigma-Aldrich under the trade name Olomoucine (#O0886), 2-(2'-Hydroxyethylamino)-6-benzylamino-9-isopropylpurine having a molecular formula $C_{17}H_{22}N_6O$ available from Sigma-Aldrich under the trade name $N^9$-isopropylolomoucine (#I0763); CVT-313 | Vesely, J. et al., (1994) Eur. J. Biochem. 224, 771-86, 11; Brooks, E.E., et al., (1997) J. Biol. Chem., 272, 29207-11 |
| 6-(Benzylamino)-2(R)-[[1-(hydroxymethyl)propyl]amino]-9-isopropylpurine 2-(R)-[[9-(1-methylethyl)-6-[(phenylmethyl)amino]-9H-purin-2-yl]amino]-1-butanol having a molecular formula of $C_{19}H_{26}N_6O$ available from Sigma- | Wang, D. et al., J. Virol., 75, 7266-7279 (2001); McClue, S.J. et al., Int. J. Cancer, 102, 463-468 (2002); Meijer, L., et al., (1997) Eur. J. Biochem., 243, 527-36 |
| Aldrich under the trade name Roscovitine (#R7772), methoxyroscovitine Purine analog N2-(cis-2-Aminocyclohexyl)-N6-(3-chlorophenyl)-9-ethyl-9H-purine-2,6-diamine having a molecular formula of $C_{19}H_{24}ClN_7$ available from Sigma-Aldrich under the trade name CGP74514 (#C3353) | Imbach, P. et al., Bioorg. Med. Chem. Lett., 9, 91-96 (1999); Dreyer, M.K. et al., J. Med. Chem., 44, 524-530 (2001). |
| CGP79807, a purine analog of CGP74514 (supra) where Cl is replaced with CN, OH is removed, and the ortho position of cyclohexane ring is $NH_2$ | Imbach, P. et al., Bioorg. Med. Chem. Lett., 9, 91-96 (1999); Dreyer, M.K. et al., J. Med. Chem., 44, 524-530 (2001). |
| purine analog such as O6-cyclohexylmethyl guanine NU2058 | Arris, C.E., et al., J. Med. Chem. 43, 2797-2804 (2000); Davies et al, Nature Structural Biology, 9:10, 745-749, 2002 |
| purine analog such as NU6102 | Arris, C.E., et al., J. Med. Chem. 43, 2797-2804 (2000); Davies, T.G. et al, Nat. Struct. Biol., 9, 745-749, (2002). |
| isopentenyl-adenine | Vesely, J., et al, (1994) Eur. J. Biochem., 224, 771-86 |
| Nonpurine based agents | |
| Indirubins such as indirubin-3'-monoxime having a molecular formula of $C_{16}H_{11}N_3O_2$ available from Sigma-Aldrich under the trade name (#I0404), indirubin 5-sulfonate, 5-chloro indirubin | Davies, T.G., et al., Structure, 9, 389-397 (2001); Marko, D. et al., Br. J. Cancer, 84, 283-289 (2001); Hoessel, R., et al., (1999) Nat. Cell Biol., 1, 60-7; PCT/US02/30059 to Hellberg et al., published as WO 03/027275. |
| Oxindole 1 of Fischer as referenced in column 2 of this table, (#IN118, JMAR Chemical, | Porcs-Makkay, M., et al., Tetrahedron 2000, 56, 5893; Org. Process Res. Dev. 2000, 4, 10 |
| Indenopyrazoles | Nugiel, D.A. et al., J. Med. Chem., 44, 1334-1336 (2001); Nugiel, D.A. et al., J. Med. Chem., 45, 5224-5232 (2002); Yue, E.W. et al., J. Med. Chem. 45, 5233-5248 (2002). |
| Pyrido(2,3-d)pyrimidine-7-ones, compound 3 of Fischer | Barvian, M. et al., J. Med. Chem 43, 4606-4616 (2000); Toogood, P.L., Med. Res. Rev., 21, 487-498 (2001). |
| Quinazolines such as anilinoquinazoline | Sielecki, T.M. et al., Bioorg. Med. Chem. Lett., 11, 1157-1160 (2001); Mettey et al., J Med. Chem. 2003, 46, 222-236. |

TABLE 2-continued c-MAF inhibitors

| Antagonist | Reference for cdk2 inhibitory activity |
|---|---|
| Thiazoles such as fused thiazole, 4-{[(7-Oxo-6,7-dihydro-8H-[1,3]thiazolo[5,4-e]indol-8-ylidene)methyl]amino}-N-(2-pyridyl)benzenesulfonamide having a molecular formula of $C_{21}H_{15}N_5O_3S_2$ available from Sigma-Aldrich under the trade name GW8510 (#G7791) | Davis, S.T. et al., Science, 291, 134-137 (2001); PCT/US02/30059 to Hellberg et al., published as WO 03/027275. |
| Flavopiridols such as flavopiridol (L86 8275; NCS 649890, National Cancer Institute, Bethesda, MD) and a dechloro derivative | Carlson, B.A., et al., (1996) Cancer Res., 56, 2973-8 |
| Alkaloids such as Stauroporine (#S1016, A.G. Scientific, San Diego, CA) or UCN-01 (7-hydroxystaurosporine) National Cancer Institute, Bethesda, MD | Rialet, V., et al., (1991) Anticancer Res., 11, 1581-90; Wang, Q., et al., (1995) Cell Growth Differ., 6, 927-36, Akiyama, T., et al., (1997) Cancer Res., 57, 1495-501, Kawakami, K., et al., (1996) Biochem. Biophys. Res., Commun., 219, 778-83 |
| Paullones such as 9-Bromo-7,12-dihydro-indolo[3,2-d][1]benzazepin-6(5H)-one having a molecular formula of $C_{16}H_{11}BrN_2O$ available from Sigma-Aldrich under the trade name kenpaullone (#K3888), or 9-Nitro-7,12-dihydroindolo-[3,2-d][1]benzazepin-6(5)-one having a molecular formula of $C_{16}H_{11}N_3O_3$ available from Sigma-Aldrich under the trade name alsterpaullone (#A4847) | Zaharevitz, D.W., et al., Cancer Res., 59, 2566-2569 (1999); Schultz, C. et al., J. Med. Chem., 42, 2909-2919 (1999); Zaharevitz, D.W., et al., (1999) Cancer Res., 59, 2566-9; PCT/US02/30059 to Hellberg et al., published as WO 03/027275. |
| CGP 41251, an alkaloid | Begemann, M., et al., (1998) Anticancer Res., 18, 2275-82; Fabbro et al., Pharmacol Ther. 1999 May-June; 82(2-3):293-301 |
| Hymenialdisines such as 10z-hymenialdisine having a molecular formula of $C_{11}H_{10}BrN_5O_2$ available from Biochemicals.net, a division of A.G. Scientific, Inc. (San Diego, CA) (H-1150) | Meijer, L., et al., (1999) Chemistry & Biology, 7, 51-63; PCT/US02/30059 to Hellberg et al., published as WO 03/027275. |
| CGP60474, a phenylaminopyrimidine | 21; WO95/09853, Zimmerman et al., Sep. 21, 1994 |
| Thiazolopyrimidine 2 | Attaby et al., Z, Naturforsch. 54b, 788-798 (1999) |
| Diarylurea | Honma, T. et al., J. Med. Chem., 44, 4628-4640 (2001), Honma, T. et al., J. Med. Chem., 44, 4615-4627 (2001). |
| (2R)-2,5-Dihydro-4-hydroxy-2-[(4-hydroxy-3-(3-methyl-2-butenyl)phenyl)methyl]-3-(4-hydroxyphenyl)-5-oxo-2-furancarboxylic acid methyl ester having a molecular formula of $C_{24}H_{24}O_7$ available from Sigma-Aldrich under the trade name Butyrolactone-I (B7930) | Kitagawa, M. et al., Oncogene, 8, 2425-2432 (1993). |
| Aloisine A, Cat. No. 128125 (Calbiochem, San Diego, CA) | Mettey et al., J Med. Chem. 2003, 46, 222-236 |

In a preferred embodiment, the c-MAF inhibitory agents are used for the treatment and/or prevention of bone metastasis. In a yet more preferred embodiment, the bone metastasis is osteolytic metastasis.

The c-MAF inhibitory agents are typically administered in combination with a pharmaceutically acceptable carrier.

The term "carrier" refers to a diluent or an excipient whereby the active ingredient is administered. Such pharmaceutical carriers can be sterile liquids such as water and oil, including those of a petroleum, animal, plant or synthetic origin such peanut oil, soy oil, mineral oil, sesame oil and the like. Water or aqueous saline solutions and aqueous dextrose and glycerol solutions, particularly for injectable solutions, are preferably used as carriers. Suitable pharmaceutical carriers are described in "Remington's Pharmaceutical Sciences" by E. W. Martin, 1995. Preferably, the carriers of the invention are approved by the state or federal government regulatory agency or are listed in the United States Pharmacopeia or other pharmacopeia generally recognized for use thereof in animals and more particularly in human beings.

The carriers and auxiliary substances necessary for manufacturing the desired pharmaceutical dosage form of the pharmaceutical composition of the invention will depend, among other factors, on the pharmaceutical dosage form chosen. Said pharmaceutical dosage forms of the pharmaceutical composition will be manufactured according to the conventional methods known by the person skilled in the art. A review of the different methods for administering active ingredients, excipients to be used and processes for producing them can be found in "Tratado de Farmacia Galénica", C. Faulí i Trillo, Luzán 5, S.A. 1993 Edition. Examples of pharmaceutical compositions include any solid composition (tablets, pills, capsules, granules, etc.) or liquid composition (solutions, suspensions or emulsions) for oral, topical or parenteral administration. Furthermore, the pharmaceutical composition may contain, as deemed necessary, stabilizers, suspensions, preservatives, surfactants and the like.

For use in medicine, the c-MAF inhibitory agents can be found in the form of a prodrug, salt, solvate or clathrate, either isolated or in combination with additional active agents and can be formulated together with a pharmaceutically acceptable excipient. Excipients preferred for use thereof in the present invention include sugars, starches, celluloses, rubbers and proteins. In a particular embodiment, the pharmaceutical composition of the invention will be formulated in a solid pharmaceutical dosage form (for example tablets, capsules, pills, granules, suppositories, sterile crystal or amorphous solids that can be reconstituted to provide liquid forms etc.), liquid pharmaceutical dosage form (for example solutions, suspensions, emulsions, elixirs, lotions, ointments etc.) or semisolid pharmaceutical dosage form (gels, ointments, creams and the like). The pharmaceutical compositions of the invention can be administered by any route, including but not limited to the oral route, intravenous route, intramuscular route, intraarterial route, intramedularry route, intrathecal route, intraventricular router, transdermal route, subcutaneous route, intraperitoneal route, intranasal route, enteric route, topical route, sublingual route or rectal route. A review of the different ways for administering active ingredients, of the excipients to be used and of the manufacturing processes thereof can be found in Tratado de Farmacia Galénica, C. Faulí i Trillo, Luzán 5, S.A., 1993 Edition and in Remington's Pharmaceutical Sciences (A. R. Gennaro, Ed.), 20th edition, Williams & Wilkins PA, USA (2000). Examples of pharmaceutically acceptable carriers are known in the state of art and include phosphate buffered saline solutions, water, emulsions such as oil/water emulsions, different types of wetting agents, sterile solutions, etc. The compositions comprising said carriers can be formulated by conventional processes known in the state of the art.

In the event that nucleic acids (siRNA, polynucleotides encoding siRNA or shRNA or polynucleotides encoding negative c-MAF dominants) are administered the invention contemplates pharmaceutical compositions particularly prepared for administering said nucleic acids. The pharmaceutical compositions can comprise said naked nucleic acids, i.e., in the absence of compounds protecting the nucleic acids from degradation by the nucleases of the body, which entails the advantage that the toxicity associated with the reagents used for transfection is eliminated. Administration routes suitable for naked compounds include the intravascular route, intratumor route, intracranial route, intraperitoneal route, intrasplenic route, intramuscular route, subretinal route, subcutaneous route, mucosal route, topical route and oral route (Templeton, 2002, DNA Cell Biol., 21:857-867). Alternatively, the nucleic acids can be administered forming part of liposomes conjugated to cholesterol or conjugated to compounds capable of promoting the translocation through cell membranes such as the Tat peptide derived from the HIV-1 TAT protein, the third helix of the homeodomain of the D. melanogaster antennapedia protein, the herpes simplex virus VP22 protein, arginine oligomers and peptides as described in WO07069090 (Lindgren, A. et al., 2000, Trends Pharmacol. Sci, 21:99-103, Schwarze, S. R. et al., 2000, Trends Pharmacol. Sci., 21:45-48, Lundberg, M et al., 2003, Mol Therapy 8:143-150 and Snyder, E. L. and Dowdy, S. F., 2004, Pharm. Res. 21:389-393). Alternatively, the polynucleotide can be administered forming part of a plasmid vector or viral vector, preferably adenovirus-based vectors, in adeno-associated viruses or in retroviruses such as viruses based on murine leukemia virus (MLV) or on lentivirus (HIV, FIV, EIAV).

The c-MAF inhibitory agents or the pharmaceutical compositions containing them can be administered at a dose of less than 10 mg per kilogram of body weight, preferably less than 5, 2, 1, 0.5, 0.1, 0.05, 0.01, 0.005, 0.001, 0.0005, 0.0001, 0.00005 or 0.00001 mg per kg of body weight. The unit dose can be administered by injection, inhalation or topical administration.

The dose depends on the severity and the response of the condition to be treated and it may vary between several days and months or until the condition subsides. The optimal dosage can be determined by periodically measuring the concentrations of the agent in the body of the patient. The optimal dose can be determined from the EC50 values obtained by means of previous in vitro or in vivo assays in animal models. The unit dose can be administered once a day or less than once a day, preferably less than once every 2, 4, 8 or 30 days. Alternatively, it is possible to administer a starting dose followed by one or several maintenance doses, generally of a lesser amount than the starting dose. The maintenance regimen may involve treating the patient with a dose ranging between 0.01 µg and 1.4 mg/kg of body weight per day, for example 10, 1, 0.1, 0.01, 0.001, or 0.00001 mg per kg of body weight per day. The maintenance doses are preferably administered at the most once every 5, 10 or 30 days. The treatment must be continued for a time that will vary according to the type of disorder the patient suffers, the severity thereof and the condition of the patient. After treatment, the progress of the patient must be monitored to determine if the dose should be increased in the event that the disease does not respond to the treatment or the dose is reduced if an improvement of the disease is observed or if unwanted side effects are observed.

Treatment or Prevention of the Bone Degradation in Breast Cancer Patients with Bone Metastasis having Elevated C-MAF Levels The authors of the present invention have demonstrated that the c-MAF levels are elevated in the bone metastasis from breast tumors. Likewise, the authors of the present invention have clearly shown that the conditioning medium of cell lines derived from primary breast tumors which have high capacity for causing a bone metastasis and which over-express c-MAF are capable of inducing the formation osteoclasts in a greater extent than the cells which do not over-express c-MAF. Thus, those patients suffering breast cancer which has metastasized in bone and in which there are elevated c-MAF levels in said metastasis may benefit particularly from therapies aimed at preventing the bone degradation caused by the increased osteoclastic activity.

Thus, in another aspect, the invention relates to the use of an agent for avoiding or preventing bone degradation in the preparation of a medicinal product for the prevention and/or the treatment of the bone metastasis in a subject suffering breast cancer and has elevated c-MAF levels in a metastatic tumor tissue sample with respect to a control sample.

Alternatively, the invention relates to an agent for avoiding or preventing bone degradation for use in the prevention and/or the treatment of the bone metastasis in a subject suffering breast cancer and has elevated c-MAF levels in a metastatic tumor tissue sample with respect to a control sample.

Alternatively, the invention relates to a method of prevention and/or treatment of the degradation in a subject suffering breast cancer and has elevated c-MAF levels in a metastatic tumor tissue sample with respect to a control sample, which comprises administering an agent for avoiding or preventing bone degradation to said subject.

In a particular embodiment, the bone metastasis is osteolytic metastasis. In another particular embodiment, the breast cancer is ER+ or ER− breast cancer.

The terms and expressions "subject", "ER+ breast cancer", "tumor tissue sample", "metastasis", "c-MAF gene", "increased or elevated expression levels" and "control sample" have been described in detail in relation with the first method of the invention and are equally applicable to the agent for avoiding or preventing bone degradation.

Agents capable of avoiding or preventing bone degradation suitable for the therapeutic method described in the present invention have been described in detail above in the context of the customized therapy method.

The reference or control sample is a tumor tissue sample of a subject with ER+ or ER− breast cancer who has not suffered metastasis or that correspond to the median value of the c-MAF gene expression levels measured in a tumor tissue collection in biopsy samples of subjects with ER+ breast cancer who have not suffered metastasis.

Methods for determining or quantifying if the c-MAF levels are elevated with respect to a control sample have been described in detail in relation with the first method of the invention and are equally applicable to the agent for avoiding or preventing bone degradation.

Alternatively a combined treatment can be carried out, in which more than one agent for avoiding or preventing bone degradation from those mentioned above are combined to treat and/or prevent the metastasis or said agents can be combined with other supplements, such as calcium or vitamin D or with a hormone.

The agents for avoiding or preventing bone degradation are typically administered in combination with a pharmaceutically acceptable carrier. The term "carrier" and the types of carriers have been defined above for the c-MAF inhibitory agent, as well as the form and the dose in which they can be administered and are equally applicable to the agent for avoiding or preventing bone degradation.

The following examples illustrate the invention and do not limit the scope thereof.

EXAMPLES

I. Materials and Methods
Experimental Study Models

New experimental models have been developed for the study of metastasis in ER+ breast cancer. For this purpose a human ER+ breast cancer cell line called MCF7 which was transfected in a stable manner with a vector allowing the GFP/Luciferase expression has been used. This cell line was inoculated in immunodeficient mice (Balb-c/nude) by intraventricular or caudal vein injection to enable selecting cells with metastatic capacity in different organs. The mice had subcutaneous estrogen implants assuring the presence of this hormone throughout the experiment.

Selecting Metastatic Populations

The metastatic populations at different tissues were selected by means of identifying and isolating the cells of the metastatic lesions. To that end, bioluminescence imaging technique using the technology which allows detecting the planting and growth of tumor cells in organs of interest at different times and quantifying the number of tumor cells present, were used. To apply this technique, the cells have been translated for expressing the luciferase and the GFP gene and the in vivo non-invasive real time tracking methods are therefore allowed. The luminescence image (luciferase activity) is captured with the animal under anesthesia, using Xenogen IVIS equipment and the software Livingimage as preferred methodology due to their sensitivity and speed. To isolate the metastatic cells, the tumor lesion is dissected and, subsequently, by means of laser scanning cytometry techniques by fluorescence (GFP) the metastatic cells are isolated from the cells of host organism. Once these cells are isolated the process to enrich their tropism for the different tissues was repeated. By means of these methods, different metastatic populations with tissue specificity including bone metastasis were isolated.

Once the metastatic populations are identified and isolated a high performance transcriptional analysis was performed. This strategy collectively allowed identifying genes the transcription of which is increased and some acting as metastatic process mediators in cancerous cells with poor prognosis. The involvement of the genes the expression of which is altered in the colonization by the metastatic cells in tissues and specific organs was confirmed by means of an unbiased in vivo selection method.

Identifying the Group of Genes Enriched in Bone Metastasis in ER+ Breast Cancer

By means of comparing the gene expression profiles of the highly and poorly metastatic cell subpopulations, a group of genes the over-expression or repression of which is associated to an osteolytic phenotype of bone metastasis was identified. The bone osteolytic metastatic lesions (degradation) unlike the osteoblastic (synthesis), are associated to the forms of clinically more aggressive bone metastatic breast cancer. The expression profiles associated to the cell lines with high bone metastatic capacity were obtained using standardized methods. The different bone metastatic derivatives originating from ER+ mammary cells were classified through an unbiased analysis with respect to their bone aggressivity phenotype and their expression profile. In both cases the metastatic cell line derivatives, BoM1 and BoM2, demonstrated a metastatic behaviour different from that of the starting cells (MCF7), both at gene expression profile level as well as phenotypically (FIG. 1A).

The group of genes enriched for bone metastasis in ER+ breast cancer includes cytokines, cell adhesion molecules, membrane proteases, signaling mediators and transcription factors.

The group of genes selected as candidates to regulate the bone metastasis capacity in ER+ breast cancer was then subjected to clinical validation in humans. To that end, the changes of the candidate gene expression with those occurring in the gene expression profiles of two cohorts, one from primary breast tumors and the other from metastasis which include 560 and 58 breast tumors and metastasis, respectively, were compared.

Identifying Those Genes Enriched in Bone Metastasis in ER+ Breast Cancer which are Relevant in Bone Metastasis in ER− Breast Cancer The role of the genes enriched in bone metastasis in ER+ breast cancer in the ER− subtype was then evaluated. The group of genes enriched for bone metastasis in ER+ breast cancer includes the c-MAF transcription factor.

Bioinformatic and Computational Biology

Statistical R packets and Bioconductor were used to obtain the groups of genes enriched in metastasis and to verify their clinical correlation. The functions and structures specific for the data treatment were imported and they are from open public access through www.bioconductor.org.

Example 1

Selecting Relevant Genes

Figure 1B:
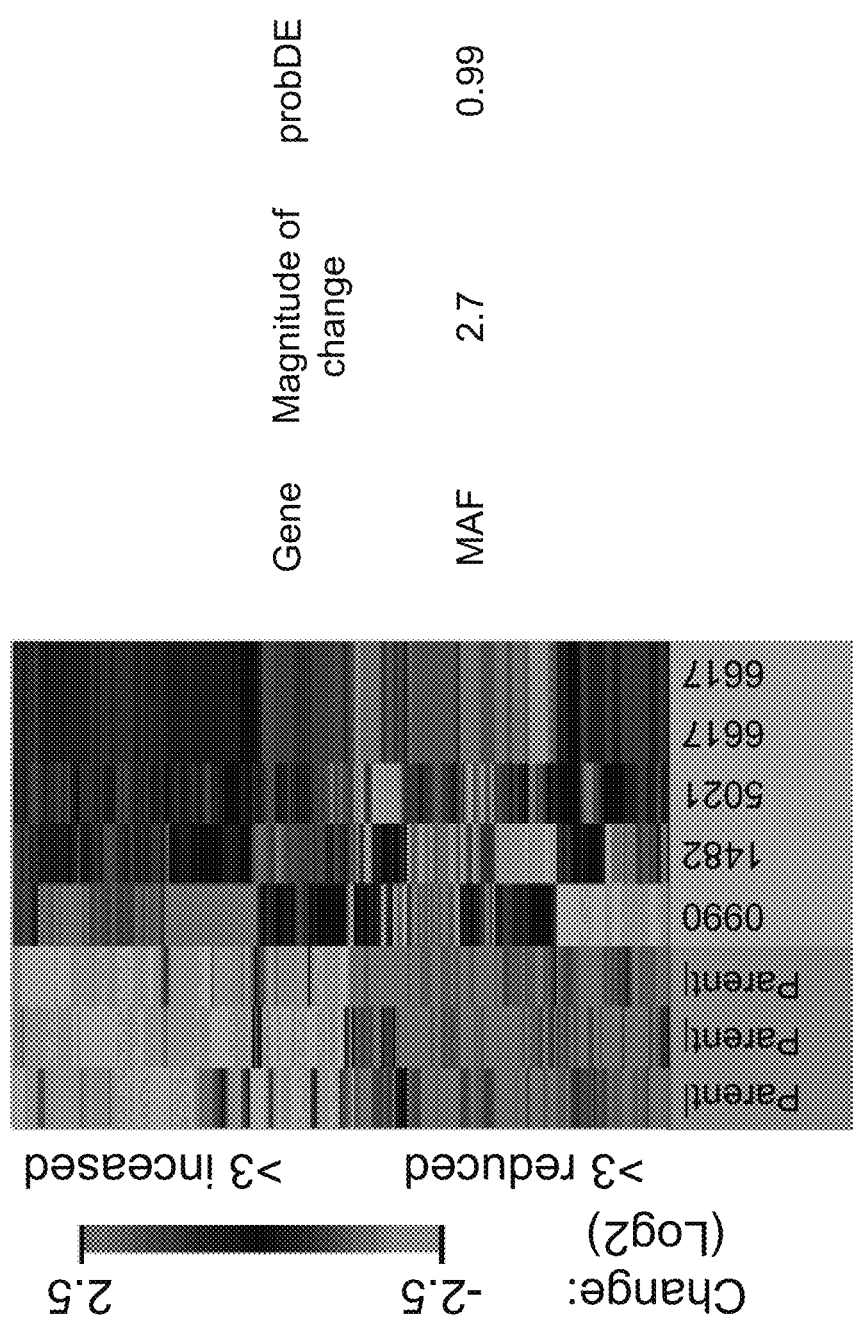
(FIG. 1B) shows the hierarchical clustering obtained from the transcriptional profiles of the parent ER+ breast cancer cells and their subsequent metastatic derivative cell lines BoM0, BoM1 and BoM2.

An analysis was conducted for selecting genes which are expressed in a differential manner in cells derived from an ER+ breast cancer cell line with tendency to form bone metastasis (FIG. 1A). The analysis conducted allowed identifying 91 genes enriched or silenced in the cell lines derived from the MCF7 ER+ cell line with capacity of metastasizing in bone (FIG. 1B). The genes and single determinant functions were selected for a more detailed study following the following criteria:
    i) Clinical correlation with aggressive ER+ breast cancer and bone metastasis.
    ii) Functions previously known by participating in processes compatibles with an aggressive phenotype (e.g., bone reabsorption, inflammation, angiogenesis), iii) Variations in the expression level between the metastatic populations in comparison to the parent populations as has been described above, and
iv) Central role in the gene regulation networks and the cell signaling pathway Based on these criteria, the c-MAF transcription factor was identified and how its variations in the expression levels predict the recurrence of primary ER+ breast cancer tumors in bone was confirmed.

Example 2

Therapeutic Value and Prognosis Value of the Genes Enriched for Bone Metastasis Regardless of the Subtype of Breast Cancer The genes enriched in the bone metastasis by means of the experimental system for selecting metastatic cell populations implemented herein were evaluated against two different databases containing the expression profiles and the clinical notes of 560 primary breast cancer tumors and 58 metastasis of breast cancer patients. These tumors are representative of all the subtypes of breast cancer and metastasis location. Both databases and their clinical notes are publicly accessible (GSE 2603, 2034, 12276 and 14020).

Figure 1C:
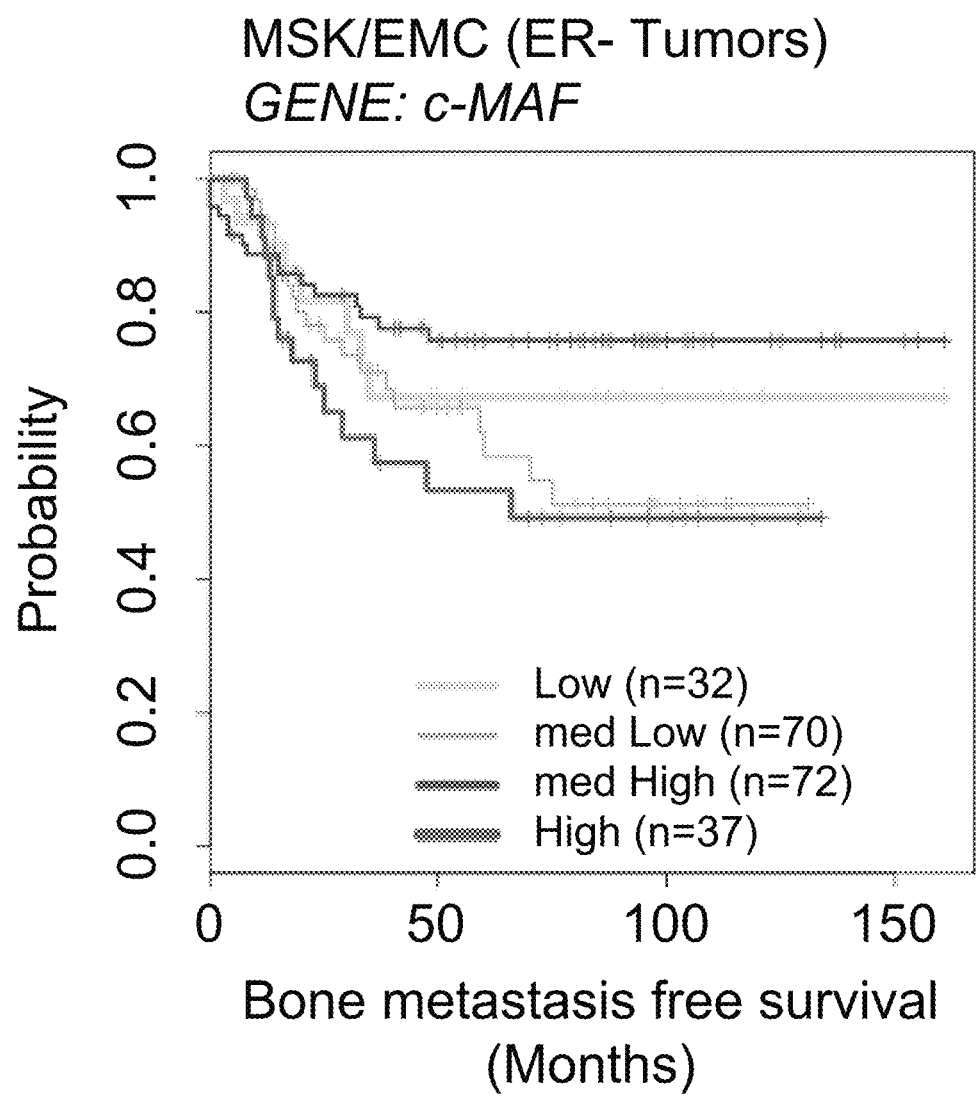
(FIG. 1C) shows the Kaplan-Meier curves where the groups of patients are separated according to the c-MAF expression levels and the probability for each group of patients to relapse and to suffer bone metastasis over time is indicated. The data set includes 560 primary breast cancer tumors. The analyses were restricted to the ER+ and ER− tumors, respectively (Gene Expression Omnibus database, accession number GSE 2603, 2034 and 12276) (FIG. 1D and FIG. 1E) shows the c-MAF expression levels were used to separate the expression profiles of the 338 primary breast cancer tumors described in the cohort of the NKI. The survival probability of the patients from each group over time is comparatively shown by means of Kaplan-Meier curve. The p-value data shown in 1C, 1D and 1E indicate that the intersection between the c-MAF gene expression and the ER, using these values as continuous variables, predicts in an independent and significant manner the recurrence or metastasis using a COX type multivariate model (p-value<0.01).
Figure 1D:
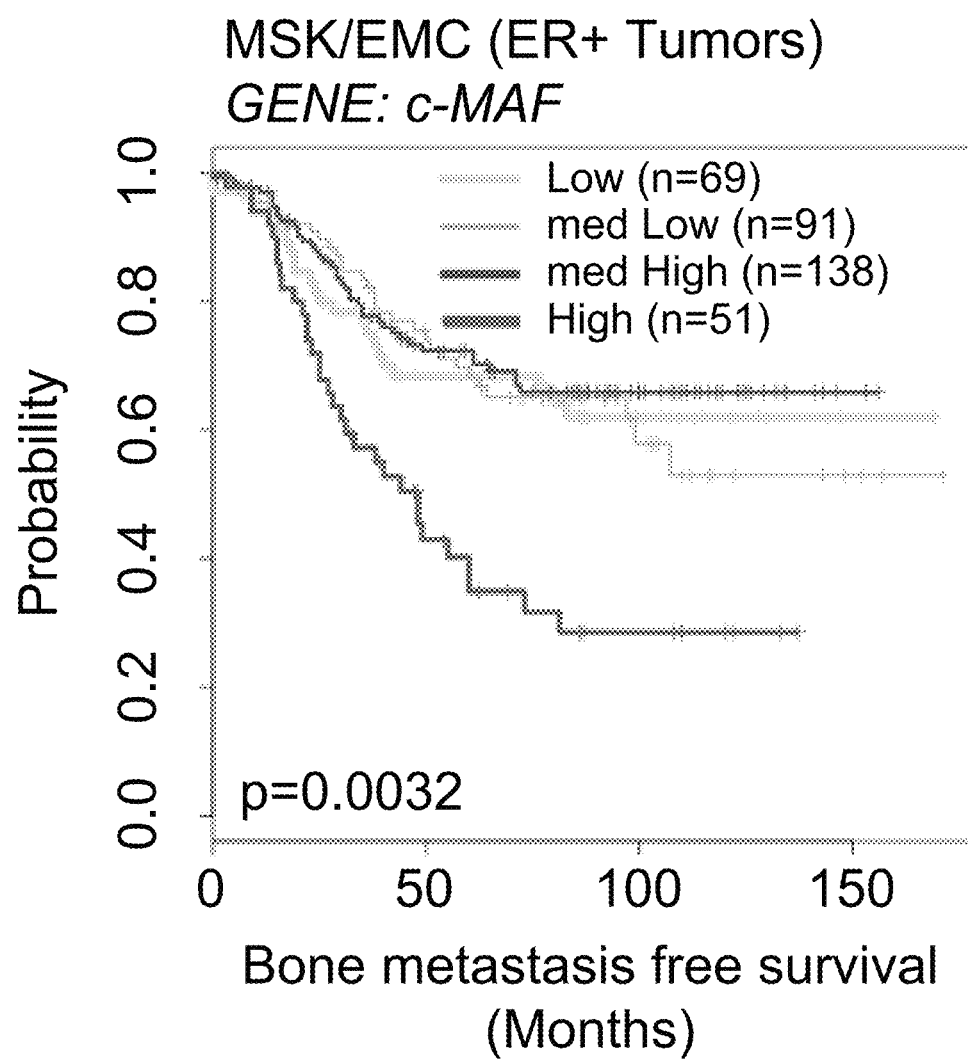
Figure 1E:
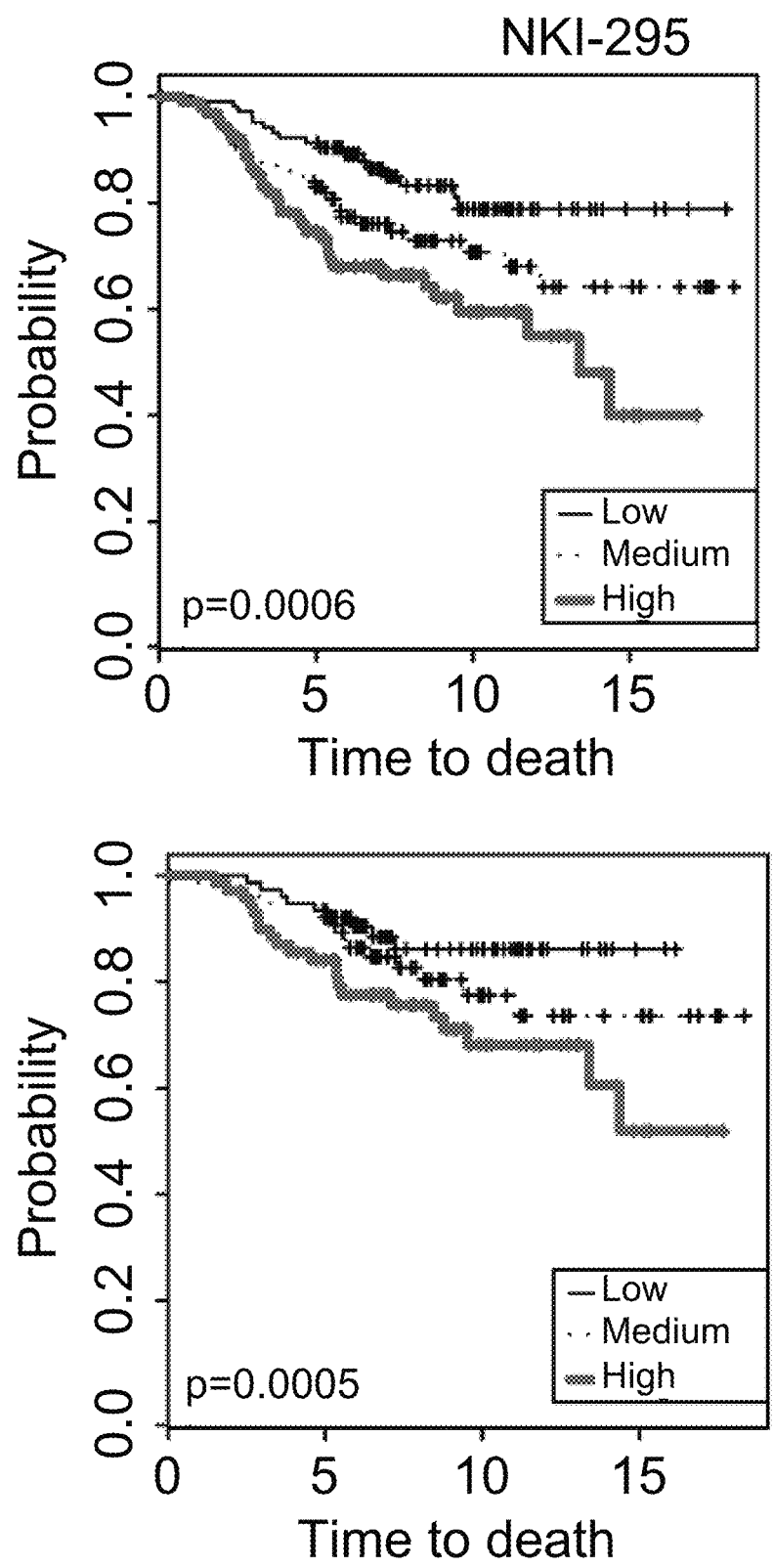

The gene expression in ER+ primary tumors of the genes of bone metastasis correlated significantly with recurrence, metastasis-free survival and survival (FIGS. 1C, D and E).

Figure 2A:
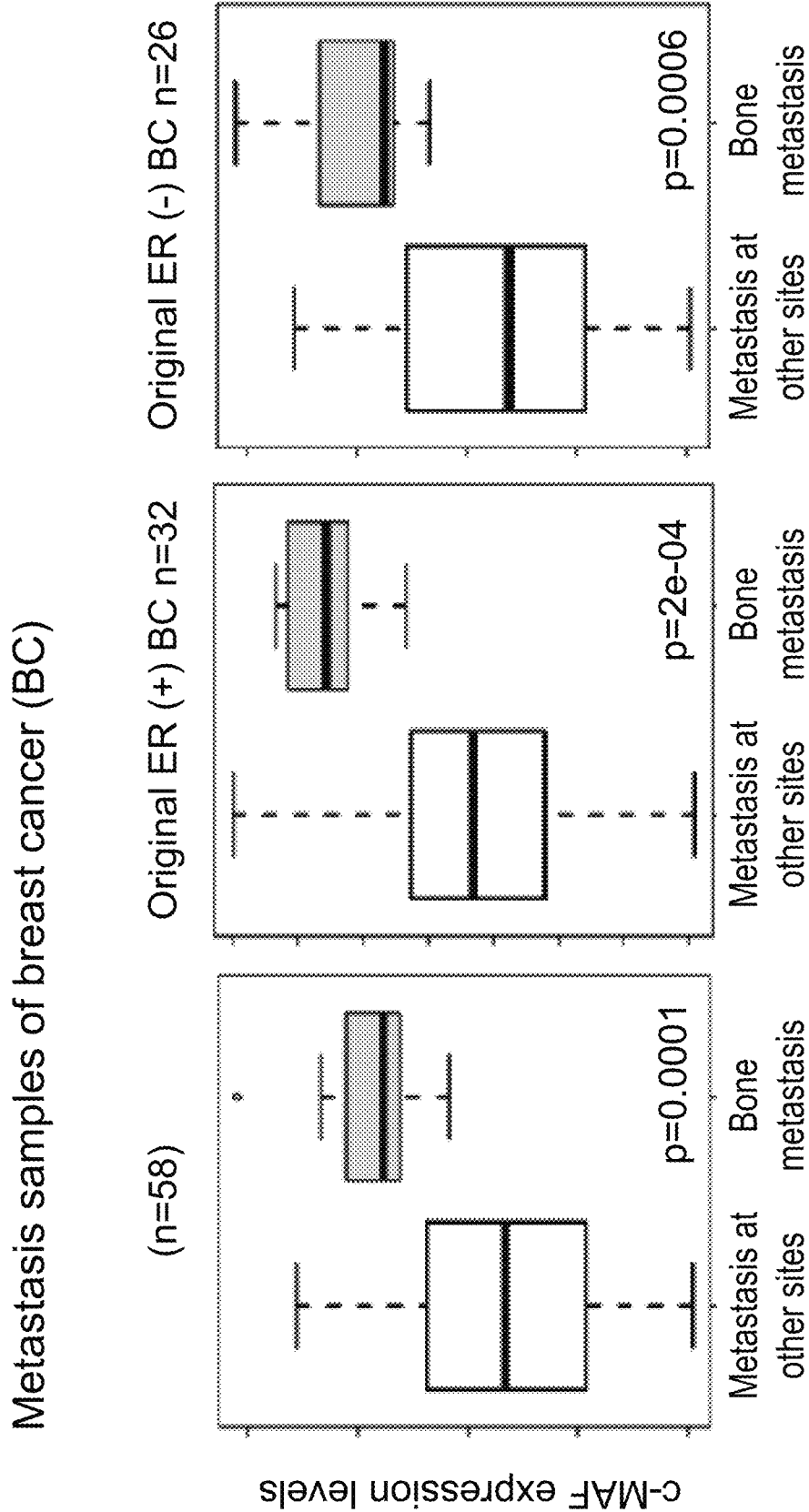
FIG. 2 (A) shows the normalized c-MAF gene expression levels in bone metastasis originating from breast cancer in comparison with other metastasis sites (brain, liver and lung) (GSE14020).
(FIG. 2B) shows the normalized c-MAF gene expression levels in different subpopulations with different bone colonization capacity and MDA-MB-231 (ER−) breast cancer cell derivatives.
(FIG. 2C) shows the normalized CTGF gene expression levels (gene induced by the transcriptional activity of c-MAF) in different subpopulations with different bone colonization capacity and MDA-MB-231 (ER−) breast cancer cell derivatives or with the exogenous over-expression of the cDNA encoding the MAF gene (long isoform).

In addition, the c-MAF gene expression levels in metastatic tissue in a cohort of 58 metastasis of breast cancer patients (GSE 14020) were evaluated. These metastases were isolated from lung, liver, bone and brain. The enrichment of the c-MAF gene specifically in bone metastasis regardless of the subtype of breast cancer, ER+ or ER−, to which the tumor or metastatic lesion (FIG. 2A) belongs to, was verified.

Example 3

Figure 2C:
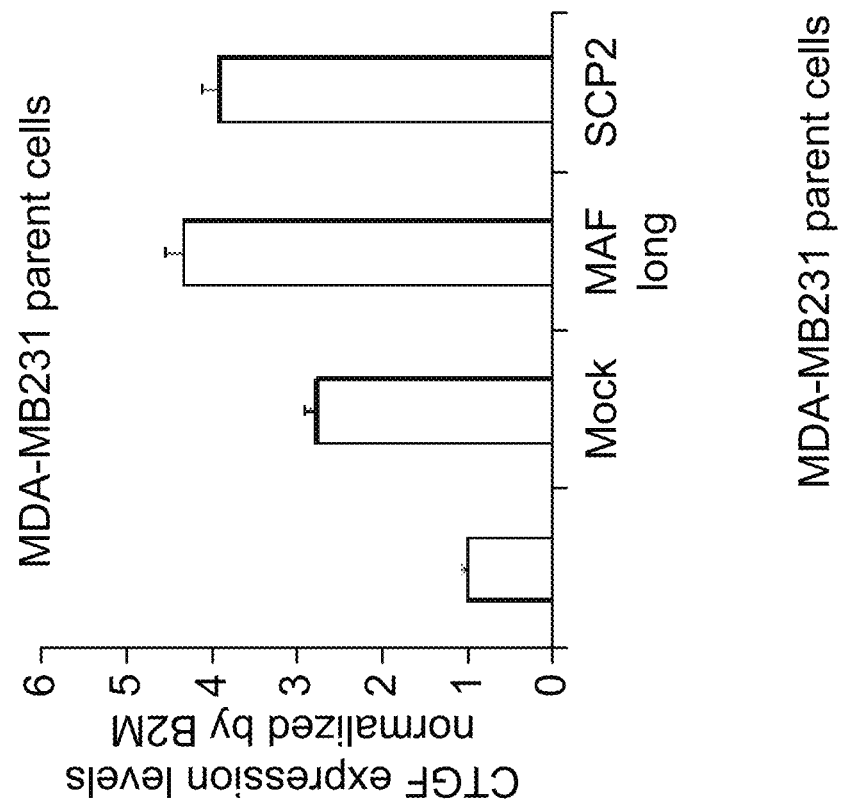
Figure 2B:
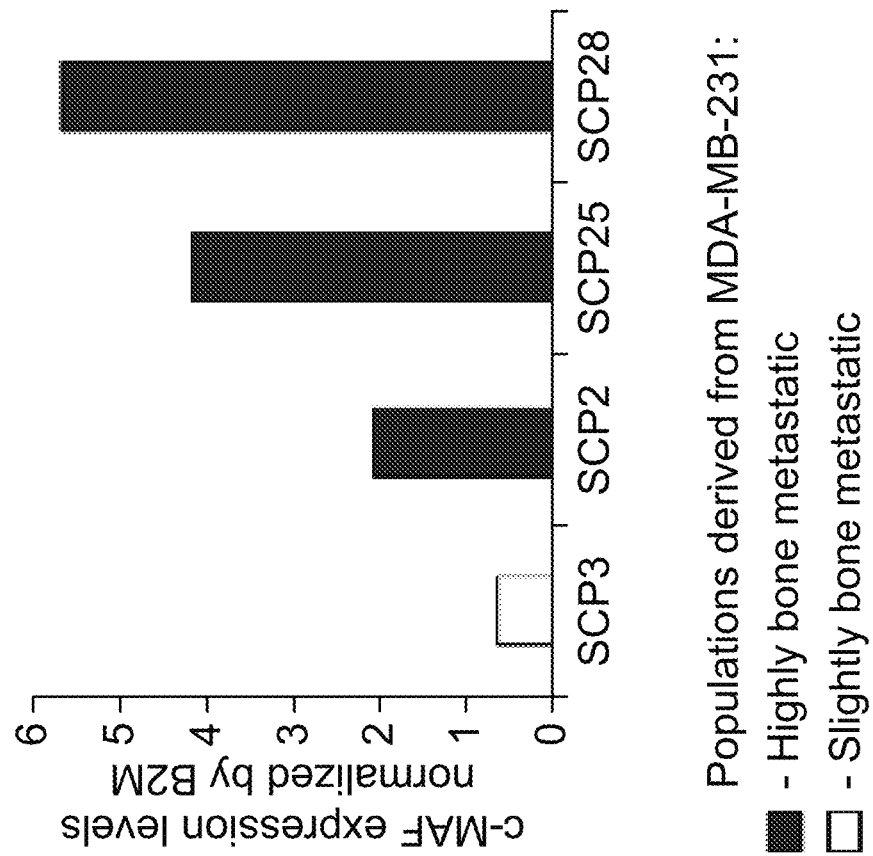

In Vivo Functional Validation of the C-MAF Bone Metastatic Gene in ER− Breast Cancer The c-MAF metastatic gene which was positive in the analysis was functionally validated in a bone metastatic colonization assay in an experimental graft model of breast cancer metastasis in mice. The selection of ER− breast cancer cells with high ability for growing in bone is accompanied by the selection of high levels of the c-MAF metastatic gene (FIG. 2B).

The approximations performed to validate the candidate gene to direct the metastasis process were gain-of-function assays. For this purpose, the c-MAF gene was expressed in the parent MDA-MB-231 cells and subsequently its capacity for inducing the expression of genes contributing to the metastasis (CTGF) (FIG. 2C), was evaluated.

Example 4

In Vivo Functional Validation of the Tissue Specific Metastatic Genes

The c-MAF metastatic gene which was positive in the analysis was functionally validated in a bone metastatic colonization assay in an experimental graft model of breast cancer metastasis in mice.

The approximations performed to validate the candidate gene to direct the metastasis process were loss-of-function and gain-of-function assays. For this purpose, the c-MAF gene was expressed or silenced in the parent cells or in the highly bone metastatic cell derivatives and subsequently its bone metastatic capacity was evaluated in vivo.

Gain-Of-Function Assays

To express the c-MAF gene lentiviral systems were used to induce the heterologous expression of the candidate gene in the parent tumor cells and those selected with low metastatic capacity. The metastasis-inducing capacity of the c-MAF gene was determined by means of techniques for tracking by bioluminescence the metastatic cells inoculated in the mouse through intracardiac route (as described in section "experimental study models"). In all the cases, the corresponding control cells infected with lentiviral vectors which did not express the protein c-MAF were injected in a parallel manner in a parallel cohort of animals as negative control (FIG. 3B).

Loss-of-Function Assays

Figure 3A:
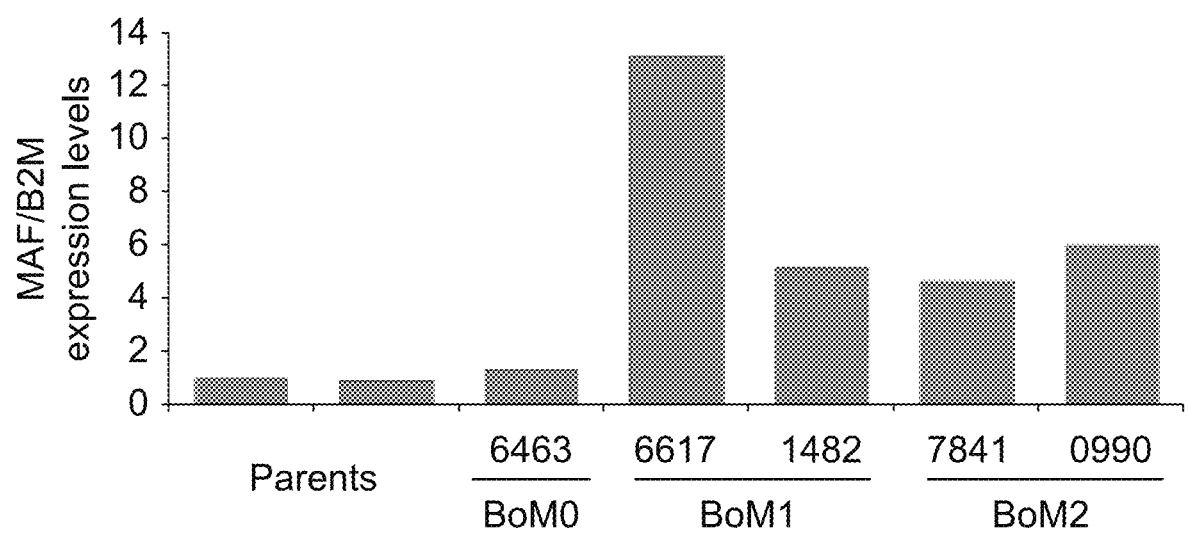
FIG. 3 (A) shows the analysis of the c-MAF expression levels in the MCF7 ER+ breast cancer cells and their metastatic derivatives (BoM) by means of RT-Quantitative-PCR.
(FIG. 3B) and (FIG. 3C) show the loss-of-function and gain-of-function experiments of c-MAF. The c-MAF lost and gained has been performed in cells highly and less metastatic in bone, respectively. The cell lines derivatives with and without c-MAF expression are injected in the left ventricle of the immunosuppressed mice and the in vivo bone colonization is analyzed in real time by means of bioluminescence imaging technique to validate the contribution of c-MAF to the bone metastasis in ER+ breast cancer. MAF-sho indicates short c-MAF (short isoform).
Figure 3B:
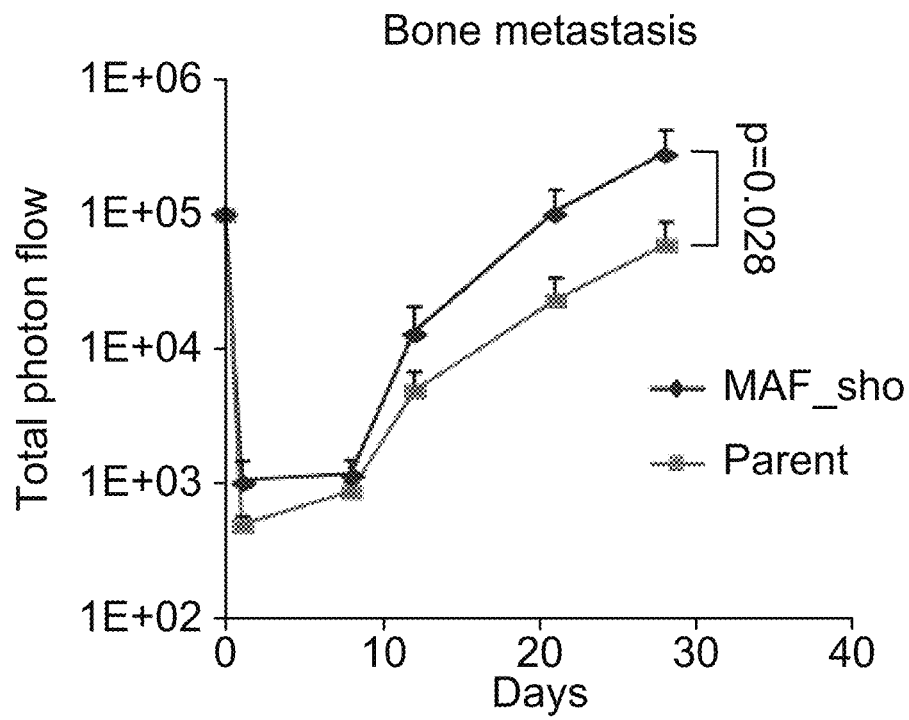
Figure 3B:
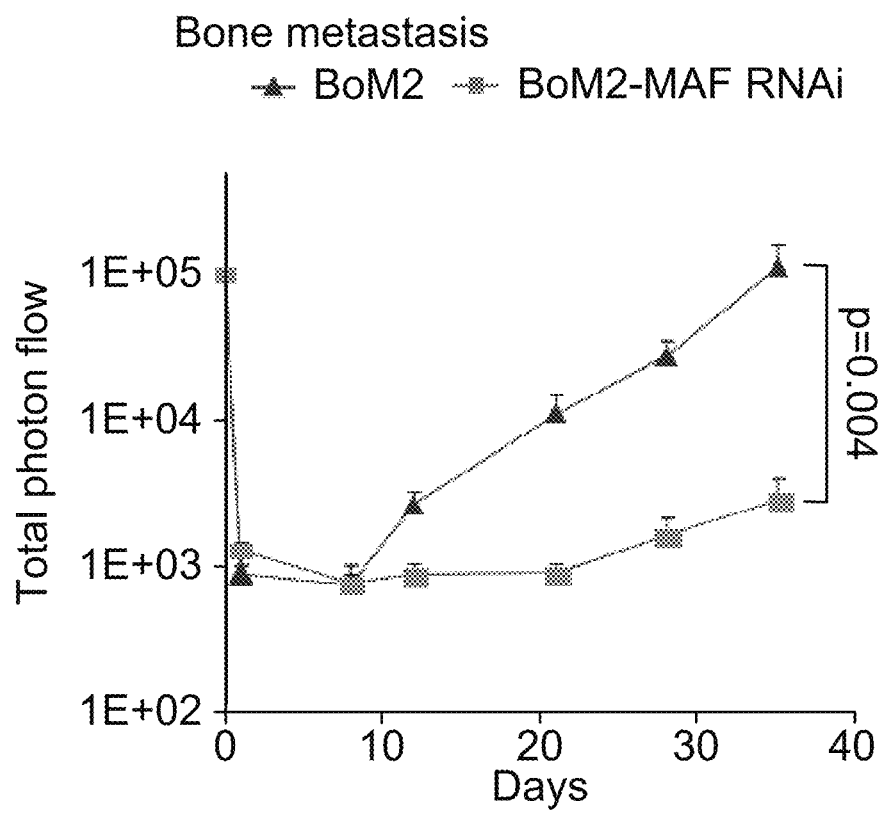
Figure 3C:
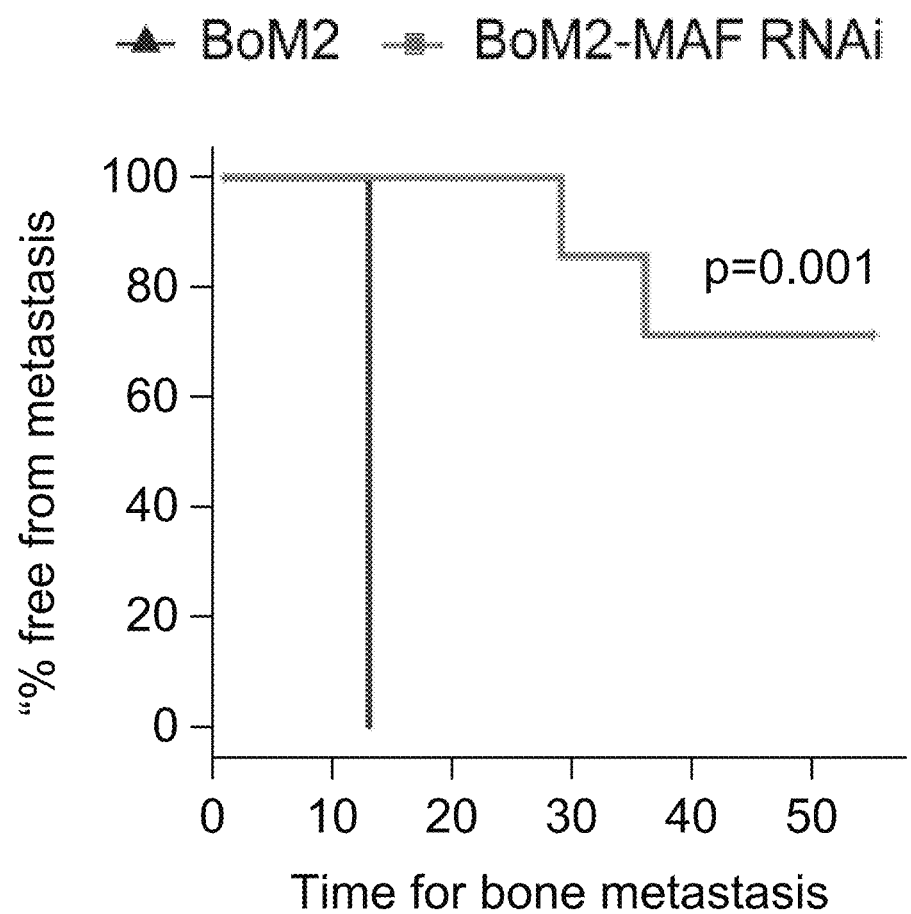

The c-MAF gene expression was suppressed in the highly bone metastatic BoM2 cell line which have high endogenous c-MAF gene expression levels (FIGS. 3A and 3C). For this purpose a lentiviral vector was used allowing the expression of an interference RNA (siRNA) with capacity for reducing the c-MAF gene expression by 80% in relation to the levels present in the BoM2 cell line. This cell population with the silenced c-MAF gene expression was inoculated through intracardiac route (as described in section "experimental study models") in immunosuppressed mice these animals being monitored to detect metastatic activity by means of bioluminescence imaging technique. In these experiments cells obtained from the BoM2 line by infection with a lentiviral vector encoding a siRNA which acts effectively against the expression of another gene which is irrelevant for the metastatic process, was used as negative control.

Example 5

Osteoclast Differentiation Assay

Figure 4:
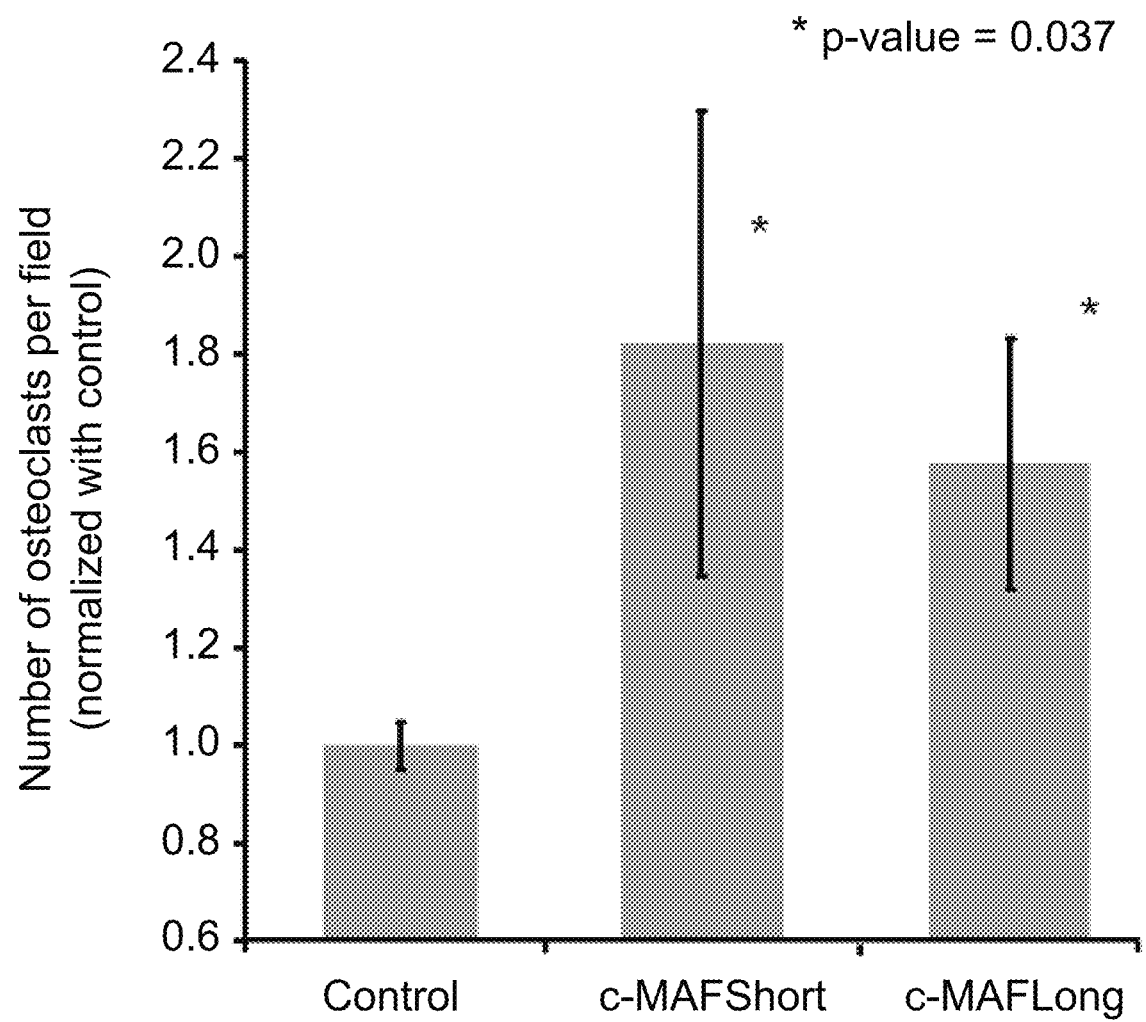
FIG. 4 shows the assay of osteoclast differentiation from bone marrow-derived precursor cells, from conditioning medium originating from MCF7 parent cells or cells over-expressing any of the c-MAF isoforms (short—short isoform and long—long isoform). The number of osteoclasts is measured by means of the TRAP technique. The statistical differences between groups are evaluated by means of the two-tailed wilcoxon test.

Primary cells originating from the bone marrow of a mouse were isolated and grown in culture in the presence of M-CSF (macrophage-colony stimulating factor). After 3 days the cells were trypsinized and seeded in 24-well plates ($1.5 \times 10^4$ cells per well) in triplicate for each experimental condition. To induce the osteoclast differentiation, these precursors were cultured with conditioning medium from MCF7 ER+ breast cancer cells with or without "short" and "long" isoform over-expression of the c-MAF gene, in the presence of RANK ligand and M-CSF. The medium was changed every three days and, on the seventh day, the specific staining of osteoclasts consisting of detecting the tartrate-resistant acid phosphatase enzyme (TRAP) was preformed. Images were obtained by means of inverted beam optical microscopy. The number of TRAP positive cells was determined and was divided between the total number of cells per field. Finally, all the values were normalized with those of the control group, MCF7. As can be observed in FIG. 4, the number of osteoclasts increased when osteoclast precursors were contacted with medium from MCF7 ER+ breast cancer cells over-expressing the short isoform or the long isoform of c-MAF.

This assay allows determining the interaction of the metastatic cells with the components from the metastatic environment or niche of the bone. The osteoclasts are responsible for the degradation of the bone and the degradation is shown in the osteolytic metastatic lesions.

Example 6

Identifying Chromosome Amplification in the Region Chr16q22-q24 (Includes C-MAF Gene)

The detection of copy number alterations (CNA) by means of expression profile analysis is theoretically possible because there is a strong correlation between the genomic alterations and the aberrant gene expression in the affected genomic regions (Pollack et al. 2002; PNAS; 99:12963-12968). Specifically, the exact detection of CNAs using gene expression analysis is possible and its difficulty stems from the type of starting expression data (Hu et al. 2009 Cancer Cell, 15:9-20).

The role of the genes enriched in bone metastasis in ER+ breast cancer has been evaluated. To that end the alterations in the genome copy number in the highly bone metastatic cells, BoM2, derived from the MCF7 breast cancer cell line which are generated in the laboratory of the researches itself and which are characterized by the expression of high c-MAF gene levels, were analyzed. This analysis has been based on the comparison of the gene expression profiles of the parent cells and BoM2 derived from MCF7. The differences of gene expression observed in the BoM2 cells in comparison with the parent cells in the position thereof, in the 23 types of chromosomes present in human cells were aligned and located.

Figure 5A:
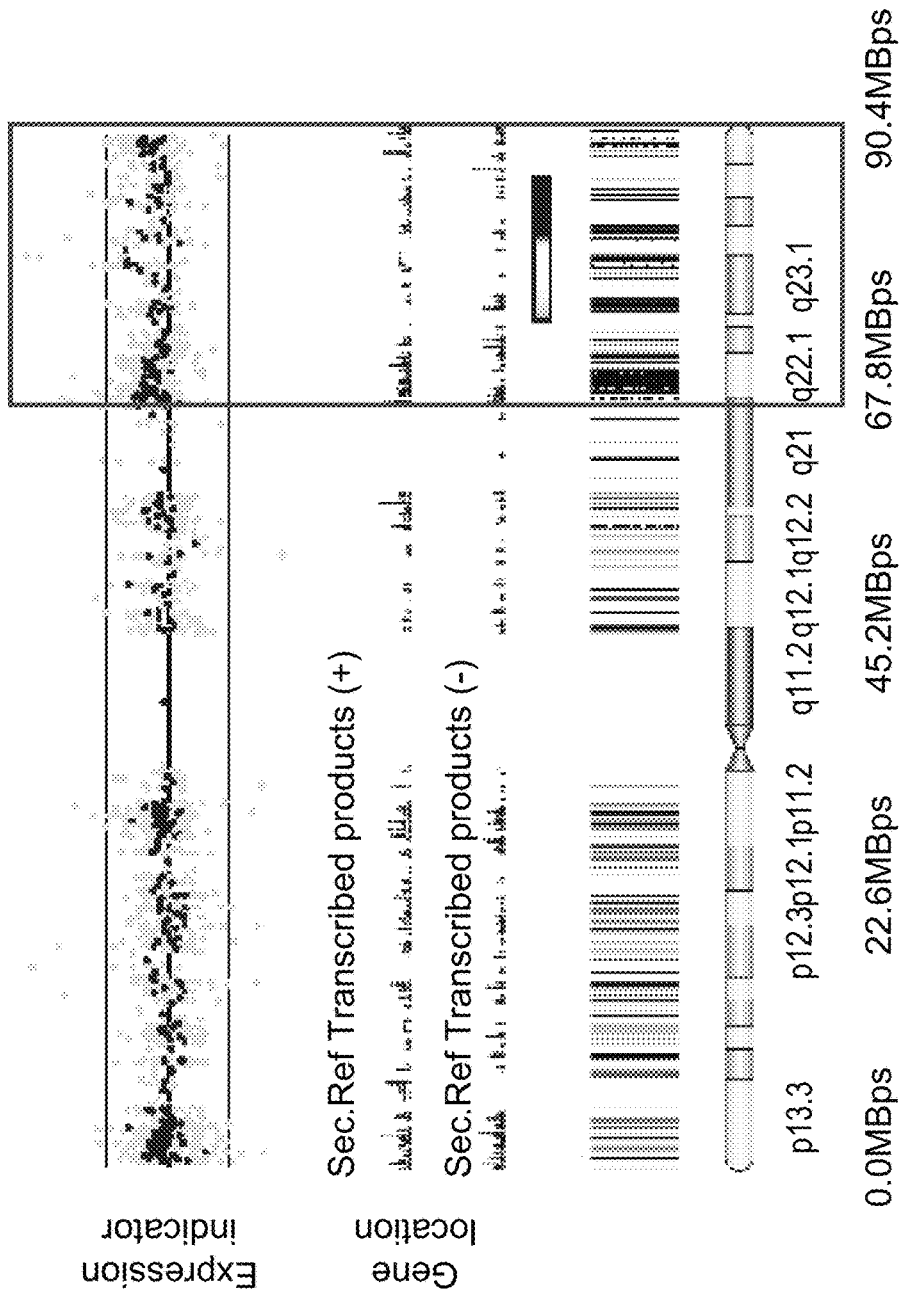
FIG. 5(A) shows the analysis of the copy number from the gene expression levels in BoM2 cells in comparison with MCF7 cells, in chromosome 16. The upper part shows an expression indicator. The centre part of the figure shows the reference sequences of transcribed products or the genes for which expression values are provided (Sec. Ref. Transcribed products), which are ordered according to their genomic position.

Thus, genomic regions (FIG. 5) have been identified wherein genes the expression of which is over-expressed or under-expressed are depicted in the BoM2 cells in comparison with the parent cells, which is an indicator of amplification or deletion of genomic DNA (Hu et al. 2009, Cancer Cell, 15:9-20). To that end, the software "Partek Genomic Suite 6.5" has been used. This software has allowed identifying those genes the expression of which is increased or reduced in the BoM2 cells in comparison with the parent cells. Once these genes are identified, the expression differences observed for each gene were depicted in the corresponding chromosomal location of said gene. The graphical depiction of these observations has allowed identifying gain-of- or loss-of-chromosomal regions based on a continuous increased or reduced gene expression with a consecutive chromosomal location (FIG. 5). The authors of the invention have been capable of locating these regions using well known cytobands described above.

Between the differentially amplified regions in the BoM2 cells, in comparison with the MCF7 ER+ parent breast cancer cells, a gain in the chromosome region 16q22-q24, which includes the locus encoding the c-MAF gene has been observed.

Figure 5B:
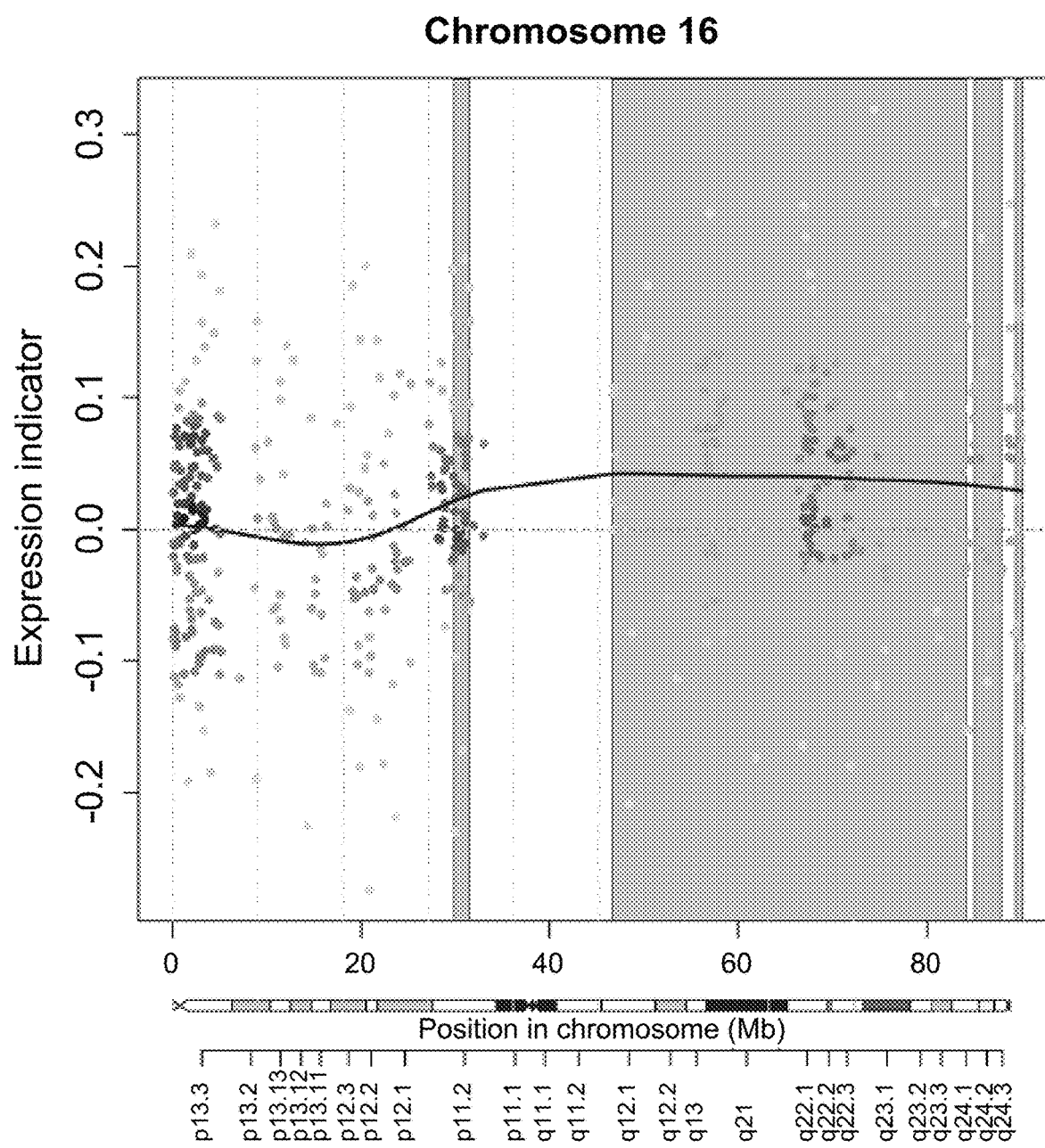
(FIG. 5B) shows the ACE analysis (alteration analyses by copy number based on expression data) identifies a recurrent genomic gain in the region 16q12-q24 in breast cancer patients with metastasis in 348 primary ER+ breast cancer tumors. Said region includes the locus 16q22-q24 containing the c-MAF gene. The gene expression and the development of metastasis have been associated by applying the "Cox log hazard ratio (HR)" model. The statistical significance has been obtained by permuting (1000 permutations) the HR logarithm in the entire genome, adjusting the p values via Benjamini-Hochberg to control a FDR (false discovery rate) at level of 0.05. Only those regions with at least 15 consecutive significant genes are reported in grey.

The ratio between alterations in the gene copy number in breast tumors and metastasis in breast cancer patients has then been evaluated. Thus, chromosomal regions with a significant number of genes associated with metastasis in patients have been identified using the "Cox log Hazard ratio (HR) model. The concepts in ACE (alteration analyses in the copy number in data expression) (Hu et al. 2009, cited ad supra) have been followed, locating potential regions with variations in the copy number. "PhenoTest" R packet functions have been used. Thus, the "log HR" have been obtained for each gene through the generalization of additive models, choosing parameters through crossed validation and the statistical significance has been evaluated by permuting (1000 permutations) the "log HR" through the entire genome, and adjusting the P-values via Benjamini-Hochberg to control the false discovery rate (FDR) at a level of 0.05. Only those regions with at least 15 consecutive and significant genes have been identified (FIG. 5B). The region 16q12-q24 including the c-MAF gene is among these regions.

Figures 6A, 6B:
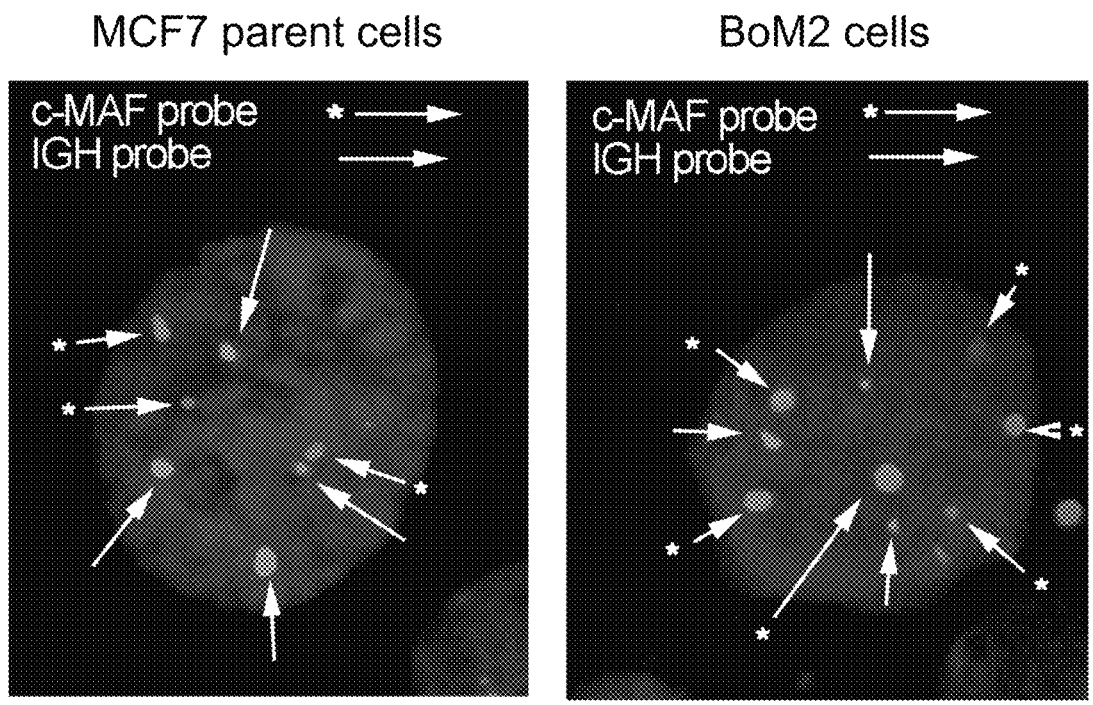
FIG. 6(A) shows the detection of the MAF and IGH gene copy number by means of fluorescence in situ hybridization (FISH) using a c-MAF gene-specific probe (arrow with asterisks) and an IGH gene-specific probe (arrows). The IGH gene is used as control. Scale: 25 µm.
FIG. 6(B) shows the quantification of the percentage of cells with the ratio indicated between the MAF gene copy number in comparison with the IGH gene copy number. (the total number of cells counted for each group is indicated).

The c-MAF gene copy number was subsequently characterized by means of fluorescence in situ hybridization (FISH) in MCF7 parent cells and in the cell line BoM2 characterized by having high tendency to form metastasis in bone tissue. The IGH gene copy number was determined simultaneously as the control of the experiment. The results showed that most of the MCF7 cells studied have a ratio between the c-MAF gene copy number and the IGF gene copy number equal to or less than 1.5, i.e., that the copy number of both genes is similar (FIG. 6), whereas most of the BoM2 cells studied showed a ratio between the c-MAF gene copy number and the IGF gene copy number greater than 2 (FIG. 6). These results demonstrate that the acquisition of the bone metastatic phenotype by the breast cancer cells is accompanied by an increase in the c-MAF gene copy number.

Conclusions c-MAF is a marker for the diagnosis and prognosis of and a causal target gene in metastasis process in breast cancer, particularly, in bone metastasis from ER+ breast cancer. This conclusion is supported by the clinical validation data and the gain-of-function and loss-of-function experiments forming part of the present invention.

Taking into account the results presented in the present invention wherein it is demonstrated that the c-MAF expression in primary tumors predicts a high risk of suffering bone metastasis in breast cancer patients, the patients whose tumors contain cells having a amplification in the genomic region chr16q22-q24 or an amplification of the c-MAF gene, will also be susceptible to suffer a high risk of bone metastasis. Therefore, the determination of the amplification of the c-MAF gene or of the locus 16q22-q24 is useful as a method of diagnosis and a method of predicting bone metastasis from primary breast cancer tumors.

Likewise, the experiments of the present invention (Examples 4 and 5) suggest that c-MAF is a suitable target for the treatment and/or prevention of the metastasis (both from ER+ and ER− tumors). Thus c-MAF inhibitors would be useful for the treatment of the metastasis in subjects with breast cancer.

The invention claimed is:

1. A method for the treatment of bone metastasis in a subject suffering ER+ breast cancer comprising administering an agent capable of avoiding, treating, or preventing bone degradation to said subject suffering ER+ breast cancer, wherein said subject has been determined to have an elevated c-MAF expression level in a primary breast cancer tumor tissue sample with respect to a control sample, wherein the control sample is a tumor tissue sample of breast cancer from a subject who has not suffered metastasis, wherein the agent capable of avoiding, treating or preventing bone degradation is selected from the group consisting of: a bisphosphonate, a RANKL inhibitor, PTH or a PRG analog, strontium ranelate, an estrogen receptor modulator, calcitonin and a cathepsin K inhibitor, wherein the subject is a human, wherein the subject has been determined to have an elevated c-MAF expression level through quantification of the c-MAF expression level, and wherein the quantification of the expression level comprises quantifying the messenger RNA (mRNA) of c-MAF, or a fragment of said mRNA, or quantifying the complementary DNA (cDNA) of c-MAF, or a fragment of said cDNA, wherein the c-MAF expression level is considered to be elevated when the expression level in the primary breast cancer tumor tissue sample is at least 5 times or greater than the control sample.

2. The method according to claim 1, wherein the RANKL inhibitor is selected from the group consisting of: a RANKL specific antibody and osteoprotegerin.

3. The method according to claim 2, wherein the RANKL specific antibody is denosumab.

4. The method according to claim 1, wherein the bisphosphonate is zoledronic acid.

5. The method according to claim 1, wherein the bisphosphonate is clodronate.

6. The method according to claim 1, wherein the bone metastasis is osteolytic metastasis.

7. The method according to claim 1, wherein the c-MAF expression level is quantified by means of a quantitative polymerase chain reaction (PCR), a DNA array, or an RNA array.

8. The method according to claim 1, wherein the elevated c-MAF expression level is at least about 10 times, 20 times, 30 times, 40 times, 50 times, 60 times, 70 times, 80 times, 90 times, 100 times or greater than the control sample.

9. A method for the treatment of bone metastasis in a subject suffering ER+ breast cancer comprising:
(i) obtaining a primary breast cancer tumor tissue sample from the human subject;
(ii) quantifying c-MAF expression level in the primary breast cancer tumor tissue sample;
(iii) comparing the expression level obtained in (ii) with the expression level of the c-MAF gene in a control sample, wherein the control sample is a tumor tissue sample of breast cancer from a subject who has not suffered metastasis,
(iv) determining that said subject has an elevated c-MAF expression level compared to a control sample, wherein the c-MAF expression level is considered to be elevated when the expression level in the primary breast cancer tumor tissue sample is at least 5 times or greater than the control sample; and
(v) administering an agent capable of avoiding, treating, or preventing bone degradation to said subject suffering ER+ breast cancer after step (iv), and
wherein the agent capable of avoiding, treating, or preventing bone degradation is selected from the group consisting of: a bisphosphonate, a RANKL inhibitor, PTH or a PRG analog, strontium ranelate, an estrogen receptor modulator, calcitonin and a cathepsin K inhibitor, wherein the quantification of the expression level comprises quantifying the messenger RNA (mRNA) of c-MAF, or a fragment of said mRNA, or quantifying the complementary DNA (cDNA) of c-MAF, or a fragment of said cDNA.

10. The method according to claim 9, wherein the RANKL inhibitor is selected from the group consisting of: a RANKL specific antibody and osteoprotegerin.

11. The method according to claim 10, wherein the RANKL specific antibody is denosumab.

12. The method according to claim 9, wherein the bisphosphonate is zoledronic acid.

13. The method according to claim 9, wherein the bisphosphonate is clodronate.

14. The method according to claim 9, wherein the expression level is quantified by means of a quantitative polymerase chain reaction (PCR), a DNA array, or an RNA array.

15. The method according to claim 1, wherein the estrogen receptor modulator inhibits the binding of estrogen to the estrogen receptor.

16. The method according to claim 1, wherein the estrogen receptor modulator is selected from the group consisting of progestogen, estradiol, droloxifene, raloxifiene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl) ethoxy]phenyl]-2H-1-benzopyran-3-yl]-phenyl-2,2-dimethyl propanoate, and SH646.

17. The method according to claim 9, wherein the estrogen receptor modulator inhibits the binding of estrogen to the estrogen receptor.

18. The method according to claim 9, wherein the estrogen receptor modulator is selected from the group consisting of progestogen, estradiol, droloxifene, raloxifiene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl) ethoxy]phenyl]-2H-1-benzopyran-3-yl]-phenyl-2,2-dimethyl propanoate, and SH646.

19. The method according to claim 1, wherein the method does not involve determining the expression level of any additional marker.

20. The method according to claim 9, wherein the method does not involve determining the expression level of any additional marker.

* * * * *

SEQUENCE LISTING

<160> NUMBER OF SEQ ID NOS: 12

<210> SEQ ID NO 1
<211> LENGTH: 6878
<212> TYPE: DNA
<213> ORGANISM: Homo sapiens

<400> SEQUENCE: 1

| | | |
|---|---|---|
| agaggcttta aaatcttttt tcatcttcta gctgtagctc gggctgcttg tcggcttggc | 60 | |
| ctcccctcc cccctttgct ctctgcctcg tctttcccca ggacttcgct attttgcttt | 120 | |
| tttaaaaaaa ggcaagaaag aactaaactc ccccctccct ctcctccagt cgggctgcac | 180 | |
| ctctgccttg cactttgcac agaggtagag agcgcgcgag ggagagagag gaaagaaaaa | 240 | |
| aaataataaa gagagccaag cagaagagga ggcgagaagc atgaagtgtt aactcccccg | 300 | |
| tgccaaggcc cgcgccgccc ggacagacgc ccgccgcgcc tccagccccg agcggacgcc | 360 | |
| gcgcgcgccc tgcctgcagc ccgggccggc gaggcgagcc cttccttatg caaagcgcgc | 420 | |
| agcggagcgg cgagcggggg acgccgcgca ccgggccggg ctcctccagc ttcgccgccg | 480 | |
| cagccaccac cgccgccacc gcagctcgcg gaggatcttc ccgagcctga agccgccggc | 540 | |
| tcggcgcgca aggaggcgag cgagcaagga ggggccgggg cgagcgaggg agcacattgg | 600 | |
| cgtgagcagg ggggagggag ggcgggcgcg ggggcgcgg gcagggcggg gggtgtgtg | 660 | |
| tgtgagcgcg ctcggaggtt tcgggccagc caccgccgcg caagctagaa gcgccccagc | 720 | |
| ccggcaagct ggctcacccg ctggccaccc agcacagccc gctggcccct ctcctgcagc | 780 | |
| ccatctggcg gagcggcggc ggcggcggcg gcggcggcag gagaatggca tcagaactgg | 840 | |
| caatgagcaa ctccgacctg cccaccagtc ccctggccat ggaatatgtt aatgacttcg | 900 | |
| atctgatgaa gtttgaagtg aaaaaggaac cggtggagac cgaccgcatc atcagccagt | 960 | |
| gcggccgtct catcgccggg ggctcgctgt cctccacccc catgagcacg ccgtgcagct | 1020 | |
| cggtgccccc ttcccccagc ttctcggcgc ccagcccggg ctcgggcagc gagcagaagg | 1080 | |
| cgcacctgga agactactac tggatgaccg gctacccgca gcagctgaac ccgaggcgc | 1140 | |
| tgggcttcag ccccgaggac gcggtcgagg cgctcatcag caacagccac cagctccagg | 1200 | |
| gcggcttcga tggctacgcg cgcggggcgc agcagctggc cgcggcggcc ggggccggtg | 1260 | |
| ccggcgcctc cttgggcggc agcggcgagg agatgggccc cgccgccgcc gtggtgtccg | 1320 | |
| ccgtgatcgc cgcggccgcc gcgcagacgc gcgcgggccc gcactaccac caccaccacc | 1380 | |
| accacgccgc cggccaccac caccacccga cggccggcgc gcccggcgcc gcgggcagcg | 1440 | |
| cggccgcctc ggccggtggc gctggggcg cgggcggcgg tggcccggcc agcgctgggg | 1500 | |
| gcggcggcgg cggcggcggc ggcggaggcg gcgggggcgc ggcggggggcg ggggcgccc | 1560 | |
| tgcacccgca ccacgccgcc ggcggcctgc acttcgacga ccgcttctcc gacgagcagc | 1620 | |
| tggtgaccat gtctgtgcgc gagctgaacc ggcagctgcg cggggtcagc aaggaggagg | 1680 | |
| tgatccggct gaagcagaag aggcggaccc tgaaaaaccg cggctatgcc cagtcctgcc | 1740 | |
| gcttcaagag ggtgcagcag agacacgtcc tggagtcgga gaagaaccag ctgctgcagc | 1800 | |
| aagtcgacca cctcaagcag gagatctcca ggctggtgcg cgagagggac gcgtacaagg | 1860 | |
| agaaatacga gaagttggtg agcagcggct tccgagaaaa cggctcgagc agcgacaacc | 1920 | |
| cgtcctctcc cgagtttttc atgtgagtct gacacgcgat tccagctagc accctgata | 1980 | |
| agtgctccgc gggggtccgg ctcgggtgtg ggcttgctag ttctagagcc atgctcgcca | 2040 | |
| ccacctcacc acccccaccc ccaccgagtt tggccccctt ggccccctac acacacacaa | 2100 | |
| acccgcacgc acacaccaca cacacacaca cacacacaca cacacccac accctgctcg | 2160 | |
| agtttgtggt ggtggtggct gttttaaact ggggagggaa tgggtgtctg gctcatggat | 2220 | |
| tgccaatctg aaattctcca taacttgcta gcttgttttt ttttttttt tacaccccc | 2280 | |
| cgccccaccc ccgacttgc acaatgttca atgatctcag cagagttctt catgtgaaac | 2340 | |
| gttgatcacc tttgaagcct gcatcattca catattttt cttcttcttc cccttcagtt | 2400 | |

```
catgaactgg tgttcatttt ctgtgtgtgt gtgtgtttta ttttgtttgg attttttttt    2460
ttaattttac ttttagagct tgctgtgttg cccaccttt ttccaacctc caccctcact    2520
ccttctcaac ccatctcttc cgagatgaaa gaaaaaaaaa agcaaagttt ttttttcttc    2580
tcctgagttc ttcatgtgag attgagcttg caaaggaaaa aaaaatgtga atgttatag    2640 acttgcagcg tgccgagttc catcgggttt ttttttttagc attgttatgc taaaatagag    2700
aaaaaaatcc tcatgaacct tccacaatca agcctgcatc aaccttctgg gtgtgacttg    2760
tgagttttgg ccttgtgatg ccaaatctga gagtttagtc tgccattaaa aaaactcatt    2820
ctcatctcat gcattattat gcttgctact ttgtcttagc aacaatgaac tataactgtt    2880
tcaaagactt tatggaaaag agacattata ttaataaaaa aaaaaagcct gcatgctgga    2940
catgtatggt ataattattt ttttccttttt tttttccttt ggcttggaaa tggacgttcg    3000
aagacttata gcatggcatt catactttg ttttattgcc tcatgacttt tttgagttta    3060
gaacaaaaca gtgcaaccgt agagccttct tcccatgaaa ttttgcatct gctccaaaac    3120
tgctttgagt tactcagaac ttcaacctcc caatgcactg aaggcattcc ttgtcaaaga    3180
taccagaatg ggttacacat ttaacctggc aaacattgaa gaactcttaa tgttttcttt    3240
ttaataagaa tgacgcccca cttgggggac taaaattgtg ctattgccga gaagcagtct    3300
aaaatttatt ttttaaaaag agaaactgcc ccattattt tggtttgttt tattttatt    3360 ttatattttt tggcttttgg tcattgtcaa atgtggaatg ctctgggttt ctagtatata    3420
atttaattct agttttttata atctgttagc ccagttaaaa tgtatgctac agataaagga    3480
atgttataga taaatttgaa agagttaggt ctgtttagct gtagattttt taaacgattg    3540
atgcactaaa ttgttttacta ttgtgatgtt aaggggggta gagtttgcaa ggggactgtt    3600 taaaaaagt agcttataca gcatgtgctt gcaacttaaa tataagttgg gtatgtgtag    3660
tctttgctat accactgact gtattgaaaa ccaaagtatt aagagggaa acgcccctgt    3720 ttatatctgt agggtattt tacattcaaa aatgtatgtt tttttttctt ttcaaaatta    3780
aagtatttgg gactgaattg cactaagata taacctgcaa gcatataata caaaaaaaaa    3840
ttgcaaaact gtttagaacg ctaataaaat ttatgcagtt ataaaaatgg cattactgca    3900
cagttttaag atgatgcaga ttttttttaca gttgtattgt ggtgcagaac tggattttct    3960
gtaacttaaa aaaaaatcca cagttttaaa ggcaataatc agtaaatgtt atttcaggg    4020 actgacatcc tgtctttaaa aagaaatgaa aagtaaatct taccacaata aatataaaaa    4080
aatcttgtca gttactttc ttttacatat tttgctgtgc aaaattgttt tatatcttga    4140
gttactaact aaccacgcgt gttgttccta tgtgcttttc tttcattttc aattctggtt    4200
atatcaagaa aagaataatc tacaataata aacggcattt ttttttgatt ctgtactcag    4260
tttcttagtg tacagtttaa ctgggcccaa caacctcgtt aaaagtgtaa aatgcatcct    4320
tttctccagt ggaaggattc ctggaggaat agggagacag taattcaggg tgaaattata    4380
ggctgttttt tgaagtgagg aggctggccc catatactga ttagcaatat ttaatataga    4440
tgtaaattat gacctcattt ttttctcccc aaagttttca gttttcaaat gagttgagcc    4500
ataattgccc ttggtaggaa aaacaaaaca aaacagtgga actaggcttc ctgagcatgg    4560
ccctacactt ctgatcagga gcaaagccat ccatagacag aggagccgga caaatatggc    4620
gcatcagagg tggcttgcgc acatatgcat tgaacggtaa agagaaacag cgcttgcctt    4680
ttcactaaag ttgactattt ttccttcttc tcttacacac cgagattttc ttgttagcaa    4740
```

```
ggcctgacaa gatttaacat aaacatgaca aatcatagtt gtttgttttg ttttgctttt    4800
ctctttaaca ctgaagatca tttgtcttaa ataggaaaaa gaaatccac tccttacttc     4860
catatttcca agtacatatc tggtttaaac tatgttatca aatcatattt caccgtgaat    4920
attcagtgga gaacttctct acctggatga gctagtaatg atttcagatc atgctatccc    4980
cagaaataaa agcaaaaaat aatacctgtg tggaatatag gctgtgcttt gatttactgg    5040
tatttacccc aaaataggct gtgtatgggg gctgacttaa agatcccttg gaaagactca    5100
aaactacctt cactagtagg actcctaagc gctgacctat ttttaaatga cacaaattca    5160
tgaaactaat gttacaaatt catgcagttt gcactcttag tcatcttccc ctagcacacc    5220
aatagaatgt tagacaaagc cagcactgtt ttgaaaatac agccaaacac gatgactttt    5280
gttttgtttt ctgccgttct taaaagaaaa aaagataata ttgcaactct gactgaaaga    5340
cttatttta agaaaacagg ttgtgtttgg tgctgctaag ttctggccag tttatcatct     5400
ggccttcctg cctatttttt acaaaacacg aagacagtgt gtaacctcga cattttgacc    5460
ttcctttatg tgctagttta gacaggctcc tgaatccaca cttaattttg cttaacaaaa    5520
gtcttaatag taaacctccc ctcatgagct tgaagtcaag tgttcttgac ttcagatatt    5580
tctttccttt tttttttttt ttcctcatca caactaagag atacacaaac tctgaagaag    5640
cagaaatgga gagaatgctt ttaacaaaaa agcatctgat gaaagatttt aggcaaacat    5700
tctcaaaata agagtgatat tctggatgta gttattgcag ttatctcatg acaaatgagg    5760
cctggattgg aaggaaaata tagttgtgta gaattaagca ttttgatagg aatctacaag    5820
gtagttgaat ataataagca ggtttgggcc cccaaacttt agaaaatcaa atgcaaaggt    5880
gctggcaaaa atgaggtttg agtggctggc tgtaagagaa ggttaactcc tagtaaaagg    5940
catttttaga aataacaatt actgaaaact ttgaagtata gtgggagtag caaacaaata    6000
catgtttttt ttttcttaca aagaactcct aaatcctgag taagtgccat tcattacaat    6060
aagtctctaa atttaaaaaa aaaaaaatca tatgaggaaa tctagctttc cccttttacgc   6120
tgcgtttgat ctttgtctaa atagtgttaa aattcctttc attccaatta cagaactgag    6180
cccactcgca agtggagcc atcagtggga tacgccacat tttggaagcc ccagcatcgt     6240
gtacttacca gtgtgttcac aaaatgaaat ttgtgtgaga gctgtacatt aaaaaaaatc    6300
atcattatta ttattatttg cagtcatgga gaaccaccta cccctgactt ctgtttagtc    6360
tccttttttaa ataaaaatta ctgtgttaga gaagaaggct attaaatgta gtagttaact   6420
atgcctcttg tctgggggtt tcatagagac cggtaggaaa gcgcactcct gcttttcgat    6480
ttatggtgtg tgcaagtaaa caggtgcatt gctttcaacc tgccatacta gttttaaaaa    6540
ttcactgaaa ttacaaagat acatatatat gcatatatat aatggaaagt ttcccggaat    6600
gcaacaatta gcattttaaa atcatatata ggcatgcaca ttctaaatag tacttttca    6660
tgcttcattg tttctctggc agataatttt actaagaaga aaaatagata ttcgactccc    6720
cttccctaaa caaatccacg ggcagaggct ccagcggagc cgagccccct ggttttctcg    6780
taggccctag acggtgttgc atttatcagt gatgtcaaac gtgctcattt gtcagacata    6840
gctgtaaatg aaaacaatgt gtggcaaaat acaaagtt                            6878
```

<210> SEQ ID NO 2
<211> LENGTH: 2656
<212> TYPE: DNA
<213> ORGANISM: Homo sapiens

<400> SEQUENCE: 2

```
gaggctttaa aatctttttt catcttctag ctgtagctcg ggctgcttgt cggcttggcc      60
tccccctccc cccttcgctc tctgcctcgt ctttccccag gacttcgcta ttttgctttt     120
ttaaaaaaag gcaagaaaga actaaactcc cccctccctc tcctccagtc gggctgcacc     180
tctgccttgc actttgcaca gaggtagaga gcgcgcgagg gagagagagg aaagaaaaaa     240
aataataaag agagccaagc agaagaggag gcgagaagca tgaagtgtta actccccgt     300 gccaaggccc gcgccgcccg gacagacgcc cgccgcgcct ccagcccga gcggacgccg     360 cgcgcgccct gcctgcagcc cgggccggcg aggcgagccc ttccttatgc aaagcgcgca     420
gcggagcggc gagcggggga cgccgcgcac cgggccgggc tcctccagct tcgccgccgc     480
agccaccacc gccgccaccg cagctcgcgg aggatcttcc cgagcctgaa gccgccggct     540
cggcgcgcaa ggaggcgagc gagcaaggag gggccggggc gagcgaggga gcacattggc     600
gtgagcaggg gggagggagg gcgggcgcgg ggggcgcggg cagggcgggg gggtgtgtgt     660
gtgagcgcgc tcggaggttt cgggccagcc accgccgcgc aagctagaag cgccccagcc     720
cggcaagctg gctcacccgc tggccaccca gcacagcccg ctggcccctc tcctgcagcc     780
catctggcgg agcggcggcg gcggcggcgg cggcggcagg agaatggcat cagaactggc     840
aatgagcaac tccgacctgc ccaccagtcc cctggccatg gaatatgtta atgacttcga     900
tctgatgaag tttgaagtga aaaaggaacc ggtggagacc gaccgcatca tcagccagtg     960
cggccgtctc atcgccgggg gctcgctgtc ctccaccccc atgagcacgc cgtgcagctc    1020
ggtgccccct tcccccagct tctcggcgcc cagcccgggc tcgggcagcg agcagaaggc    1080
gcacctggaa gactactact ggatgaccgg ctacccgcag cagctgaacc ccgaggcgct    1140
gggcttcagc cccgaggacg cggtcgaggc gctcatcagc aacagccacc agctccaggg    1200
cggcttcgat ggctacgcgc gcggggcgca gcagctggcc gcggcggccg gggccggtgc    1260
cggcgcctcc ttgggcggca gcggcgagga gatgggcccc gccgccgccg tggtgtccgc    1320
cgtgatcgcc gcggccgccg cgcagagcgg cgcgggcccc cactaccacc accaccacca    1380
ccacgccgcc ggccaccacc accacccgac ggccggcgcg cccggcgccg cgggcagcgc    1440
ggccgcctcg gccggtggcg ctgggggcgc gggcggcggt ggcccggcca gcgctggggg    1500
cggcggcggc ggcggcggcg gcggaggcgg cgggggcgcg gcgggggcgg ggggcgccct    1560
gcacccgcac cacgccgccg gcggcctgca cttcgacgac cgcttctccg acgagcagct    1620
ggtgaccatg tctgtgcgcg agctgaaccg gcagctgcgc ggggtcagca aggaggaggt    1680
gatccggctg aagcagaaga ggcggaccct gaaaaaccgc ggctatgccc agtcctgccg    1740
cttcaagagg gtgcagcaga gacacgtcct ggagtcggag aagaaccagc tgctgcagca    1800
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttca taactgagcc cactcgcaag ttggagccat cagtgggata    1980
cgccacattt tggaagcccc agcatcgtgt acttaccagt gtgttcacaa aatgaaattt    2040
gtgtgagagc tgtacattaa aaaaaatcat cattattatt attatttgca gtcatggaga    2100
accacctacc cctgacttct gtttagtctc cttttaaat aaaaattact gtgttagaga    2160
agaaggctat taaatgtagt agttaactat gcctcttgtc tgggggtttc atagagaccg    2220
gtaggaaagc gcactcctgc ttttcgattt atggtgtgtg caagtaaaca ggtgcattgc    2280
tttcaacctg ccatactagt tttaaaaatt cactgaaatt acaaagatac atatatatgc    2340
```

| | | |
|---|---|---|
| atatatataa tggaaagttt cccggaatgc aacaattagc atttaaaat catatatagg | 2400 | |
| catgcacatt ctaaatagta cttttttcatg cttcattgtt tctctggcag ataattttac | 2460 | |
| taagaagaaa aatagatatt cgactcccct tccctaaaca aatccacggg cagaggctcc | 2520 | |
| agcggagccg agcccctgg ttttctcgta ggccctagac ggtgttgcat ttatcagtga | 2580 | |
| tgtcaaacgt gctcatttgt cagacatagc tgtaaatgaa aacaatgtgt ggcaaaatac | 2640 | |
| aaagttaaaa aaaaaa | 2656 | |

```
<210> SEQ ID NO 3
<211> LENGTH: 6887
<212> TYPE: DNA
<213> ORGANISM: Homo sapiens

<400> SEQUENCE: 3
```

| | | |
|---|---|---|
| gaggctttaa aatctttttt catcttctag ctgtagctcg ggctgcttgt cggcttggcc | 60 | |
| tccccctccc cccttttgctc tctgcctcgt cttcccccag gacttcgcta ttttgctttt | 120 | |
| ttaaaaaaag gcaagaaaga actaaactcc cccctccctc tcctccagtc gggctgcacc | 180 | |
| tctgccttgc actttgcaca gaggtagaga gcgcgcgagg gagagagagg aaagaaaaaa | 240 | |
| aataataaag agagccaagc agaagaggag gcgagaagca tgaagtgtta actcccccgt | 300 | |
| gccaaggccc gcgccgcccg gacagacgcc cgccgcgcct ccagccccga gcggacgccg | 360 | |
| cgcgcgccct gcctgcagcc cgggccgcg aggcgagccc ttccttatgc aaagcgcgca | 420 | |
| gcggagcggc gagcggggga cgccgcgcac cgggccgggc tcctccagct tcgccgccgc | 480 | |
| agccaccacc gccgccaccg cagctcgcgg aggatcttcc cgagcctgaa gccgccggct | 540 | |
| cggcgcgcaa ggaggcgagc gagcaaggag gggccggggc gagcgaggga gcacattggc | 600 | |
| gtgagcaggg gggagggagg gcgggcgcgg ggggcgcggg cagggcgggg gggtgtgtgt | 660 | |
| gtgagcgcgc tcggaggttt cgggccagcc accgccgcgc aagctagaag cgccccagcc | 720 | |
| cggcaagctg gctcacccgc tggccaccca gcacagcccg ctggcccctc tcctgcagcc | 780 | |
| catctggcgg agcggcggcg gcggcggcgg cggcggcagg agaatggcat cagaactggc | 840 | |
| aatgagcaac tccgacctgc ccaccagtcc cctggccatg gaatatgtta atgacttcga | 900 | |
| tctgatgaag tttgaagtga aaaggaacc ggtggagacc gaccgcatca tcagccagtg | 960 | |
| cggccgtctc atcgcggggg gctcgctgtc ctccaccccc atgagcacgc cgtgcagctc | 1020 | |
| ggtgcccct tccccagct tctcggcgcc cagcccgggc tcgggcagcg agcagaaggc | 1080 | |
| gcacctggaa gactactact ggatgaccgg ctacccgcag cagctgaacc ccgaggcgct | 1140 | |
| gggcttcagc cccgaggacg cggtcgaggc gctcatcagc aacagccacc agctccaggg | 1200 | |
| cggcttcgat ggctacgcgc gcgggggcca gcagctggcc gcggcggccg gggcggtgc | 1260 | |
| cggcgcctcc ttgggcggca gcggcgagga gatgggcccc gccgccgccg tggtgtccgc | 1320 | |
| cgtgatcgcc gcggccgccg cgcagagcgg cgcgggcccg cactaccacc accaccacca | 1380 | |
| ccacgccgcc ggccaccacc accacccgac ggccggcgcg cccggcgccg cgggcagcgc | 1440 | |
| ggccgcctcg gccggtggcg ctggggcgcg gggcggcggt ggcccggcca gcgctggggg | 1500 | |
| cggcggcggc ggcggcggcg gcgaggcgg cgggggcgcg gcggggcgg ggggcgccct | 1560 | |
| gcacccgcac cacgccgccg gcggcctgca cttcgacgac cgcttctccg acgagcagct | 1620 | |
| ggtgaccatg tctgtgcgcg agctgaaccg gcagctgcgc gggtcagca aggaggaggt | 1680 | |
| gatccggct aagcagaaga ggcggaccct gaaaaaccgc ggctatgccc agtcctgccg | 1740 | |
| cttcaagagg gtgcagcaga gacacgtcct ggagtcggag aagaaccagc tgctgcagca | 1800 | |

```
agtcgaccac ctcaagcagg agatctccag gctggtgcgc gagagggacg cgtacaagga    1860
gaaatacgag aagttggtga gcagcggctt ccgagaaaac ggctcgagca gcgacaaccc    1920
gtcctctccc gagttttca tgtgagtctg acacgcgatt ccagctagcc accctgataa    1980
gtgctccgcg ggggtccggc tcgggtgtgg gcttgctagt tctagagcca tgctcgccac    2040
cacctcacca cccccacccc caccgagttt ggccccttg gccccctaca cacacacaaa    2100
cccgcacgca cacaccacac acacacacac acacacacac acaccccaca ccctgctcga    2160
gtttgtggtg gtggtggctg ttttaaactg gggagggaat gggtgtctgg ctcatggatt    2220
gccaatctga aattctccat aacttgctag cttgttttt tttttttttt acaccccccc    2280
gccccacccc cggacttgca caatgttcaa tgatctcagc agagttcttc atgtgaaacg    2340
ttgatcacct ttgaagcctg catcattcac atattttttc ttcttcttcc ccttcagttc    2400
atgaactggt gttcatttc tgtgtgtgtg tgtgttttat tttgtttgga tttttttttt    2460
taattttact tttagagctt gctgtgttgc ccaccttttt tccaacctcc accctcactc    2520
cttctcaacc catctcttcc gagatgaaag aaaaaaaaaa gcaaagttt ttttcttct     2580 cctgagttct tcatgtgaga ttgagcttgc aaaggaaaaa aaaatgtgaa atgttataga    2640
cttgcagcgt gccgagttcc atcgggtttt tttttagca ttgttatgct aaaatagaga    2700
aaaaaatcct catgaacctt ccacaatcaa gcctgcatca accttctggg tgtgacttgt    2760
gagttttggc cttgtgatgc caaatctgag agtttagtct gccattaaaa aaactcattc    2820
tcatctcatg cattattatg cttgctactt tgtcttagca acaatgaact ataactgttt    2880 caaagactt atggaaaaga gacattatat taataaaaa aaaaagcctg catgctggac    2940
atgtatggta taattatttt ttcctttttt tttccttttg gcttggaaat ggacgttcga    3000
agacttatag catggcattc atacttttgt tttattgcct catgactttt ttgagtttag    3060
aacaaaacag tgcaaccgta gagccttctt cccatgaaat tttgcatctg ctccaaaact    3120
gctttgagtt actcagaact tcaacctccc aatgcactga aggcattcct tgtcaaagat    3180
accagaatgg gttacacatt taacctggca aacattgaag aactcttaat gttttcttt     3240 taataagaat gacgcccac tttggggact aaaattgtgc tattgccgag aagcagtcta    3300 aaattatt tttaaaaga gaaactgccc cattattttt ggttgtttt attttattt        3360 tatatttttt ggcttttggt cattgtcaaa tgtggaatgc tctgggtttc tagtatataa    3420
tttaattcta gttttataa tctgttagcc cagttaaaat gtatgctaca gataaaggaa    3480
tgttatagat aaatttgaaa gagttaggtc tgtttagctg tagatttttt aaacgattga    3540
tgcactaaat tgtttactat tgtgatgtta aggggggtag agtttgcaag gggactgttt    3600
aaaaaaagta gctatacag catgtgcttg caacttaaat ataagttggg tatgtgtagt    3660
ctttgctata ccactgactg tattgaaaac caaagtatta agaggggaaa cgcccctgtt    3720
tatatctgta ggggtatttt acattcaaaa atgtatgttt ttttttcttt tcaaaattaa    3780
agtatttggg actgaattgc actaagatat aacctgcaag catataatac aaaaaaaaat    3840
tgcaaaactg tttagaacgc taataaaatt tatgcagtta taaaaatggc attactgcac    3900
agttttaaga tgatgcagat ttttttacag ttgtattgtg gtgcagaact ggattttctg    3960
taacttaaaa aaaaatccac agttttaaag gcaataatca gtaaatgtta ttttcaggga    4020
ctgacatcct gtctttaaaa agaaatgaaa agtaaatctt accacaataa atataaaaaa    4080
atcttgtcag ttacttttct tttacatatt ttgctgtgca aaattgtttt atatcttgag    4140
```

-continued

```
ttactaacta accacgcgtg ttgttcctat gtgcttttct ttcattttca attctggtta    4200
tatcaagaaa agaataatct acaataataa acggcatttt tttttgattc tgtactcagt    4260
ttcttagtgt acagtttaac tgggcccaac aacctcgtta aaagtgtaaa atgcatcctt    4320
ttctccagtg gaaggattcc tggaggaata gggagacagt aattcagggt gaaattatag    4380
gctgttttt gaagtgagga ggctggcccc atatactgat tagcaatatt taatatagat    4440
gtaaattatg acctcatttt tttctcccca aagttttcag ttttcaaatg agttgagcca    4500
taattgccct tggtaggaaa acaaaacaa aacagtggaa ctaggcttcc tgagcatggc    4560
cctacacttc tgatcaggag caaagccatc catagacaga ggagccggac aaatatggcg    4620
catcagaggt ggcttgcgca catatgcatt gaacggtaaa gagaaacagc gcttgccttt    4680
tcactaaagt tgactatttt tccttcttct cttacacacc gagatttcct tgttagcaag    4740
gcctgacaag atttaacata aacatgacaa atcatagttg tttgttttgt tttgcttttc    4800
tctttaacac tgaagatcat ttgtcttaaa taggaaaaag aaaatccact ccttacttcc    4860
atatttccaa gtacatatct ggtttaaact atgttatcaa atcatatttc accgtgaata    4920
ttcagtggag aacttctcta cctggatgag ctagtaatga tttcagatca tgctatcccc    4980
agaaataaaa gcaaaaaata atacctgtgt ggaatatagg ctgtgctttg atttactggt    5040
atttacccca aaataggctg tgtatggggg ctgacttaaa gatcccttgg aaagactcaa    5100
aactaccttc actagtagga ctcctaagcg ctgacctatt tttaaatgac acaaattcat    5160
gaaactaatg ttacaaattc atgcagtttg cactcttagt catcttcccc tagcacacca    5220
atagaatgtt agacaaagcc agcactgttt tgaaaataca gccaaacacg atgacttttg    5280
ttttgttttc tgccgttctt aaaagaaaaa aagataatat tgcaactctg actgaaagac    5340
ttattttaa gaaaacaggt tgtgtttggt gctgctaagt tctggccagt ttatcatctg    5400
gccttcctgc ctattttta caaaacacga agacagtgtg taacctcgac attttgacct    5460
tcctttatgt gctagtttag acaggctcct gaatccacac ttaattttgc ttaacaaaag    5520
tcttaatagt aaacctcccc tcatgagctt gaagtcaagt gttcttgact tcagatattt    5580
cttttccttt tttttttt tcctcatcac aactaagaga tacacaaact ctgaagaagc    5640
agaaatggag agaatgcttt taacaaaaaa gcatctgatg aaagatttta ggcaaacatt    5700
ctcaaaataa gagtgatatt ctggatgtag ttattgcagt tatctcatga caaatgaggc    5760
ctggattgga aggaaaatat agttgtgtag aattaagcat tttgatagga atctacaagg    5820
tagttgaata taataagcag gtttgggccc ccaaacttta gaaatcaaa tgcaaaggtg    5880
ctggcaaaaa tgaggtttga gtggctggct gtaagagaag gttaactcct agtaaaaggc    5940
attttagaa ataacaatta ctgaaaactt tgaagtatag tgggagtagc aaacaaatac    6000
atgttttttt tttcttacaa agaactccta aatcctgagt aagtgccatt cattacaata    6060
agtctctaaa tttaaaaaa aaaaaatcat atgaggaaat ctagctttcc cctttacgct    6120
gcgtttgatc tttgtctaaa tagtgttaaa attcctttca ttccaattac agaactgagc    6180
ccactcgcaa gttggagcca tcagtgggat acgccacatt ttggaagccc cagcatcgtg    6240
tacttaccag tgtgttcaca aaatgaaatt tgtgtgagag ctgtacatta aaaaaaatca    6300
tcattattat tattatttgc agtcatggag aaccacctac ccctgacttc tgtttagtct    6360
ccttttttaaa taaaaattac tgtgttagag aagaaggcta ttaaatgtag tagttaacta    6420
tgcctcttgt ctgggggttt catagagacc ggtaggaaag cgcactcctg cttttcgatt    6480
tatggtgtgt gcaagtaaac aggtgcattg ctttcaacct gccatactag ttttaaaaat    6540
```

-continued

```
tcactgaaat tacaaagata catatatatg catatatata atggaaagtt tcccggaatg    6600
caacaattag cattttaaaa tcatatatag gcatgcacat tctaaatagt acttttcat    6660 gcttcattgt ttctctggca gataatttta ctaagaagaa aaatagatat tcgactcccc    6720
ttccctaaac aaatccacgg gcagaggctc cagcggagcc gagcccctg gtttctcgt    6780 aggccctaga cggtgttgca tttatcagtg atgtcaaacg tgctcatttg tcagacatag    6840
ctgtaaatga aaacaatgtg tggcaaaata caaagttaaa aaaaaaa              6887
```

<210> SEQ ID NO 4
<211> LENGTH: 403
<212> TYPE: PRT
<213> ORGANISM: Homo sapiens

<400> SEQUENCE: 4

```
Met Ala Ser Glu Leu Ala Met Ser Asn Ser Asp Leu Pro Thr Ser Pro
1               5                   10                  15

Leu Ala Met Glu Tyr Val Asn Asp Phe Asp Leu Met Lys Phe Glu Val
            20                  25                  30

Lys Lys Glu Pro Val Glu Thr Asp Arg Ile Ile Ser Gln Cys Gly Arg
        35                  40                  45

Leu Ile Ala Gly Gly Ser Leu Ser Ser Thr Pro Met Ser Thr Pro Cys
    50                  55                  60

Ser Ser Val Pro Pro Ser Pro Ser Phe Ser Ala Pro Ser Pro Gly Ser
65                  70                  75                  80

Gly Ser Glu Gln Lys Ala His Leu Glu Asp Tyr Tyr Trp Met Thr Gly
                85                  90                  95

Tyr Pro Gln Gln Leu Asn Pro Glu Ala Leu Gly Phe Ser Pro Glu Asp
            100                 105                 110

Ala Val Glu Ala Leu Ile Ser Asn Ser His Gln Leu Gln Gly Gly Phe
        115                 120                 125

Asp Gly Tyr Ala Arg Gly Ala Gln Gln Leu Ala Ala Ala Gly Ala
    130                 135                 140

Gly Ala Gly Ala Ser Leu Gly Gly Ser Gly Glu Glu Met Gly Pro Ala
145                 150                 155                 160

Ala Ala Val Val Ser Ala Val Ile Ala Ala Ala Ala Gln Ser Gly
                165                 170                 175

Ala Gly Pro His Tyr His His His His His Ala Ala Gly His His
            180                 185                 190

His His Pro Thr Ala Gly Ala Pro Gly Ala Ala Gly Ser Ala Ala Ala
        195                 200                 205

Ser Ala Gly Gly Ala Gly Gly Ala Gly Gly Gly Pro Ala Ser Ala
    210                 215                 220

Gly Gly Gly Gly Gly Gly Gly Gly Gly Gly Gly Gly Ala Ala
225                 230                 235                 240

Gly Ala Gly Gly Ala Leu His Pro His His Ala Ala Gly Gly Leu His
                245                 250                 255

Phe Asp Asp Arg Phe Ser Asp Glu Gln Leu Val Thr Met Ser Val Arg
            260                 265                 270

Glu Leu Asn Arg Gln Leu Arg Gly Val Ser Lys Glu Val Ile Arg
        275                 280                 285

Leu Lys Gln Lys Arg Arg Thr Leu Lys Asn Arg Gly Tyr Ala Gln Ser
    290                 295                 300

Cys Arg Phe Lys Arg Val Gln Gln Arg His Val Leu Glu Ser Glu Lys
```

```
                305                 310                 315                 320
Asn Gln Leu Leu Gln Gln Val Asp His Leu Lys Gln Glu Ile Ser Arg
                    325                 330                 335
Leu Val Arg Glu Arg Asp Ala Tyr Lys Glu Lys Tyr Glu Lys Leu Val
                340                 345                 350
Ser Ser Gly Phe Arg Glu Asn Gly Ser Ser Asp Asn Pro Ser Ser
                355                 360                 365
Pro Glu Phe Phe Ile Thr Glu Pro Thr Arg Lys Leu Glu Pro Ser Val
            370                 375                 380
Gly Tyr Ala Thr Phe Trp Lys Pro Gln His Arg Val Leu Thr Ser Val
385                 390                 395                 400
Phe Thr Lys

<210> SEQ ID NO 5
<211> LENGTH: 373
<212> TYPE: PRT
<213> ORGANISM: Homo sapiens

<400> SEQUENCE: 5

Met Ala Ser Glu Leu Ala Met Ser Asn Ser Asp Leu Pro Thr Ser Pro
1               5                   10                  15
Leu Ala Met Glu Tyr Val Asn Asp Phe Asp Leu Met Lys Phe Glu Val
                20                  25                  30
Lys Lys Glu Pro Val Glu Thr Asp Arg Ile Ile Ser Gln Cys Gly Arg
            35                  40                  45
Leu Ile Ala Gly Gly Ser Leu Ser Ser Thr Pro Met Ser Thr Pro Cys
        50                  55                  60
Ser Ser Val Pro Pro Ser Pro Ser Phe Ser Ala Pro Ser Pro Gly Ser
65                  70                  75                  80
Gly Ser Glu Gln Lys Ala His Leu Glu Asp Tyr Tyr Trp Met Thr Gly
                85                  90                  95
Tyr Pro Gln Gln Leu Asn Pro Glu Ala Leu Gly Phe Ser Pro Glu Asp
                100                 105                 110
Ala Val Glu Ala Leu Ile Ser Asn Ser His Gln Leu Gln Gly Gly Phe
            115                 120                 125
Asp Gly Tyr Ala Arg Gly Ala Gln Gln Leu Ala Ala Ala Gly Ala
        130                 135                 140
Gly Ala Gly Ala Ser Leu Gly Gly Ser Gly Glu Met Gly Pro Ala
145                 150                 155                 160
Ala Ala Val Val Ser Ala Val Ile Ala Ala Ala Ala Gln Ser Gly
                165                 170                 175
Ala Gly Pro His Tyr His His His His His Ala Ala Gly His His
                180                 185                 190
His His Pro Thr Ala Gly Ala Pro Gly Ala Ala Gly Ser Ala Ala Ala
            195                 200                 205
Ser Ala Gly Gly Ala Gly Ala Gly Gly Gly Pro Ala Ser Ala
        210                 215                 220
Gly Gly Gly Gly Gly Gly Gly Gly Gly Gly Gly Ala Ala
225                 230                 235                 240
Gly Ala Gly Gly Ala Leu His Pro His His Ala Ala Gly Gly Leu His
                245                 250                 255
Phe Asp Asp Arg Phe Ser Asp Glu Gln Leu Val Thr Met Ser Val Arg
                260                 265                 270
Glu Leu Asn Arg Gln Leu Arg Gly Val Ser Lys Glu Glu Val Ile Arg
```

```
                275                 280                 285
Leu Lys Gln Lys Arg Thr Leu Lys Asn Arg Gly Tyr Ala Gln Ser
    290                 295                 300

Cys Arg Phe Lys Arg Val Gln Gln Arg His Val Leu Glu Ser Glu Lys
305                 310                 315                 320

Asn Gln Leu Leu Gln Gln Val Asp His Leu Lys Gln Glu Ile Ser Arg
                325                 330                 335

Leu Val Arg Glu Arg Asp Ala Tyr Lys Glu Lys Tyr Glu Lys Leu Val
            340                 345                 350

Ser Ser Gly Phe Arg Glu Asn Gly Ser Ser Ser Asp Asn Pro Ser Ser
                355                 360                 365

Pro Glu Phe Phe Met
    370

<210> SEQ ID NO 6
<211> LENGTH: 19
<212> TYPE: RNA
<213> ORGANISM: Artificial Sequence
<220> FEATURE:
<223> OTHER INFORMATION: ARNip specific para c-MAF

<400> SEQUENCE: 6
acggcucgag cagcgacaa                                                19

<210> SEQ ID NO 7
<211> LENGTH: 19
<212> TYPE: RNA
<213> ORGANISM: Artificial Sequence
<220> FEATURE:
<223> OTHER INFORMATION: ARNip specific para c-MAF

<400> SEQUENCE: 7
cuuaccagug uguucacaa                                                19

<210> SEQ ID NO 8
<211> LENGTH: 20
<212> TYPE: RNA
<213> ORGANISM: Artificial Sequence
<220> FEATURE:
<223> OTHER INFORMATION: ARNip specific para c-MAF

<400> SEQUENCE: 8
uggaagacua cuacuggaug                                               20

<210> SEQ ID NO 9
<211> LENGTH: 20
<212> TYPE: RNA
<213> ORGANISM: Artificial Sequence
<220> FEATURE:
<223> OTHER INFORMATION: ARNip specific para c-MAF

<400> SEQUENCE: 9
auuugcaguc auggagaacc                                               20

<210> SEQ ID NO 10
<211> LENGTH: 20
<212> TYPE: RNA
<213> ORGANISM: Artificial Sequence
<220> FEATURE:
<223> OTHER INFORMATION: ARNip specific para c-MAF

<400> SEQUENCE: 10
caaggagaaa uacgagaagu                                               20
```

```
<210> SEQ ID NO 11
<211> LENGTH: 20
<212> TYPE: RNA
<213> ORGANISM: Artificial Sequence
<220> FEATURE:
<223> OTHER INFORMATION: ARNip specific para c-MAF

<400> SEQUENCE: 11
acaaggagaa auacgagaag                                               20

<210> SEQ ID NO 12
<211> LENGTH: 20
<212> TYPE: RNA
<213> ORGANISM: Artificial Sequence
<220> FEATURE:
<223> OTHER INFORMATION: ARNip specific para c-MAF

<400> SEQUENCE: 12
accuggaaga cuacuacugg                                               20
```